(12) United States Patent
Lambrechts et al.

(10) Patent No.: US 11,814,688 B2
(45) Date of Patent: Nov. 14, 2023

(54) MARKERS FOR DETERMINING TUMOR HYPOXIA

(71) Applicants: VIB VZW, Ghent (BE); Katholieke Universiteit Leuven, K.U. Leuven R&D, Leuven (BE); Life Sciences Research Partners VZW, Leuven (BE)

(72) Inventors: Diether Lambrechts, Kessel-Lo (BE); Bernard Thienpont, Jette (BE)

(73) Assignees: VIB VZW, Ghent (BE); Katholieke Universiteit Leuven, K.U. Leuven R & D, Leuven (BE); Life Sciences Research Partners VZW, Leuven (BE)

( * ) Notice: Subject to any disclaimer, the term of this patent is extended or adjusted under 35 U.S.C. 154(b) by 0 days.

(21) Appl. No.: 17/728,506

(22) Filed: Apr. 25, 2022

(65) Prior Publication Data
US 2022/0259677 A1   Aug. 18, 2022

Related U.S. Application Data

(62) Division of application No. 15/555,752, filed as application No. PCT/EP2016/054671 on Mar. 4, 2016, now abandoned.

(30) Foreign Application Priority Data

Mar. 6, 2015   (EP) ..................... 15158096

(51) Int. Cl.
*C12Q 1/6886*   (2018.01)
(52) U.S. Cl.
CPC ..... *C12Q 1/6886* (2013.01); *C12Q 2600/154* (2013.01)
(58) Field of Classification Search
None
See application file for complete search history.

(56) References Cited

FOREIGN PATENT DOCUMENTS

| WO | 2005012569 A1 | 2/2005 |
|---|---|---|
| WO | 2009120249 A1 | 10/2009 |
| WO | 2010115119 A2 | 10/2010 |
| WO | 2011076895 A1 | 6/2011 |
| WO | 2013022872 A1 | 2/2013 |
| WO | 2014020048 A1 | 2/2014 |
| WO | 2014062218 A1 | 4/2014 |
| WO | 2015020929 A2 | 2/2015 |
| WO | 2015023967 A2 | 2/2015 |
| WO | 2015029947 A1 | 3/2015 |

OTHER PUBLICATIONS

Kazazi-Hyseni (The Oncologist 2010; 15:819-825).*
Kristensen (Clinical Chemistry 2009 55:8 pp. 1471-1783).*
Thon (OncoTargets and Therapy 2013:6 1363-1372).*
Schraml (Oncology Reports 2012:28 654-658).*
Bindra et al., "Hypoxia-Induced Down-regulation of BRCA1 Expression by E2F's," Cancer Research, vol. 65, No. 24, pp. 11597-11604, Dec. 2005.
Booth et al., "Oxidative bisulfite sequencing of 5-methylcytosine and 5-hydroxymethylcytosine," Nature Protocols, vol. 8, No. 10, Sep. 2013.
Esteller et al., "A Gene Hyupermethylation Profile of Human Cancer," Cancer Research, vol. 62, pp. 3225-3229, Apr. 2009.
Esteller et al., "Promoter Hypermethyiation and BRCA1 Inactivation in Sporadic Breast and Ovarian Tumors," Journal of the National Cancer Institute, vol. 92, No. 7, pp. 564-569, Apr. 2000.
Feng et al., "Conservation and divergence of methylation patterning in plants and animals," PNAS, vol. 107, No. 19, pp. 8689-8694, May 2010.
Gupta et al., "Advances i genome-wide DNA methylation analysis," BioTechniques, vol. 49, No. 4, pp. iii-xi, Oct. 2010.
Hao et al., "Reciprocal regulation of the basic helix-loop-helix/Per-Arnt-Sim partner proteins Arnt and Arnt2, during neuronal differentation," Nucleic Acids Research, vol. 41, No. 11, pp. 5626-5638, Apr. 2013.
Holm et al., "Molecular subtypes of breast cancer are associated with characteristic DNA methylation patterns," Breast Cancer Research, vol. 12, R36, 2010.
Ibragimova et al., "Aberrant promoter hypermethyiation of PBRM1, BAP1, SETD2, KDM6A and other chromatin-modifying genes is absent or rare in clear cell RCC," Epigenetics, vol. 8, Issue 5, pp. 486-493, May 2013.
International Search Report for International Application No. PCT/EP2016/054671 dated Jun. 3, 2016.
Kristensen et al., "PCR-Based Methods for Detecting Single-Locus DNA Methylation Biomarkers in Cancer Diagnostics, Prognostics, and Response to Treatment," Clinical Chemistry, vol. 55, No. 8, pp. 1471-1483, 2009.
Lee et al., "Hypoxic silencing of tumor suppressor RUNX3 by histone modification in gastric cancer cells," Oncogene, vol. 28, No. 2, pp. 184-194, Oct. 2008.
Lu et al., "Hypoxia-Induced Epigenetic Regulation and Silencing of the BRCA1 Promoter," Molecular and Cellular Biology, vol. 31, No. 16, pp. 3339-3350, Aug. 2011.
Majchrzak-Celinska et al., "Detection of MGMT, RASSF1A, p15INK4B, and p14ARF promoter methylation in circulating tumor-derived DNA of central nervous system cancer patients," J. App. Genetics, vol. 54, pp. 335-344, May 2013.
Michels, "The promises and challenges of epigenetic epidemiology," Experimental Gerontology, vol. 45, pp. 297-361, 2010.
Peng et al., "Antiangiogenic therapy: a novel approach to overcome tumor hypoxia," Chinese Journal of Cancer, vol. 29, Issue 8, pp. 715-720, Aug. 2010.

(Continued)

*Primary Examiner* — Amanda Haney
(74) *Attorney, Agent, or Firm* — Rouget F. Henschel; Potomac Law Group, PLLC

(57) ABSTRACT

The present application relates to the field of cancer, particular to hypoxic tumors. It was found that hypoxia is an important driver for hypermethylation of (promoters of) tumor suppressor genes. As this hypermethylation is a stable signature that is also present in circulating tumor DNA in peripheral blood, detecting this methylation pattern is a surrogate marker for tumor hypoxia. This can be used to adapt therapy as well.

4 Claims, 23 Drawing Sheets

(56) References Cited

OTHER PUBLICATIONS

Radpour et al., "Hypermethyiation of Tumor Suppressor Genes Involved in Critical Regulatory Pathways for Developing a Blood-Based Test in Breast Cancer," PLoS ONE, vol. 6, Issue 1, p. 316080, Jan. 2011.
Robinson et al., "Hypoxia-induced DNA hypermethyiation in human pulmonary fibroblasts is associated with Thy-1 promoter methylation and the development of a pro-fibrotic phenotype," Respiratory Research, vol. 13, No. 1, p. 74, Aug. 2012.
Roth et al., "p16, MGMT, RARβ2, CLDN3, CRBP, and MT1G gene methylation in esophageal squamous cell carcinoma and its precursor lesions," Oncology Reports, vol. 15, pp. 1591-1597, Jun. 2006.
The Tumor Suppressor Gene Database, https://bioinfo.uth.edu.TSGene1.0, accessed Sep. 12, 2018.
Thienpont et al. "Tumour hypoxia causes DNA hyper-methylaton by reducing TET activity," Nature, vol. 537, pp. 63-68 and Supplement, Sep. 2616.
Watson et al., "Generation of an epigenetic signature by chronic hypoxia in prostate cells," Human Molecular Genetics, vol. 18, No. 19, pp. 3594-3606, Oct. 2009.

\* cited by examiner

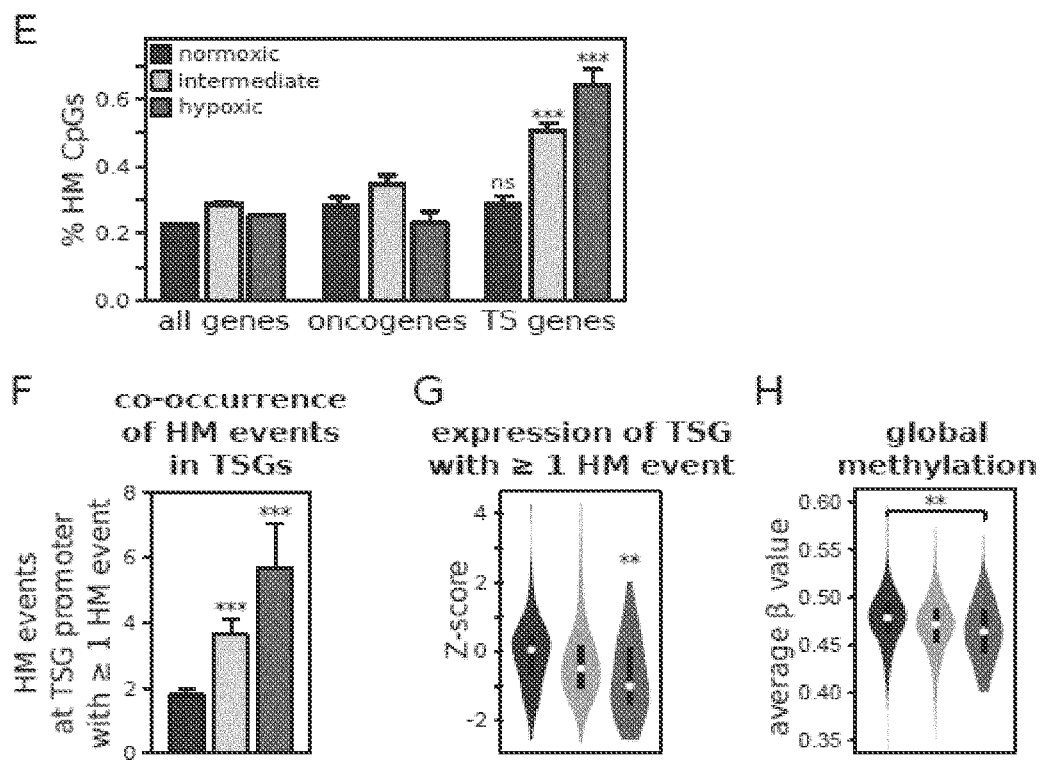

C

D

A

D

MARKERS FOR DETERMINING TUMOR HYPOXIA

FIELD OF THE INVENTION

The present application relates to the field of cancer, particular to hypoxic tumors. It was found that hypoxia is an important driver for hypermethylation of (promoters of) tumor suppressor genes. As this hypermethylation is a stable signature that is also present in circulating tumor DNA in peripheral blood, detecting this methylation pattern is a surrogate marker for tumor hypoxia. This can be used to adapt therapy as well.

BACKGROUND

Most cancers originate from a single cell that starts to behave abnormally due to the acquisition of somatic mutations. The mechanisms underlying these somatic mutations have been extensively studied over the past decade. Apart from genetic changes, tumors are also epigenetically distinct from their tissue of origin. The most established epigenetic alterations are at the level of DNA methylation, but the mechanisms giving rise to them are poorly understood (Esteller, 2008).

DNA methylation changes in tumors involve a genome wide hypomethylation and local hypermethylation of gene promoters (Esteller, 2008). The latter frequently affects tumor suppressor genes (TSGs) such as PTEN, MLH1 and BRCA1, down-regulating their expression and thus contributing to the oncogenic process. How DNA methylation changes arise is heavily debated. An instructive model has been proposed, whereby tumor-associated genetic changes are obligatory to instruct and/or maintain these epigenetic alterations (Struhl, 2014; You and Jones, 2012). For instance, activating mutations in BRAF lead to a global DNA hypermethylation in colorectal cancer (Weisenberger et al. 2006). However, a limitation of this model is that hypermethylation of TSGs, while highly prevalent in cancer, can be explained by somatic mutations in only a fraction of tumors. As a striking example, extensive hypermethylation was found in ependymomas that appeared to be devoid of genetic changes (Mack et al., 2014). It is thus unclear if and which other factors may be instrumental in triggering hypermethylation of TSGs (Oey and Whitelaw, 2014; Struhl, 2014).

In contrast to methylation, the existence of DNA demethylation has remained elusive for many years until recently, when it was discovered that DNA demethylation occurs through the ten-eleven translocation methylcytosine dioxygenases (TET1, TET2 and TET3), which oxidize 5-methyl-cytosine (5mC) to 5-hydroxymethyl-C (5hmC) (Tahiliani et al., 2009). This 5hmC and its further oxidized derivatives act as targets for base-excision repair, and are replaced by an unmodified C to achieve de-methylation (Branco et al., 2012; Pfaffeneder et al., 2014; Shen et al., 2013). Although DNA demethylation, as mediated by TET hydroxylases, has predominantly been studied in the context of embryonic stem cells (ESCs), a number of studies have revealed their importance in cancer (eg, Lian et al., Cell 2012 or Sturm, Cancer Cell 2012). Interestingly, TET enzymes are dioxygenases that need a number of co-factors, such as α-ketoglutarate (Carey, Nature, 2014) and vitamin C (Blashke, Nature 2013), but their activity can also be inhibited by a number of competing metabolites, including 2-oxoglutarate (Figueroa, Cancer Cell 2010), succinate and fumarate (Letouze, Cancer Cell 2013).

Mutations suppressing TET activity, occurring either directly through TET, or indirectly through accumulation of metabolites that suppress TET activity, were frequently described in myeloid leukemia and glioblastoma (Figueroa et al., 2010; Quivoron et al., 2011; Shen et al., 2013; Xiao et al., 2012; Xu et al., 2011). In these tumors, reduced TET activity caused an accumulation of 5mC, and subsequent TSG hypermethylation. Simultaneously, depletion of 5hmC also emerged as an unambiguous hallmark of several other cancers, although insights into the underlying mechanisms are lacking (Yang et al., 2013). The question thus emerges whether cancer epimutations arising through reduced DNA demethylation, are per se genetically encoded, or whether it can also be induced through changes in the tumor microenvironment.

One of the many changes that occur in the tumor microenvironment is oxygen availability. Hypoxia or lack of oxygen, is highly pervasive in solid tumors. As tumors expand, there is an increase in the diffusion distances from the existing vascular supply, resulting in tumor hypoxia and subsequent angiogenesis. Sustained expansion of a tumor mass thus entails tumor cells to undergo multiple rounds of severe hypoxia (Harahan and Folkman, 1996; Harris, 2002). Tumor vessels are moreover functionally and structurally abnormal, leading to pervasive hypoperfusion and a further exacerbation of tumor hypoxia (Jain, 2005). Hypoxia is canonically sensed through the HIF-prolyl-hydroxylase domain proteins (PHDs). Under normoxic conditions, PHDs hydroxylate HIFs thereby targeting them for proteasomal degradation. Under hypoxic conditions PHDs fail to hydroxylate HIFs, leading to HIF stabilization and a hypoxic cellular response (Pugh and Ratcliffe, 2003; Schofield and Ratcliffe, 2004). The hypoxic response is known to induce metastasis that decreases the survival prognoses of a cancer patient significantly (Chang and Erler 2013). It would thus be advantageous to have a cheap, reliable and non-invasive way to identify tumors that are hypoxic, so that the treatment can be adapted to address and alter the hypoxic state.

Although DNA hypermethylation and hypoxia are widely recognized as cancer hallmarks, the impact of hypoxia on TET hydroxylase activity and subsequent DNA (de)methylation has not been assessed. We here unravel a new mechanism in which hypoxia decreases TET hydroxylase activity, leading to an accumulation of 5mC and the acquisition of tumor epimutations.

SUMMARY

As shown herein, tumor hypoxia induces a methylated gene signature in the tumor DNA. This is a stable signature also present in circulating tumor DNA. Thus, this signature, which can be assessed on circulating tumor DNA isolated from peripheral blood of a patient, can be used as a measure for tumor hypoxia.

It is an object of the invention to provide methods of determining tumor hypoxia, comprising:
  Determining the hypermethylation status of one or more promoters of tumor suppressor genes in a sample comprising circulating tumor DNA from a subject;
  Correlating said hypermethylation status to tumor hypoxia.

Typically, increased promoter methylation is indicative of increased hypoxia. An increased DNA methylation level (also known as hypermethylation) can be the result of increased methylation or of a decreased DNA demethylation.

These methods can also be used to monitor response to cancer therapy. According to such methods, the steps are:

Determining the hypermethylation status of one or more promoters of tumor suppressor genes in a sample comprising circulating tumor DNA from a subject receiving cancer therapy;

Correlating said hypermethylation status to tumor hypoxia.

For instance, it is well know that anti-angiogenic therapies (e.g. Avastin) may result in tumor hypoxia when the dose is too high. Indeed, a too high dose of anti-angiogenic therapy results in distorted tumor vessels and less oxygenation. This is bad, as it makes the tumor less accessible for further medication, and may induce metastasis. Thus, when a tumor becomes hypoxic in response to anti-angiogenic therapy, the dose should be decreased, or another drug should be considered.

Alternatively, a patient may receive therapy aimed at vessel normalization (e.g. chloroquine), particularly when the tumor is already hypoxic. In such case, the disappearance of methylation will indicate that the tumor becomes more normoxic, and thus that the therapy is successful. In other words, the methylation status of promoters of tumor suppressor genes is a surrogate marker for tumor hypoxia that can be used as a companion diagnostic for cancer therapy.

Accordingly, methods as described herein are provided that further comprise a step of adapting the dose or nature of cancer therapy to the level of tumor hypoxia.

According to particular embodiments, the tumor is breast cancer.

According to a further aspect, kits are provided for the detection of tumor hypoxia. These kits will comprise means, typically primers or probes, to detect hypermethylation of promoters of tumor suppressor genes. Particularly, to detect this in a sample of circulating tumor DNA isolated from a patient.

According to particular embodiments, the tumor suppressor genes are one or more selected from HIC1, KDM6A, NF2, KDM5C, IGFBP2, ARNT2, PTEN, MGMT, ATM, MLH1, BRCA1, SEMA3B, TIMP3, THBD, and CLDN3.

DETAILED DESCRIPTION

Definitions

Figure 1:
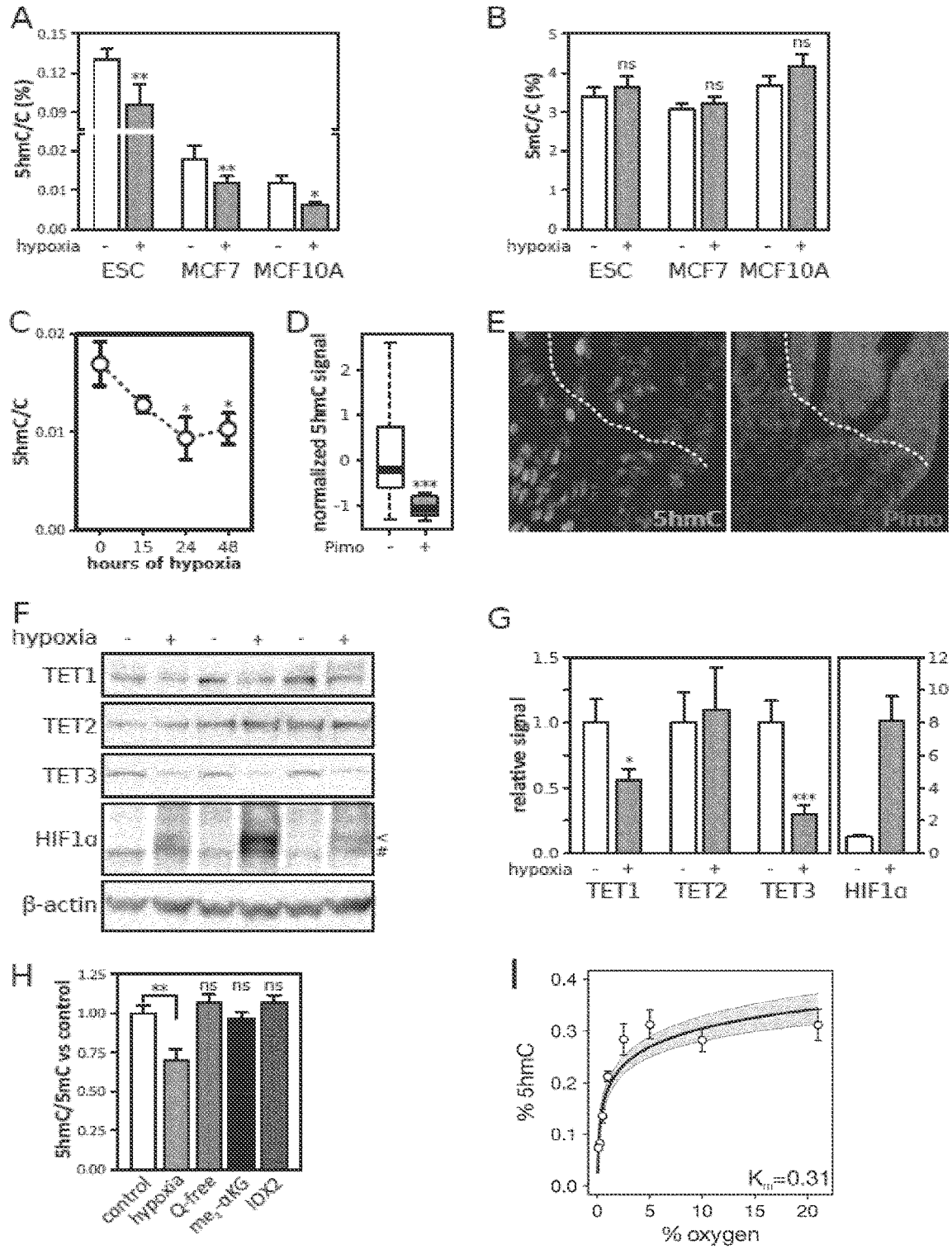
FIG. 1: Effect of hypoxia on 5hmC levels. A-B LC/MS analysis of global 5hmC (A) and 5mC (B) levels in DNA from mouse ES cells, MCF7 cells and MCF10A cells grown for 24 hours under normoxic (21% O2) and hypoxic (0.5% O2) conditions. C LC/MS analysis of global DNA 5hmC levels in MCF7 cells after different exposure times to hypoxia (0.5% O2). D Quantification of the relative 5hmC signal in pimonidazole-positive and pimonidazole-negative areas. E Immunofluorescence staining of 5hmC (red) and hypoxic areas marked by pimonidazole adducts (green) in a human tumor grafted in a nude mouse. F Western blot analysis of changes in TET1, TET2, TET3, HIF1α and β-actin protein levels in response to hypoxia. #: non-specific band; <: specific band. G Quantification of changes in Western blot band intensity relative to normoxic samples, normalized to β-actin levels. H LC/MS analysis of global 5hmC levels in MCF7 cells grown for 24 hours under normoxic, hypoxic or glutamine-free (Q-free) conditions, or supplemented with dimethyl-α-ketoglutarate or IOX2. Bars in a, d and e represent the mean±s.e.m. of at least 5 biological replicates. I Michaelis-Menten curve of Tet1 for $O_2$ concentration. Genomic DNA from TET-triple-knockout cells was exposed for 3 minutes to purified Tet1 enzyme, and quantified for its 5hmC content using ELISA. Grey area represent the 95% confidence interval of the logarithmic curve. Error bars in all panels represent the s.e.m. of 5 replicate experiments. Asterisks indicate P-values of paired t-tests (*P<0.05, P<0.01, *P<0.001).

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Epimutations, such as hypermethylation of tumor suppressor gene (TSG) promoters, confer growth advantages to cancer cells, but how they arise is poorly understood. Here, we describe how tumor hypoxia reduces the activity of oxygen-dependent TET enzymes, which catalyze DNA demethylation through hydroxylation of 5-methylcytosine. This occurs independently of alterations in gene expression, basal metabolism, HIF activity or nuclear reactive oxygen species, and increases hypermethylation specifically at gene promoters in vitro. As a consequence, hypoxic human tumors acquire more epimutations than their normoxic counterparts, especially in TSGs promoters. Likewise, spontaneous murine breast tumors acquire more epimutations in TSG promoters when rendered hypoxic whereas increased tumor oxygenation rescues this hypermethylation. Tumor hypoxia thus acts as a novel regulator underlying epimutagenesis. We provide extensive evidence that TETs also require oxygen as a co-factor necessary for their activity. In particular, we show that hypoxia reduces hydroxymethylation in cell lines (e.g. murine ESCs, MCF10A premalignant mammary cells, the MCF7 breast cancer cell line, human alveolar basal epithelial cells, non-small cell lung carcinoma, neuroblastoma cell lines). Notably, the reduction in DNA hydroxymethylation dose-dependently increased with increasing timing of hypoxia, and did not depend on HIF activity, gene expression changes of TETs or metabolic alterations of their co-factors. Moreover, using patient-derived xenografts and spontaneously arising mouse tumors, we show that only those regions with a poorly organized tumor vasculature, resulting in areas of pronounced tumor hypoxia, are characterized by a remarkable loss of DNA hydroxymethylation. We thus provide evidence that variability within the tumor microenvironment contributes to epigenetic heterogeneity and noise, thereby allowing clonal evolution of the tumor, a recent notion that is gaining traction in cancer research (Swanton and Beck, 2014). Interestingly, hypoxia reduced hydroxymethylation mainly at gene promoters, subsequently translating into increased methylation of gene promoters. In human tumors, these epimutations were selected for, as hypoxic breast and glioblastoma tumors were markedly enriched for epimutations compared to normoxic tumors, and mainly affected tumor suppressor genes (eg, anti-apoptotic and DNA repair genes, as well as anti-metastatic and anti-angiogenic factors). Notably, hypermethylation of tumor suppressor genes occurred against a background of global hypomethylation, which was mediated by reduced expression of DNA methyltransferases under hypoxia. Finally, by manipulating tumor oxygenation in the PyMT breast cancer model, we also demonstrate that vessel pruning induced by delivery of the anti-angiogenic sFlk1, and the concomitant increase in hypoxia, exacerbate the hypermethylation phenotype, whereas vessel normalisation obtained by intercrossing PyMT mice with PhD2 heterozygous-deficient mice, and the concomitantly reduction in hypoxia, have the opposite effect. As a consequence, our results not only provide for the first time a mechanism of how the tumor microenvironment may dictate methylation events in tumors, they also suggest that normalising the tumor vasculature may exert some of its therapeutic benefits though modulating the tumor epigenome.

In a first embodiment, the invention provides a method of determining tumor hypoxia, comprising determining the hypermethylation status of one or more promoters of tumor suppressor genes in a sample comprising circulating tumor DNA from a subject; and comparing the said hypermethylation status to a threshold value indicative to tumor hypoxia. The said threshold value indicative to tumor hypoxia is a methylation status of at least 3%, 4%, 5%, 6%, 7%, 8%, 9%, 10%, 15% higher than the methylation status of a normoxic tissue. In another embodiment, the invention provides a method of determining tumor hypoxia, comprising determining the hypermethylation status of one or more promoters of tumor suppressor genes in a sample comprising circulating tumor DNA from a subject; and comparing the said hypermethylation status to a threshold value indicative to tumor hypoxia, wherein increased promoter methylation is indicative of increased tumor hypoxia. The said threshold value indicative to tumor hypoxia is a methylation status of at least 3%, 4%, 5%, 6%, 7%, 8%, 9%, 10%, 15% higher than the methylation status of a normoxic tissue. In another embodiment, the invention provides a method of determining tumor hypoxia, comprising determining the hypermethylation status of one or more promoters of tumor suppressor genes in a sample comprising circulating tumor DNA from a subject; and comparing the said hypermethylation status to a threshold value indicative to tumor hypoxia, wherein decreased promoter demethylation is indicative of increased tumor hypoxia. The said threshold value indicative to tumor hypoxia is a methylation status of at least 3%, 4%, 5%, 6%, 7%, 8%, 9%, 10%, 15% higher than the methylation status of a normoxic tissue. In another embodiment, the invention provides a method of determining tumor hypoxia, comprising determining the demethylation status of one or more promoters of tumor suppressor genes in a sample comprising circulating tumor DNA from a subject; and comparing the said methylation status to a threshold value indicative to tumor hypoxia, wherein decreased promoter demethylation is indicative of increase tumor hypoxia. The said threshold value indicative to tumor hypoxia is a methylation status of at least 3%, 4%, 5%, 6%, 7%, 8%, 9%, 10%, 15% higher than the methylation status of a normoxic tissue.

In another embodiment, the invention provides a method of determining tumor hypoxia, comprising determining the hypermethylation status of one or more promoters of tumor suppressor genes in a sample comprising circulating tumor DNA from a subject; and comparing the said hypermethylation status to a methylation status of a normoxic tissue wherein a hypermethylation status is present when the methylation status is at least 3%, 4%, 5%, 6%, 7%, 8%, 9%, 10%, 15% higher compared to said normoxic tissue. In a preferred embodiment, increased promoter methylation is indicative of increased hypoxia. In another embodiment, the invention provides a method of determining tumor hypoxia, comprising determining the demethylation status of one or more promoters of tumor suppressor genes in a sample comprising circulating tumor DNA from a subject; and comparing the said demethylation status to a methylation status of a normoxic tissue wherein a demethylation status is present when the methylation status is at least 3%, 4%, 5%, 6%, 7%, 8%, 9%, 10%, 15% lower compared to said normoxic tissue. In a preferred embodiment, decreased promoter demethylation is indicative of increased hypoxia.

The term "tumor hypoxia" used herein refers to the situation where tumor cells have been deprived of oxygen. Hypoxia is highly pervasive in solid tumors, with O2 levels ranging from 5% to near anoxia, and about a third of tumor areas being below 0.5% (Vaupel et al 2007). As tumors expand, there is an increase in the diffusion distances from the existing vascular supply, resulting in tumor hypoxia and subsequent angiogenesis. Sustained expansion of a tumor mass thus entails tumor cells to undergo multiple rounds of severe hypoxia (Hanahan and Folkman, 1996; Harris, 2002). Hypoxia is also known to induce metastasis that decreases the survival prognoses of a cancer patient significantly (Chang and Erler 2013). In this application hypoxia refers to tumor hypoxia. In this application the term normoxic is used for cell cultures at 5% CO2 and an oxygen concentration between 5% and atmospheric concentration. To render cultures hypoxic, they were incubated in an atmosphere of 0.5% oxygen, 5% CO2 and 94.5% N2. Exposure to hypoxia can be verified by using HIF1α protein stabilization and/or the induction of hypoxia marker genes.

The term "methylation status" used herein refers to the level of methylation of DNA. DNA methylation is a process by which methyl groups are added to DNA. Demethylation is the chemical process resulting in the removal of a methyl group (CH3) from a DNA-molecule. Decreased promoter demethylation refers to an increase in methylation status of preferably at least 3%, 4%, 5%, 6%, 7%, 8%, 9%, 10%, 15% compared to a control situation. Hypermethylation refers to an increase in the methylation of DNA compared to a control situation. Preferably, the increase in methylation would at least be 3%, 4%, 5%, 6%, 7%, 8%, 9%, 10%, 15%, 20% compared to a control situation. The term "hypermethylation status" refers to the level of hypermethylation of DNA. In this application hypermethylation of individual CpGs at gene promoters in individual tumors was assessed as follows: all β-values were transformed to M-values (Du et al 2010) using $M=\log 2(\beta/(1-\beta))$. The mean $\mu$ and standard deviation $\sigma$ of the M value across all control (normoxic) tumors was next calculated for each CpG, and used to assign Z-values to each CpG in each tumor using $Z=(M-\mu)/\sigma$, describing the normal variation in methylation for that probe. CpGs for which the Z-value exceeded 5.6 (i.e. the mean plus 5.6 times the standard deviation, or a Bonferroni-adjusted P-value of 0.01) were called as hypermethylated in that tumor. This analysis was preferred over Wilcoxon-based models that assess differences in the average methylation level between subgroups, as the latter does not enable the identification or quantification of more rare HM events in individual CpGs and tumors. The CpG sites are regions of DNA where a cytosine nucleotide is followed by a guanine nucleotide in the linear sequence of bases along its 5'→3' direction. CpG is shorthand for 5'-C-phosphate-G-3', that is, cytosine and guanine separated by only one phosphate; phosphate links any two nucleosides together in DNA. The CpG notation is used to distinguish this single-stranded linear sequence from the CG base-pairing of cytosine and guanine for double-stranded sequences. The CpG notation is therefore to be interpreted as the cytosine being 5 prime to the guanine base. CpG should not be confused with GpC, the latter meaning that a guanine is followed by a cytosine in the 5'→3' direction of a single-stranded sequence.

In the present invention a "promoter" is a nucleotide sequence that comprises regulatory elements, which mediate the expression of a nucleic acid molecule. A "tumor suppressor gene" is a gene that protects a cell from one step on the path to cancer. When this gene mutates or undergoes epigenetic changes to cause a loss or reduction in its function, the cell can progress to cancer, usually in combination with other genetic changes.

In yet another embodiment, the invention provides a method to monitor response to cancer therapy, comprising:
Determining the hypermethylation status of one or more promoters of tumor suppressor genes in a sample comprising circulating tumor DNA from a subject receiving cancer therapy;
Comparing the said hypermethylation status to a threshold value indicative to tumor hypoxia, wherein the said threshold value indicative to tumor hypoxia is a methylation status of at least 3%, 4%, 5%, 6%, 7%, 8%, 9%, 10%, 15% higher than the methylation status of a normoxic tissue.

In yet another embodiment, the invention provides a method to monitor response to cancer therapy, comprising:
Determining the hypermethylation status of one or more promoters of tumor suppressor genes in a sample comprising circulating tumor DNA from a subject receiving cancer therapy;
Comparing the said hypermethylation status to a methylation status of a normoxic tissue wherein a hypermethylation status is present when the methylation status is at least 3%, 4%, 5%, 6%, 7%, 8%, 9%, 10%, 15% higher compared to said normoxic tissue.

In yet another embodiment, the invention provides a method to monitor response to cancer therapy, comprising:
Determining the hypermethylation status of one or more promoters of tumor suppressor genes in a sample comprising circulating tumor DNA from a subject receiving cancer therapy;
Comparing the said hypermethylation status to a threshold value indicative to tumor hypoxia, wherein the said threshold value indicative to tumor hypoxia is a methylation status of at least 3%, 4%, 5%, 6%, 7%, 8%, 9%, 10%, 15% higher than the methylation status of a normoxic tissue;
Adapting the dose or nature of cancer therapy to the level of tumor hypoxia.

In yet another embodiment, the invention provides a method to monitor response to cancer therapy, comprising:
Determining the hypermethylation status of one or more promoters of tumor suppressor genes in a sample comprising circulating tumor DNA from a subject receiving cancer therapy;
Comparing the said hypermethylation status to a methylation status of a normoxic tissue wherein a hypermethylation status is present when the methylation status is at least 3%, 4%, 5%, 6%, 7%, 8%, 9%, 10%, 15% higher compared to said normoxic tissue.
Adapting the dose or nature of cancer therapy to the level of tumor hypoxia.

In yet another embodiment, the invention provides a method to monitor response to cancer therapy, comprising:
Determining the demethylation status of one or more promoters of tumor suppressor genes in a sample comprising circulating tumor DNA from a subject receiving cancer therapy;
Comparing the said demethylation status to a threshold value indicative to tumor hypoxia, wherein the said threshold value indicative to tumor hypoxia is a demethylation status of at least 3%, 4%, 5%, 6%, 7%, 8%, 9%, 10%, 15% lower than the methylation status of a normoxic tissue.

In yet another embodiment, the invention provides a method to monitor response to cancer therapy, comprising:
Determining the demethylation status of one or more promoters of tumor suppressor genes in a sample comprising circulating tumor DNA from a subject receiving cancer therapy;
Comparing the said demethylation status to a methylation status of a normoxic tissue wherein a demethylation status is present when the methylation status is at least 3%, 4%, 5%, 6%, 7%, 8%, 9%, 10%, 15% lower compared to said normoxic tissue.

In yet another embodiment, the invention provides a method to monitor response to cancer therapy, comprising:
Determining the demethylation status of one or more promoters of tumor suppressor genes in a sample comprising circulating tumor DNA from a subject receiving cancer therapy;
Comparing the said demethylation status to a threshold value indicative to tumor hypoxia, wherein the said threshold value indicative to tumor hypoxia is a demethylation status of at least 3%, 4%, 5%, 6%, 7%, 8%, 9%, 10%, 15% lower than the methylation status of a normoxic tissue;
Adapting the dose or nature of cancer therapy to the level of tumor hypoxia.

In yet another embodiment, the invention provides a method to monitor response to cancer therapy, comprising:
Determining the demethylation status of one or more promoters of tumor suppressor genes in a sample comprising circulating tumor DNA from a subject receiving cancer therapy;
Comparing the said demethylation status to a methylation status of a normoxic tissue wherein a demethylation status is present when the methylation status is at least 3%, 4%, 5%, 6%, 7%, 8%, 9%, 10%, 15% lower compared to said normoxic tissue.
Adapting the dose or nature of cancer therapy to the level of tumor hypoxia.

In yet another embodiment, the invention provides a method to adapt the dose or nature of cancer therapy, comprising:
Determining the hypermethylation status of one or more promoters of tumor suppressor genes in a sample comprising circulating tumor DNA from a subject receiving cancer therapy;
Comparing the said hypermethylation status to a threshold value indicative to tumor hypoxia, wherein the said threshold value indicative to tumor hypoxia is a methylation status of at least 3%, 4%, 5%, 6%, 7%, 8%, 9%, 10%, 15% higher than the methylation status of a normoxic tissue;
Adapting the dose or nature of cancer therapy to the level of tumor hypoxia.

In yet another embodiment, the invention provides a method to adapt the dose or nature of cancer therapy, comprising:
Determining the hypermethylation status of one or more promoters of tumor suppressor genes in a sample comprising circulating tumor DNA from a subject receiving cancer therapy;
Comparing the said hypermethylation status to a methylation status of a normoxic tissue wherein a hypermethylation status is present when the methylation status is at least 3%, 4%, 5%, 6%, 7%, 8%, 9%, 10%, 15% higher compared to said normoxic tissue.
Adapting the dose or nature of cancer therapy to the level of tumor hypoxia.

In yet another embodiment, the invention provides a method to adapt the dose or nature of cancer therapy, comprising:
Determining the demethylation status of one or more promoters of tumor suppressor genes in a sample comprising circulating tumor DNA from a subject receiving cancer therapy;
Comparing the said demethylation status to a threshold value indicative to tumor hypoxia, wherein the said threshold value indicative to tumor hypoxia is a demethylation status of at least 3%, 4%, 5%, 6%, 7%, 8%, 9%, 10%, 15% lower than the methylation status of a normoxic tissue;

Adapting the dose or nature of cancer therapy to the level of tumor hypoxia.

In yet another embodiment, the invention provides a method to adapt the dose or nature of cancer therapy, comprising:

Determining the demethylation status of one or more promoters of tumor suppressor genes in a sample comprising circulating tumor DNA from a subject receiving cancer therapy;

Comparing the said demethylation status to a methylation status of a normoxic tissue wherein a demethylation status is present when the methylation status is at least 3%, 4%, 5%, 6%, 7%, 8%, 9%, 10%, 15% lower compared to said normoxic tissue.

Adapting the dose or nature of cancer therapy to the level of tumor hypoxia.

In another embodiment, the invention provides a method to treat a cancer patient, comprising:

Determining the hypermethylation status of one or more promoters of tumor suppressor genes in a sample comprising circulating tumor DNA from a subject receiving cancer therapy;

Comparing the said hypermethylation status to a threshold value indicative to tumor hypoxia, wherein the said threshold value indicative to tumor hypoxia is a methylation status of at least 3%, 4%, 5%, 6%, 7%, 8%, 9%, 10%, 15% higher than the methylation status of a normoxic tissue;

Adapting the dose or nature of cancer therapy to the level of tumor hypoxia

In another embodiment, the invention provides a method to treat a cancer patient, comprising:

Determining the demethylation status of one or more promoters of tumor suppressor genes in a sample comprising circulating tumor DNA from a subject receiving cancer therapy;

Comparing the said demethylation status to a threshold value indicative to tumor hypoxia, wherein the said threshold value indicative to tumor hypoxia is a demethylation status of at least 3%, 4%, 5%, 6%, 7%, 8%, 9%, 10%, 15% lower than the methylation status of a normoxic tissue;

Adapting the dose or nature of cancer therapy to the level of tumor hypoxia

In another embodiment, the invention provides a method to treat a cancer patient, comprising:

Determining the hypermethylation status of one or more promoters of tumor suppressor genes in a sample comprising circulating tumor DNA from a subject receiving cancer therapy;

Comparing the said hypermethylation status to a methylation status of a normoxic tissue wherein a hypermethylation status is present when the methylation status is at least 3%, 4%, 5%, 6%, 7%, 8%, 9%, 10%, 15% higher compared to said normoxic tissue.

Adapting the dose or nature of cancer therapy to the level of tumor hypoxia

In another embodiment, the invention provides a method to treat a cancer patient, comprising:

Determining the demethylation status of one or more promoters of tumor suppressor genes in a sample comprising circulating tumor DNA from a subject receiving cancer therapy;

Comparing the said demethylation status to a methylation status of a normoxic tissue wherein a demethylation status is present when the methylation status is at least 3%, 4%, 5%, 6%, 7%, 8%, 9%, 10%, 15% lower compared to said normoxic tissue.

Adapting the dose or nature of cancer therapy to the level of tumor hypoxia

In another embodiment, the invention provides a kit for the detection of tumor hypoxia, comprising primers or probes to detect hypermethylation of promoters of tumor suppressor genes. In yet another embodiment, the invention provides a kit for the detection of tumor hypoxia, comprising primers or probes to detect demethylation of promoters of tumor suppressor genes. In a preferred embodiment, the said tumor suppressor genes are one or more selected from HIC1 (Hypermethylated in cancer 1), KDM6A (Lysine (K)-specific Demethylase 6A), NF2 (Neurofibromatosis 2), KDM5C (Lysine (K)-specific Demethylase 5C), IGFBP2 (Insulin-like growth factor binding protein 2), ARNT2 (Aryl-hydrocarbon receptor nuclear translocator 2), PTEN (Phosphatase and tensin homolog) MGMT (O-6-Methylguanine-DNA Methyltransferase), ATM (Ataxia telangiectasia mutated), MLH1 (MutL homolog 1), BRCA1 (Breast Cancer 1), SEMA3B (Semaphorin 3B), TIMP3 (TIMP metallopeptidase inhibitor 3), THBD (Thrombomodulin), and CLDN3 (CLaudin 3).

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

Impact of Hypoxia on DNA Hydroxymethylation Activity

To test whether TET hydroxylases are, like PHDs, sensitive to oxygen tension, mouse embryonic stem cells, normal human mammary epithelial cells (MCF10A) and human breast cancer cells (MCF7) were grown for 24 hours at normoxia and hypoxia (0.5% O2), after which their DNA was profiled for nucleotide composition using LC/MS. This demonstrated a significant loss of 5hmC in all 3 cell lines (FIG. 1A). No significant changes in global 5mC levels were detected (FIG. 1B). This effect of hypoxia was time-dependent, as a time course in MCF7 cells revealed a 20% reduction in 5hmC levels after 15 hours, and a further reduction to 33% after 24 and 48 hours (FIG. 1C). As they progress, tumors go through multiple rounds of hypoxia. We therefore assessed whether this reduction in 5hmC was also present physiologically, in hypoxic areas of tumors. A patient tumor was grafted in nude mice, and after 3 weeks of tumor growth, mice were injected with the hypoxia marker pimonidazole. Tumors were harvested and sections stained for pimonidazole adducts and 5hmC. This revealed a significant decrease in 5hmC specifically in hypoxic areas, indicating that hypoxia within the tumor microenvironment can trigger epigenetic tumor heterogeneity (FIG. 1D-E).

Example 2

Changes Secondary to Hypoxia do not Affect DNA Hydroxymethylation

Figure 8:
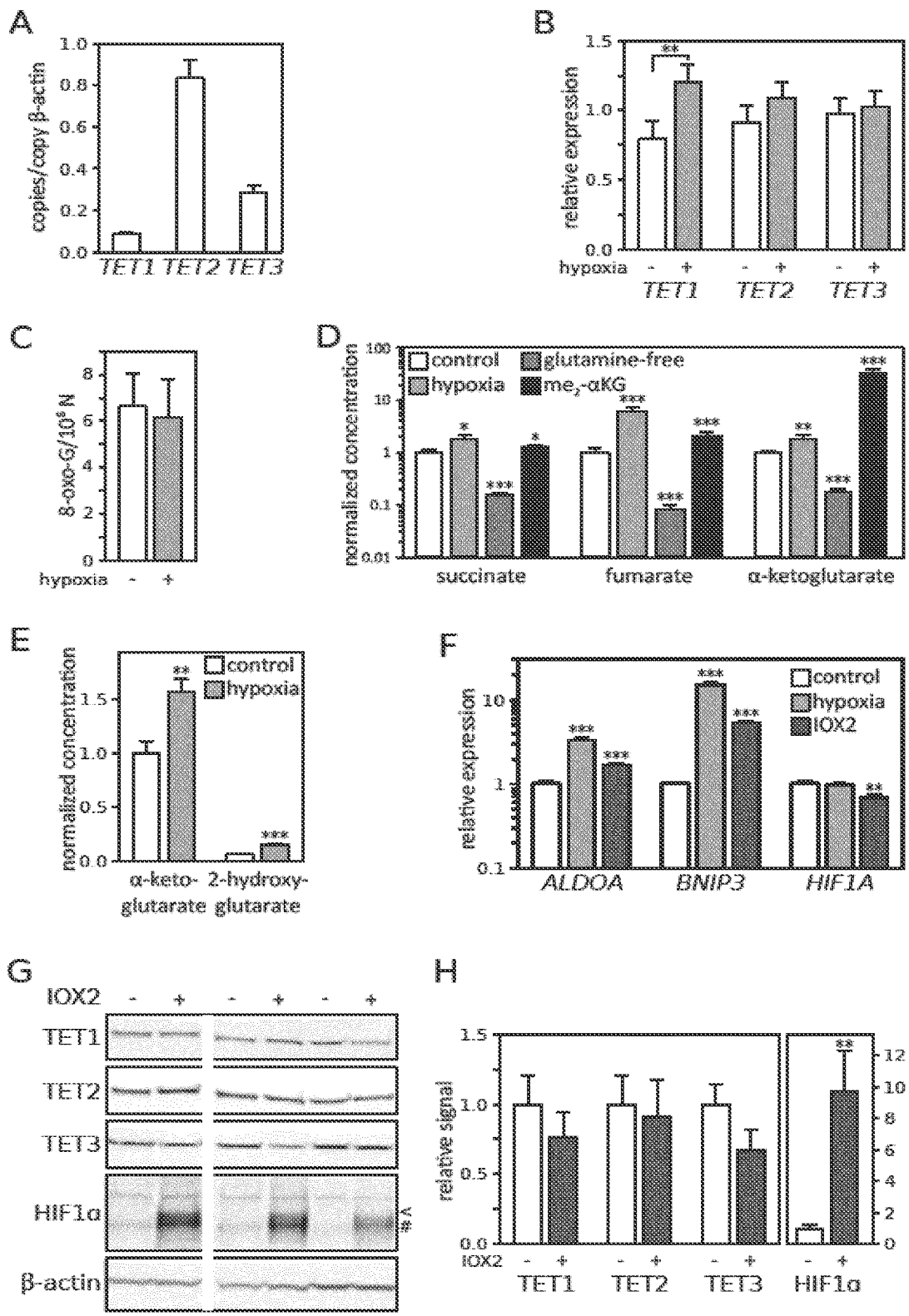
FIG. 8: Factors potentially impacting TET activity in MCF7 cells. A Number of TFT mRNA copies relative to the number β-actin mRNA copies. B RT-qPCR analysis of changes in TET mRNA expression in response to hypoxia. C LC/MS quantification of 8-oxo-guanine levels in DNA from hypoxic and normoxic MCF7 cells. D GC/MS quantification of changes in succinate, fumarate and α-ketoglutarate levels in cells grown under normoxic, hypoxic, glutamine-free and dimethyl-α-ketoglutarate-supplemented conditions. E GC/MS quantification of α-ketoglutarate and 2-hydroxyglutarate levels under normoxic and hypoxic conditions F RT-qPCR analysis of the relative expression of ALDOA, BNIP3 and HIF1a in response to hypoxia and IOX2 treatment. Western blot analysis of changes in HIF1α and β-actin protein levels in response to IOX2 treatment. H Quantification of changes in HIF1α Western blot band intensity relative to carrier-treated samples, normalized to β-actin levels. Bars represent the mean±s.e.m. of at least 4 biological replicates.
Figure 9:
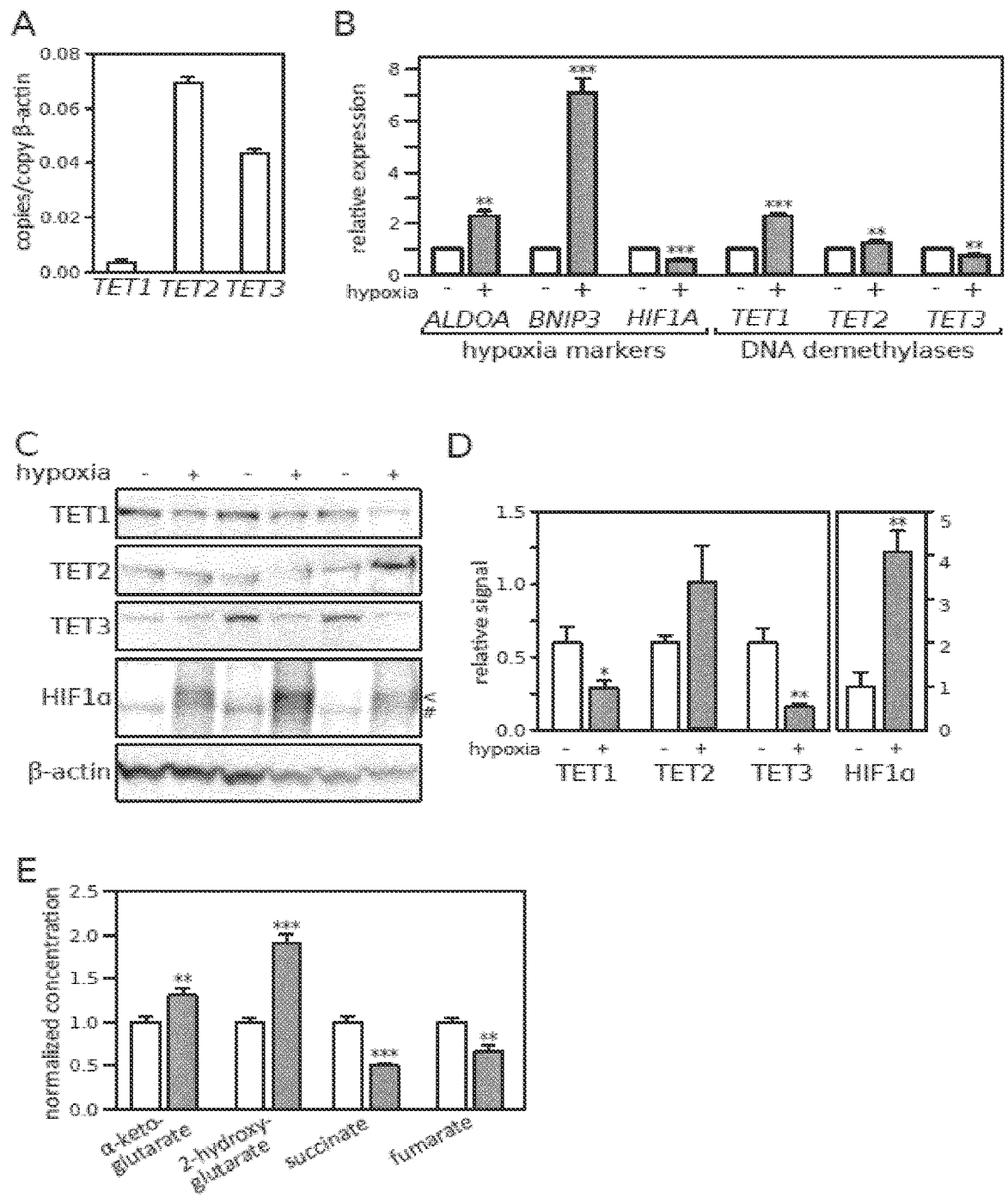
FIG. 9: Cellular changes upon hypoxia in MCF10A cells. A Number of TET mRNA copies relative to the number β-actin mRNA copies. B RT-qPCR analysis of changes in hypoxia marker gene and TET mRNA expression in response to hypoxia. C Western blot analysis of changes in TET, HIF1α and β-actin protein levels in response to 24 hours of hypoxia. D Quantification of changes in HIF1α Western blot band intensity relative to carrier-treated samples, normalized to β-actin levels. E GC/MS quantification of changes in succinate, fumarate and α-ketoglutarate levels in cells grown under normoxic or hypoxic conditions. Bars represent the mean±s.e.m. of at least 4 biological replicates.
Figure 10:
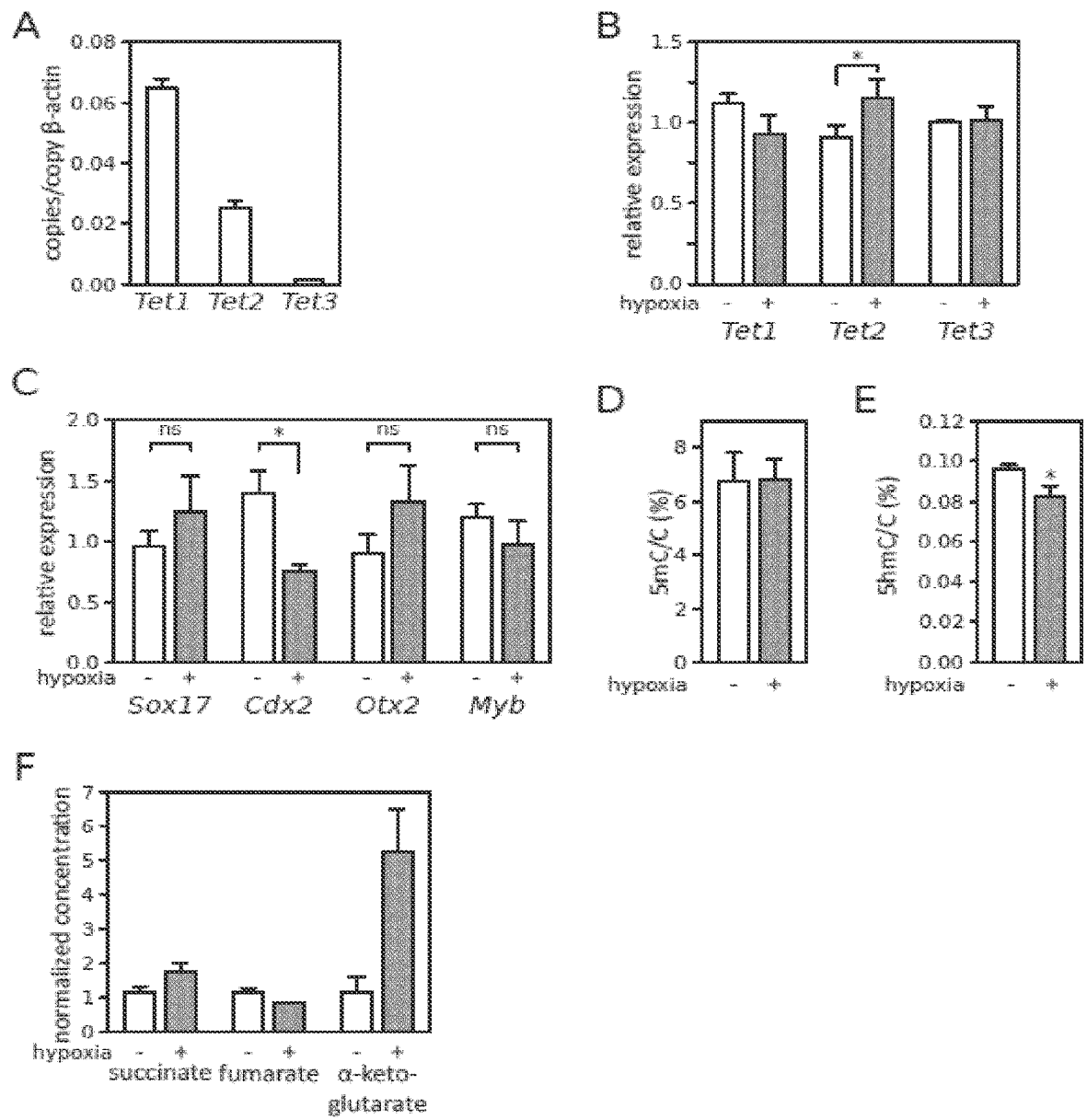
FIG. 10: Factors potentially impacting Tet activity in mouse ES cells. A Number of Tet mRNA copies relative to the number β-actin mRNA copies. B RT-qPCR analysis of changes in Tet mRNA expression in response to hypoxia. C RT-qPCR analysis of the relative expression of a panel of differentiation marker genes. D, E LC/MS analysis of global 5mC (D) and 5hmC (E) levels in DNA from TET1-genetrap mouse ES cells. F GC/MS quantification of changes in succinate, fumarate and α-ketoglutarate levels in cells grown under normoxic and hypoxic conditions. Bars represent the mean±s.e.m. of at least 4 biological replicates.

Similar to PHDs, TET activity has previously been shown to be affected by a variety of cellular changes, including changes in TET expression, in reactive oxygen species (ROS) and in Krebs cycle metabolites (Majmundar et al., 2010; Xiao et al., 2012; Zhao et al., 2013). Since some of these changes have been described to also occur secondary to hypoxia, we investigated whether they might underlie the decrease in 5hmC. Firstly, when assessing TET expression in MCF7 and MCF10A cells, TET2 was the most highly expressed paralogue, with TET3 being 2 to 3 times less abundant and TET1 9 to 16 times less abundant (FIGS. 8A and 9A). Under hypoxic conditions, the dominantly expressed DNA hydroxylase, TET2, was unaffected, whereas TET1 and TET3 protein levels were downregulated in MCF7 and MCF10A cells (FIGS. 1F, 8B and 9B-D). To further assess the impact of changes in TET expression, we studied TET1-deficient ES cells (Yamaguchi et al., 2012). As TET3 is very lowly expressed in ES cells (FIG. 10A) (Koh et al., 2011), TET2 is the sole DNA hydroxylase in these cells. Interestingly, although hypoxia does not decrease TET2 expression or induce cell differentiation in ES cells (FIGS. 10B-C), 5hmC levels were still significantly reduced (FIGS. 10D-E). Taken together, these results indicate that TET expression differences are unlikely to underlie 5hmC loss upon hypoxia. Secondly, increased reactive oxygen species (ROS) in the nucleus are known to affect TET activity, through inactivation of Fe2+ in the TET catalytic domain (Zhao et al., 2013). To assess nuclear ROS, global DNA oxidation (8-oxo-G) was quantified (Pelicano et al., 2004). Levels were however comparable between DNA from hypoxic and normoxic cells, ruling out effects of increased nuclear ROS on TET activity (FIG. 8C). Thirdly, changes in metabolites such as succinate and fumarate are known to affect TET function by competing with its cofactor αKG (Xiao et al., 2012). However, only in hypoxic MCF7 cells, but not in MCF10A or ES cells, these metabolites increased by 3-4 fold (FIGS. 8D, 9E and 10F). Moreover, these cells are wild-type for fumarate hydratase (FH) and succinate dehydrogenase A (SDHA), further confirming that succinate and fumarate concentrations are within the physiological range. To nevertheless assess whether they affect DNA hydroxylation, MCF7 cells were cultured in glutamine-free medium to decrease, and with exogenously added αKG to increase their concentrations (FIG. 8D). Neither of these conditions however altered 5hmC levels (FIG. 1H). Lastly, the concentration of the onco-metabolite 2-hydroxy-glutarate also increased in MCF7 cells in response to hypoxia, but was only present at concentrations of ~5-10% of αKG (FIG. 8E), consistent with the wild-type genotype of MCF7 cells for the anabolising enzyme IDH. Given the similar affinity of αKG and its competitive inhibitor 2-hydroxyglutarate for hydroxylases (Koivunen et al., 2012), also these changes are unlikely to affect TET activity. Combined, these results rule out hypoxia-associated metabolic alterations as underlying the decrease in TET activity. Finally, to evaluate changes through the canonical hypoxia-induced pathway, i.e. HIF activation, we pharmacologically inactivated PHDs by applying IOX2, a recently developed small molecule displaying high specificity for PHDs over other αKG-dependent dioxygenases (Chowdhury et al., 2013). Although this application was sufficient to stabilize HIFs and activate the hypoxia response program (FIGS. 8F-H), no changes in 5hmC ensued (FIG. 1H). Together, these data indicate that in cells under hypoxia, reduced oxygen tension diminishes the oxidative activity of TET enzymes to decrease 5hmC levels independently of HIF activation, metabolic alterations, nuclear ROS or TET expression changes.

Example 3

Genomic Loci Displaying Differential DNA Hydromethylation Under Hypoxia

Figure 2:
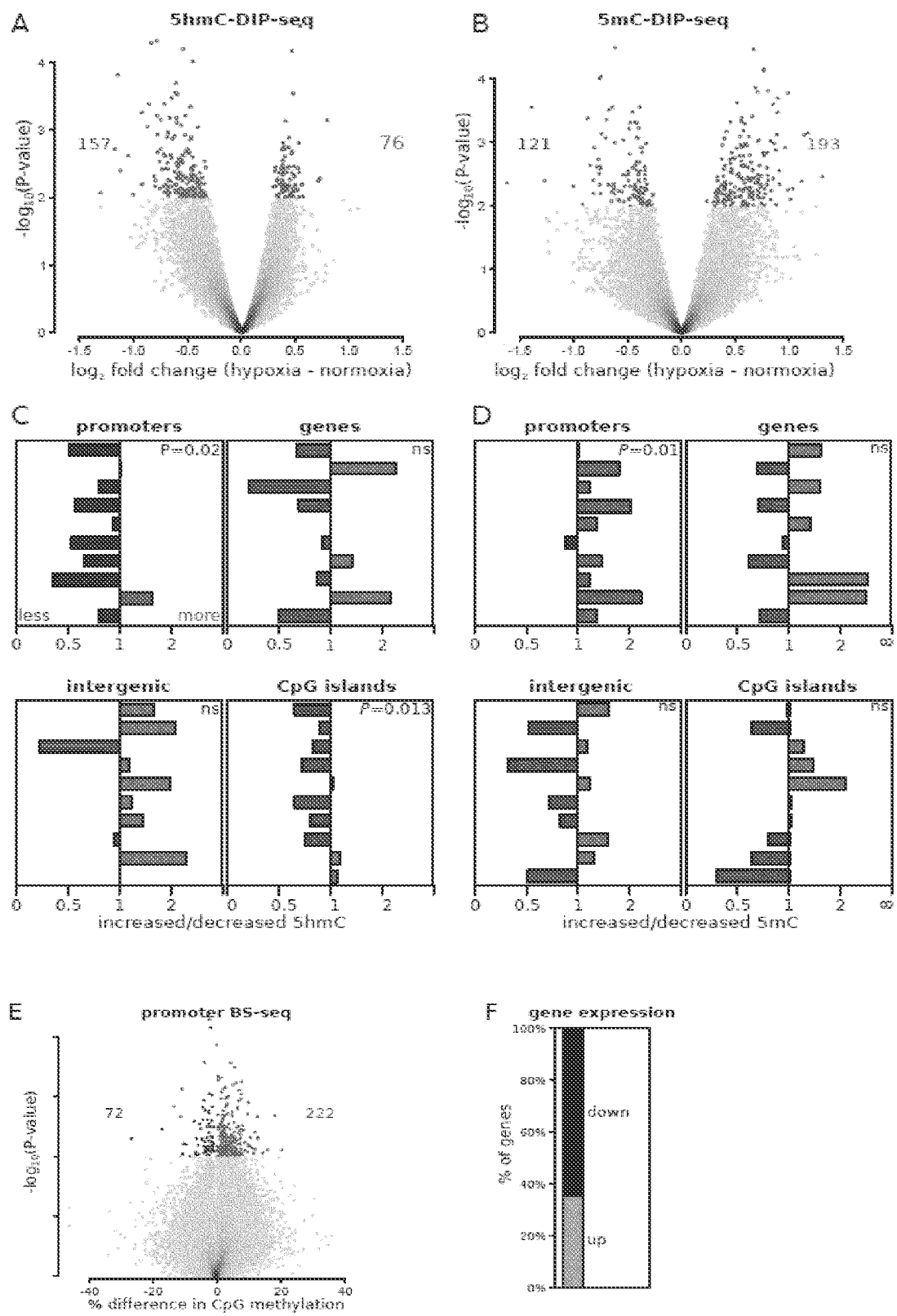
FIG. 2: Genome-wide profiling of 5hmC and 5mC levels in response to hypoxia. A-D MCF7 cells were grown for 24 hours under hypoxic and normoxic conditions. DNA was extracted and subjected to 5hmC-(A,C) and 5mC-(B,D) DIP-seq. (A,B) Volcano plot of a representative experiment displaying the number of promoters gaining (red, right) or loosing (blue, left) 5(h)mC in response to hypoxia. (C,D) Ratio of the number of promoters gaining versus losing 5(h)mC in response to hypoxia, analysed in 4 independent replicate experiments and 6 pair-wise combinations thereof. Lower panels summarize the same for genes, intergenic regions and CpG islands. E Volcano plot of DNA methylation as assessed by the bisulfite sequencing of gene promoters, capture-selected using SeqCapEpi probes. F Fraction of 222 hypermethylated genes identified by bisulfite sequencing that are up- or downregulated.

To analyze where in the genome these changes occurred, DNA from hypoxic and normoxic MCF7 cells was immunoprecipitated using antibodies targeting 5mC and 5hmC, and subjected to high-throughput sequencing (DIPseq, FIG. 2A-B). We initially focused our analyses on gene promoters, as they are most frequently hypermethylated in cancer, and as transcription start sites are among the main sites of action of the TETs (Branco et al., 2012). In parallel to the decrease in global 5hmC levels, the majority of altered promoters were reduced in 5hmC upon hypoxia (63%±3.9% of promoters versus 50% as expected by chance, P=0.014; FIG. 2C; Table S1), further confirming that hypoxia compromises DNA hydroxylation. Analysis of 5mC-DIP-seq moreover revealed a corresponding enrichment of 5mC (62%±4.6%, P=0.008; FIG. 2D; Table S2), indicating an accumulation of DNA methylation at gene promoters. To independently confirm the presence of this increased DNA methylation at a later time point, an orthogonal technology was used, i.e. targeted bisulfite sequencing of regions selectively isolated using capture probes. This method enables a base-resolution absolute quantitation of DNA methylation at loci covering ~85 Mb of gene promoters. Application of this independent technique on cells exposed to 48 hours of hypoxia confirmed the observed accumulation of 5mC specifically at gene promoters (74%, P=0.001; FIG. 2E; Table S3). The increase was limited to methylation at CpG dinucleotides, and no change in non-CpG methylation was noted, thus excluding technical bisulfite conversion artifacts and arguing against an altered de novo DNMT activity (Arand et al., 2012). Hypermethylation events were mostly associated with a decrease in expression upon hypoxia (FIG. 2F; P=0.007). Importantly, there was a significant overlap between those regions with less 5hmC after 24 hours of hypoxia, and those hypermethylated after 48 hours (P=0.033) further strengthening the notion that reduced TET activity leads to an accumulation of 5mC. Notably, other regions of the genome (gene bodies and intergenic regions) were not significantly altered (FIG. 2C-D), with the exception of CpG islands which, similar to promoter regions, displayed a significant loss of 5hmC (on average in 58% versus 50% as expected by chance, P=0.01), although this failed to translate into an increase in 5mC. Remarkably, although a loss of 5hmC and a gain of 5mC were consistently noted in each individual experiment, there was considerable heterogeneity in the affected loci across experiments. This suggests that these changes occur in every cell, but that they at least to some extent occur stochastically. Similar dynamics have been observed in mutagenic processes, where genetic variation arises stochastically but provides a substrate for Darwinian selection of tumor cells.

Example 4

Selection of Hypermethylation Events in Hypoxic Tumors

Figure 3:
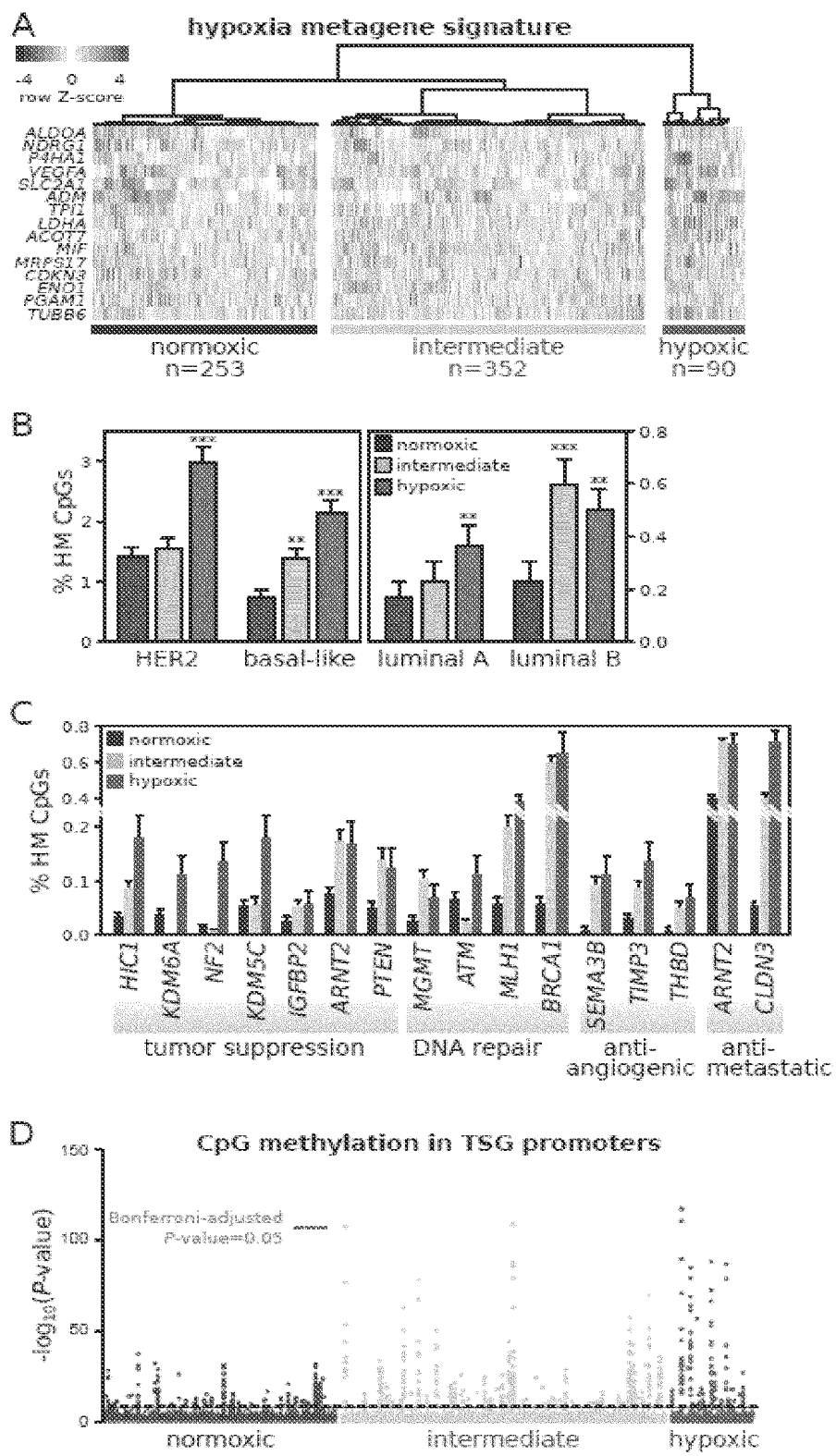
FIG. 3: Impact of hypoxia on hypermethylation frequencies in human breast cancers. A. Stratification of 695 human breast tumors by expression of the hypoxia metagene (Buffy et al., 2010). B. Percentage of hypermethylated (HM) CpGs out of all frequently hypermethylated CpGs at the promoters of 419 genes in 695 breast tumors, stratified for subtype. C. Hypermethylation frequency in the promoter of selected genes. D. Significance of the hypermethylation of CpGs in the promoters of tumor suppressor genes (TSGs), as stratified by the hypoxia metagene signature. E. Percentage of hypermethylated CpGs in the promoters of all genes, oncogenes and TSGs. F. Fraction of all CpGs that are hypermethylated in the promoter of the indicated genes. G. Expression of TSGs with at least one hypermethylation event in their promoter, relative to the average expression of the corresponding TSG in all breast tumors (Z-score). H. Global DNA methylation levels, as estimated by averaging the values across the ~485000 probes of Infinium 450K arrays assessing CpG methylation in normoxic, intermediate and hypoxic breast tumors. Bars in panels B, C and E represent the mean frequency±s.e.m. of hypermethylation event per tumor and CpG assessed.

We therefore analyzed whether the observed epimutations can, similar to genetic mutations, be a substrate for selection. Cell lines cannot recapitulate the complex set of mutational pressures active in developing tumors. Hence, to model the contribution of epimutations to the oncogenic process, we analyzed 695 breast tumors profiled in The Cancer Genome Atlas for DNA methylation (450K array) and gene expression (RNA-seq) (Cancer Genome Atlas, 2012). Unsupervised clustering of tumors by their expression of the hypoxia metagene signature (Buffy et al., 2010) classified 90 tumors as hypoxic, 253 as normoxic and 352 as intermediate (FIG. 3A). We next analyzed DNA methylation in these tumors, and annotated significant increases in DNA methylation (Bonferroni-corrected P-value<0.05) as hypermethylation events. The promoters of 419 out of 29649 annotated genes displayed frequent hypermethylation events (Table S4). Such hypermethylation events in normal breast tissue were 89% less frequent (P=5×10−81). Stratifying these tumors for their hypoxia status revealed that the hypermethylation frequency was 5.6-fold higher in hypoxic versus normoxic tumors (P=5×10−76), and that hypermethylation events at the vast majority of genes were increased in hypoxic versus normoxic or intermediate tumors (respectively at 399 and 343 genes; Table S4). These hypermethylation events were not restricted to a small subset but affected 81 out of 90 hypoxic tumors. They moreover did not display a TET1, TET2, SDHA, FH, IDH1 or IDH2 mutation, indicating that hypermethylation is not genetically encoded by mutations in these genes. We next assessed whether the hypoxia-associated hypermethylation events occurred independently of tumor characteristics. Importantly, hypoxic and normoxic turners did not differ significantly in estimated turner percentage or in clinical factors such as grade, stage, tumor size, lymph node involvement or metastasis (FIG. 11A). Subtype distribution differed significantly (P<2×10−16), with enrichment of basal-like and, to a lesser extent, also luminal B tumors in the hypoxic subset relative to the predominant luminal A subset (FIG. 11A-B). This enrichment of basal like tumors conforms earlier results (Buffa et al., 2010). Importantly, ANOVA revealed that the enrichment of hypermethylation events in hypoxic tumors was subtype independent (P=1×10−12; FIG. 3B). Similar results were obtained for 57 glioblastoma multiforme tumors profiled for both methylation and gene expression in TCGA, as the hypermethylation frequency was 3.4-fold higher in hypoxic versus normoxic or intermediate tumors (FIG. 11C, D). Hypermethylated genes in hypoxic glioblastomas moreover overlapped significantly with those in IDH1 mutant glioblastomas (35% overlap, P<10−16; FIG. 11E). The latter mutations are known to inactivate TET enzymes, thus further implicating the TETs in hypoxia-induced hypermethylation. Gene ontology of genes with hypermethylation events in hypoxic breast tumors revealed that genes involved in DNA repair and apoptosis were frequently inactivated in tumors (FIG. 3C-D, FIG. 11F). Indeed, pro-apoptotic TSGs such as PTEN and HIC1 but also TSGs involved in DNA repair, such as BRCA1, MLH1 and MGMT, were most consistently methylated in hypoxic tumors. Consistent with tumor hypoxia inducing tumor angiogenesis and metastasis, hypermethylation was also frequently observed in genes suppressing metastasis (ARNT2 and CLDN3) and inhibiting angiogenesis (TIMP3, THBD, SERPINE1, SEMA5B; FIG. 3E). To confirm that TSGs were specifically affected, we additionally queried a set of TSGs commonly inactivated in cancer (Vogelstein et al., 2013). Hypoxic tumors displayed an increased number of hypermethylation events at TSG promoters in comparison to normoxic tumors (FIG. 3D-E; P=4.1×10−14). The increase was specific for TSGs, as there was no effect in other gene classes such as oncogenes (FIG. 3E). TSG hypermethylation was moreover more pronounced in hypoxic versus normoxic tumors (FIG. 3D), and ~3 times more likely to cluster at a single TSG promoter in hypoxic versus normoxic tumors (P=8×10−7, FIG. 3F). Furthermore, only in hypoxic tumors they were associated with a down-regulation of TSG expression (FIG. 3G).

Example 5

Role of DNMTs in Tumor Hypermethylation Events

Theoretically, DNA hypermethylation can occur not only through a decrease in DNA demethylation, but also through an increase in DNA methylation. No significant increase in DNA methylation under hypoxia was however noted in ES or MCF7 cells (FIG. 1B). Similarly, assessing the global methylation status of hypoxic breast tumors revealed a subtype-independent global decrease in DNA methylation (P=1.0×10−4), rather than an increase (FIG. 3H). To further exclude that DNMTs are involved in TSG hypermethylation in breast cancer, we assessed expression of DNA methyltransferases in tumors stratified for hypoxia. This revealed a subtype-independent loss of expression of DNMT3A (P=2.8×10−5). The expression of DNMTs in each tumor with the corresponding DNA methylation moreover revealed a significant, positive correlation for DNMT3A and UHRF1, further indicating that the activity of these proteins could drive global 5mC levels (FIG. 11G; P<0.001). Importantly, no correlation could be detected between DNMT expression and the number of TSG hypermethylation events in these tumors. TET1 and TET3 expression on the contrary did correlate, inversely, with hypermethylation at TSGs (P-value<0.01). Together these data support the notion that a decrease in the activity of TETs, but not an increase in the activity of DNMTs, is responsible for the observed TSG hypermethylation under hypoxia. They moreover reveal that these hypermethylation events occurred at a background of global hypomethylation.

Example 6

Rescue and Exacerbation of Hypoxia-Induced Hypermethylation in Tumors

Figure 4:
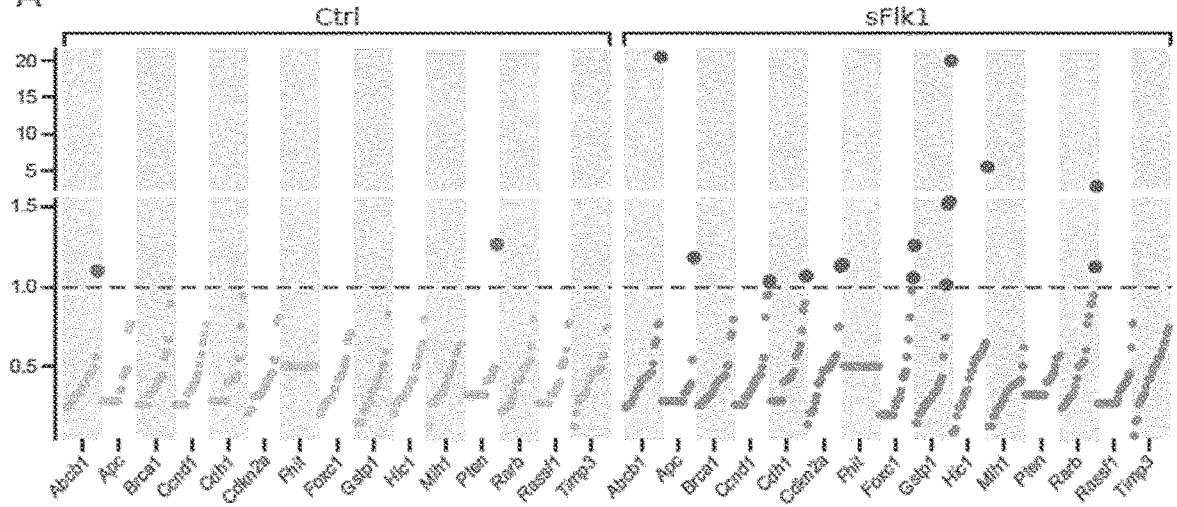
FIG. 4: Impact of blood vessel normalization and angiogenesis inhibition on tumor suppressor hypermethylation frequencies in tg(MMTV-PyMT) mice. DNA extracted from tumors developing in mice receiving the specified hydrodynamic injection (A) or of the indicated genotypes (B) was bisulfite converted, PCR-amplified for the indicated TSGs and sequenced to a depth of ~500×. Plotted are Z-scores of hypermethylation, relative to the more normoxic tumors (i.e. Ctrl and Phd2+/− for panels A and B, respectively).
Figure 4:
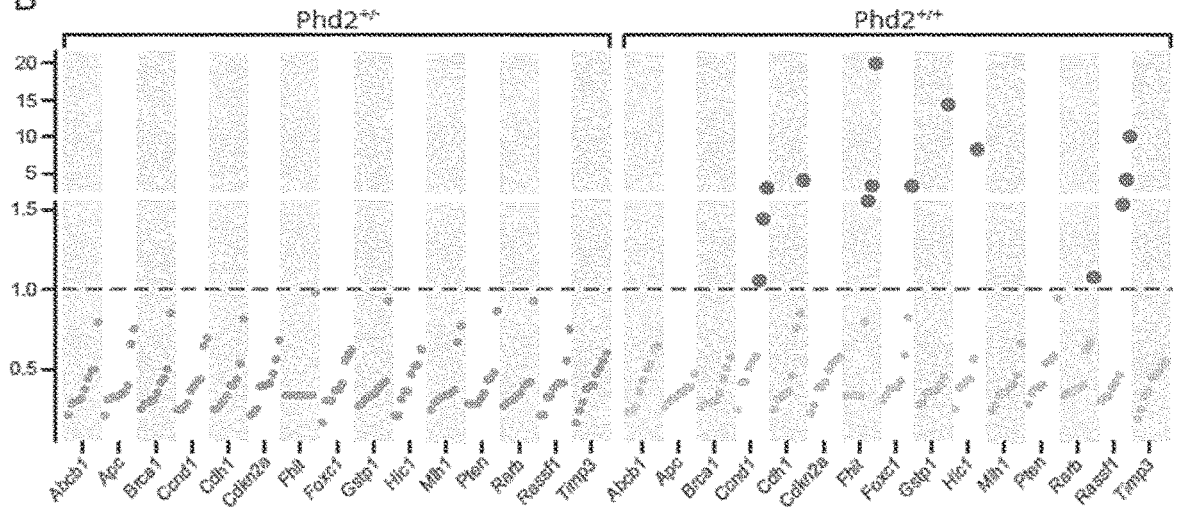
Figure 5:
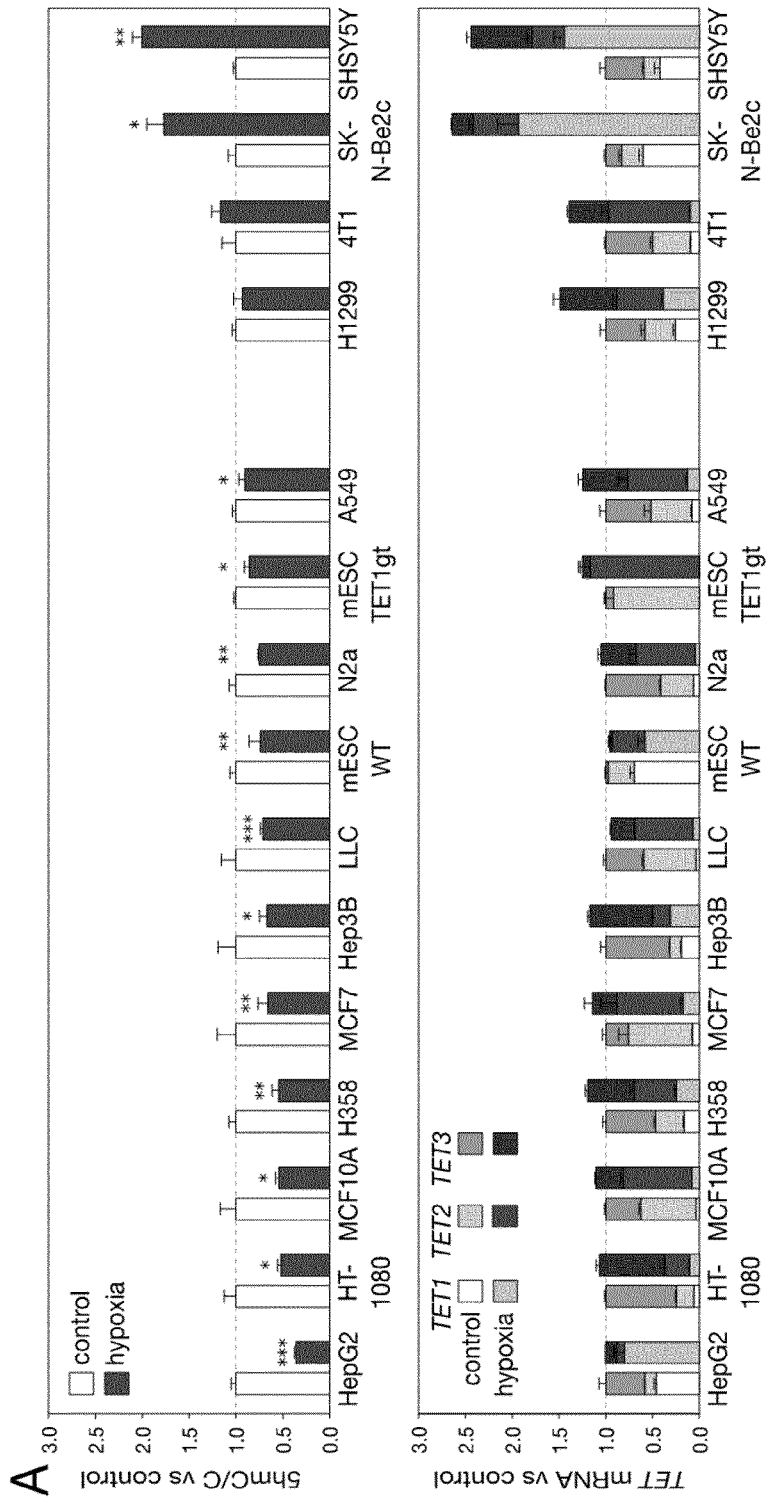
FIG. 5: Effect of hypoxia on 5hmC in vitro. A LC/MS analysis of global 5hmC (upper), and Taqman analysis of overall TET expression levels (lower) in the indicated cell lines grown for 24 h under control (21% O2) and hypoxic (0.5% O2) conditions. Levels are expressed relative to control. Expression is displayed relative to the total estimated cDNA copy number of all 3 TET paralogues combined.
Figure 12:
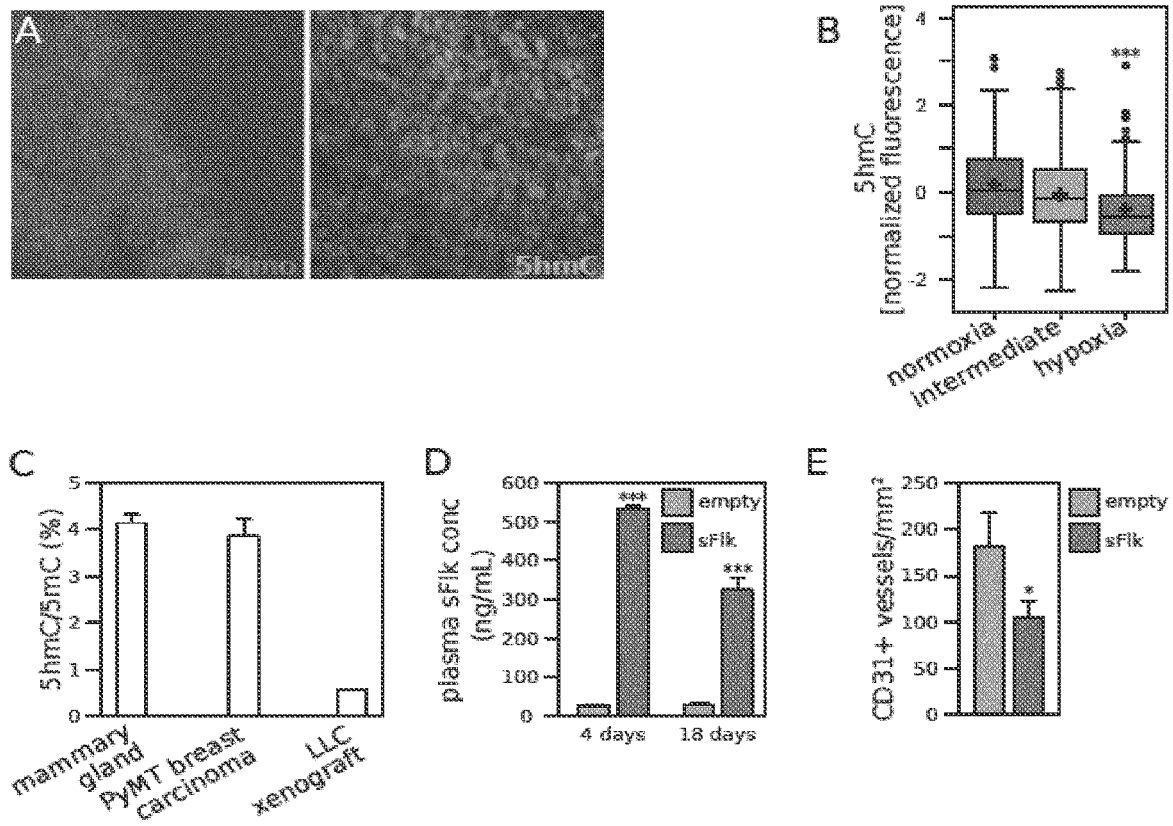
FIG. 12: 5hmC and hypoxia in breast tumors from tg(MMTV-PyMT) mice. A Immunofluorescence staining of hypoxic areas marked by pimonidazole adducts (green) and 5hmC (green) in a breast tumor from a tg(MMTV-PyMT) mouse. B Quantification of the relative 5hmC signal in pimonidazole positive, intermediate and negative areas. C Global levels of 5hmC in DNA from mammary glands, PyMT-induced breast tumors and a Lewis lung carcinoma xenograft. Plasma sFlk1 concentrations at the indicated times after hydrodynamical injection with an empty or sFlk1-overexpression plasmid (resp. grey and red). E-H Quantification of tumor vessel number (E) and hypoxic areas (G) of tumors from tg(MMTV-PyMT) mice, hydrodynamically injected with an empty or sFlk1-overexpression plasmid, with representative images of blood vessel stained for CD31 (F) and hypoxic areas stained for pimonidazole adducts (H) of tumors from tg(MMTV-PyMT) mice, hydrodynamically injected with an empty or sFlk1-overexpression plasmid. Scale bar=100 µm. I DNA extracted from tumors developing in mice receiving the specified hydrodynamic injection was bisulfite converted, PCR-amplified for the indicated oncogenes and sequenced to a depth of ~500×. Plotted are Z-scores of hypermethylation relative to the more normoxic tumors. J Quantification of pimonidazole-positive, hypoxic areas relative to the total tumor area in a tg(MMTV-PyMT) (grey) and a tg(MMTV-PyMT); Phd2+/− background (blue). Bars represent the mean±s.e.m. of at least 5 different tumors or independent replicates. K As in (I), but for mice of the indicated genotype.
Figure 12:
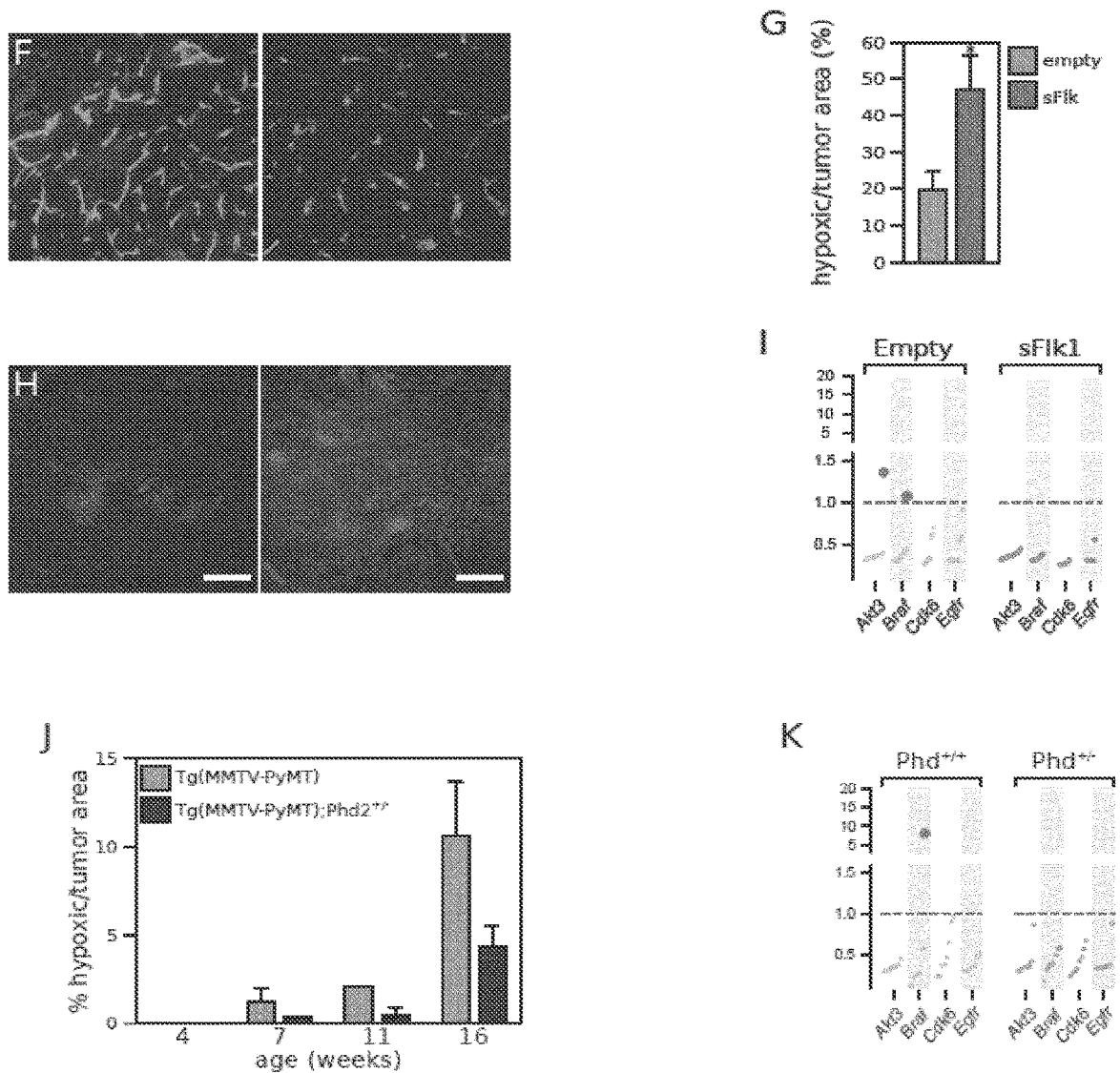

Next, we leveraged a murine model of breast cancer to manipulate tumor oxygenation and thus further assess the impact of hypoxia on epimutagenesis. Mice expressing polyoma middle T under the mouse mammary tumor virus promoter (MMTV-PyMT) spontaneously develop breast tumors, with hypoxic areas evident from 7 weeks onwards, at the late adenoma stage. Similar to what was observed in patient-derived xenografts, hypoxic tumor areas were depleted in 5hmC (FIG. 12A-B). Moreover, 5hmC levels in these spontaneous tumors were 5 times higher than those in tumors developing from a grafted cell line, suggesting greater potential for regulation (FIG. 12C). To first test whether decreasing tumor oxygenation also increases TSG hypermethylation in this model, 11 week old MMTV-PyMT mice were hydrodynamically injected with a soluble Flk1 (sFlk1)-expressing plasmid. The resultant increase in plasma sFlk1 concentrations (>11-fold during 3 weeks, FIG. 12D) was sufficient to prune the tumor vasculature, as revealed by a 42±10% reduction in vessel density in sFlk1-treated mice (FIG. 12E-F). As a consequence, hypoxia increased from 20% to 47% in response to sFlk1 treatment (FIG. 12G-H). To assess TSG hypermethylation, deep BS-sequencing (~1000-fold coverage) was developed for a panel of 15 TSG promoters. This revealed an exacerbation of the TSG hypermethylation phenotype by sFlk1 overexpression, with 10 out of 15 TSGs being hypermethylated relative to control, in at least one out of 24 hypoxic tumors (Fisher's exact P-value=0.010, FIG. 4B). Oncogenes tested failed to display the same increase in sFlk-treated tumors (FIG. 12I). In an attempt to rescue this effect, we normalized the vasculature in these tumors by intercrossing a heterozygous Phd2 loss-of-function allele with the PyMT transgene. As expected, this vessel normalization significantly reduced tumor hypoxia from 15% to 4% (FIG. 12J) (Leite de Oliveira et al., 2012; Mazzone et al., 2009). Interestingly, deep BS-seq applied to DNA from these Phd2+/+ and Phd2+/− tumors harvested at the late carcinogenesis stage (16 weeks) revealed that, whereas 8 out of 15 TSGs displayed significant hypermethylation in at least: one of 9 tumors from Phd2+/+ mice, no hypermethylation was observed in any of the 10 tumors from Phd2+/− mice (P-value=2.6×10−7, FIG. 4B). Notably, hypermethylation of oncogene promoters was again not affected (FIG. 12K).

Example 7

Figure 11:
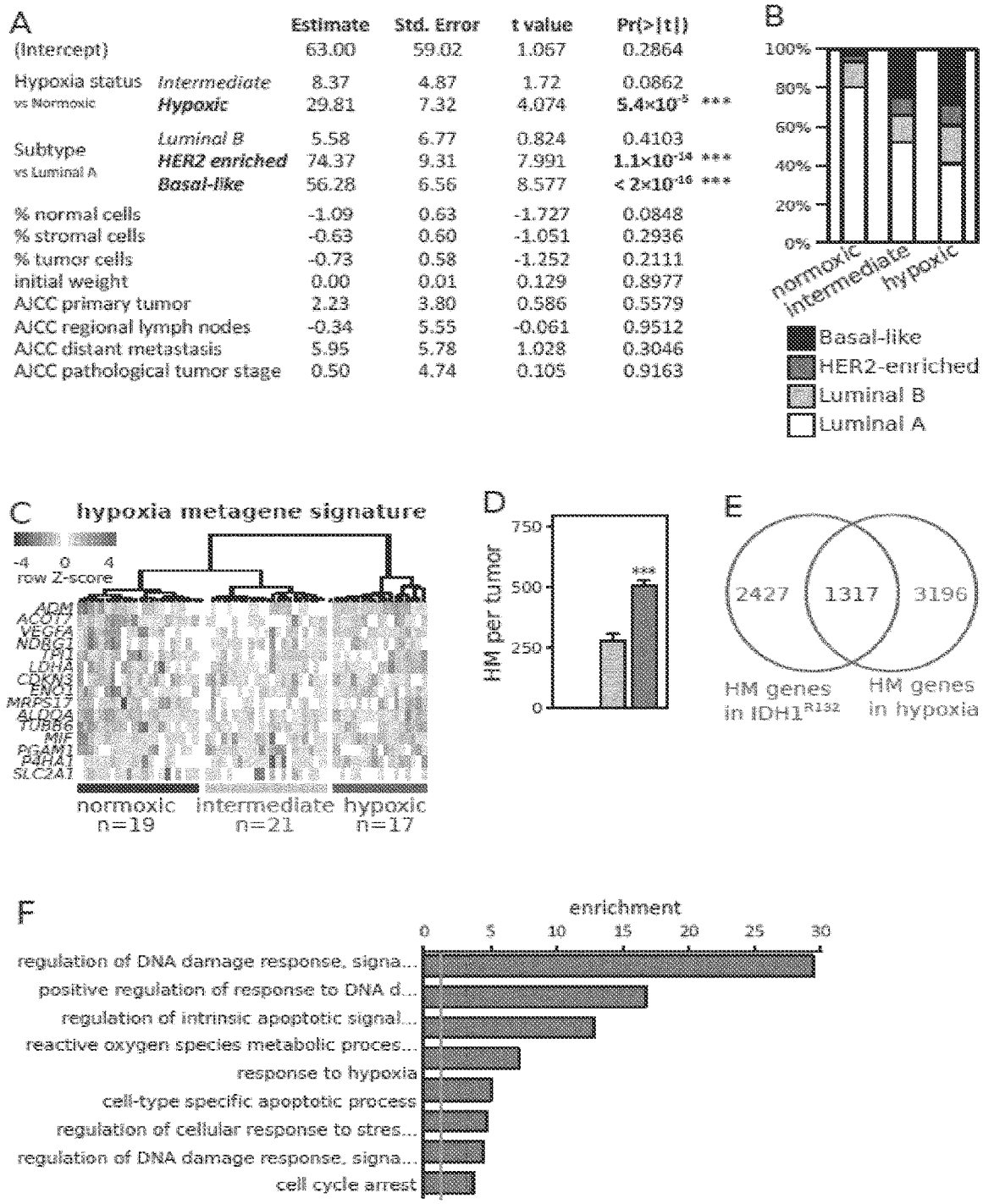
FIG. 11: Impact of Subtype and hypoxia on local hypermethylation and global DNA methylation. A Results of ANOVA for hypermethylation frequencies in 437 frequently hypermethylated genes. B Distribution of breast tumor subtypes between normoxic, intermediate and hypoxic tumors. C Stratification of 47 human glioblastoma multiforme tumors by expression of the hypoxia metagene (Buffa et al., 2010). D Hypermethylation events per glioblastoma tumor. E Overlap between hypermethylation (HM) in 17 hypoxic glioblastomas and 6 with an IDH1R132 mutation. F Results of ontology enrichment analysis for genes hypermethylated in 90 hypoxic breast tumors. G Correlations between average β values and the expression of genes involved in DNA methylation for 695 breast tumors.
Figure 11:
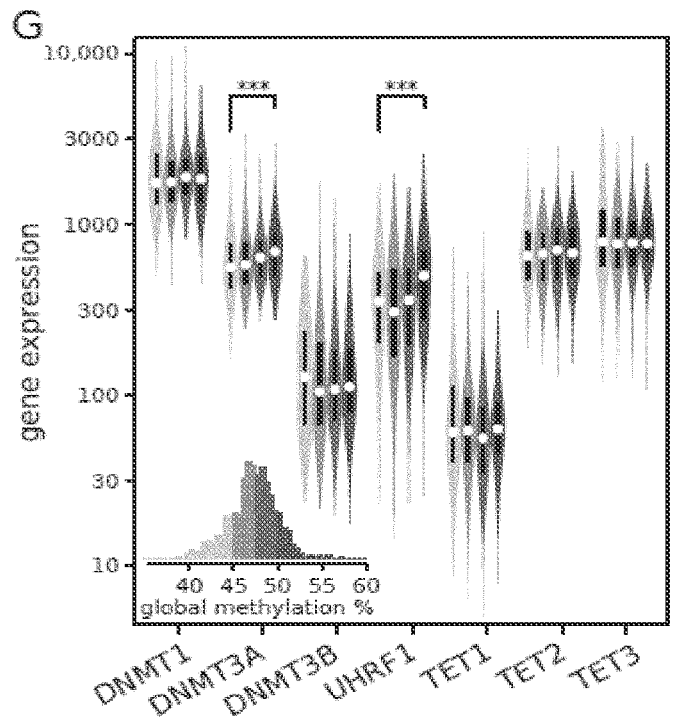

Effect of Oxygen Concentrations on the Activity of Recombinant Purified TET Enzymes In Example 2 we have demonstrated that under hypoxia, reduced oxygen tensions directly diminish the oxidative activity of TET enzymes to decrease 5hmC levels. In a final experiment, we assessed the effect of $O_2$ concentrations on the activity of recombinant purified Tet1 enzyme. We measured conversion of 5mC to 5hmC on double-stranded genomic DNA, at a different range of $O_2$ concentrations. We observed a dose-dependent loss of 5hmC production, with a $K_m$ of Tet1 for oxygen of 3 corresponding to ~0.3% $O_2$ (FIG. 11). Particularly, under the hypoxic conditions applied in this study (0.5% $O_2$), TET activity was reduced by 45±7% (P=0.01). These data further demonstrate that under hypoxia, reduced oxygen tensions directly diminish the oxidative activity of TET enzymes, independently of changes in HIF activity, competing metabolite concentrations, cell proliferation, nuclear ROS or TET expression.

Example 8

Hypoxia Induces Hypermethylation in a Large Number of Tumor Types

Figure 6:
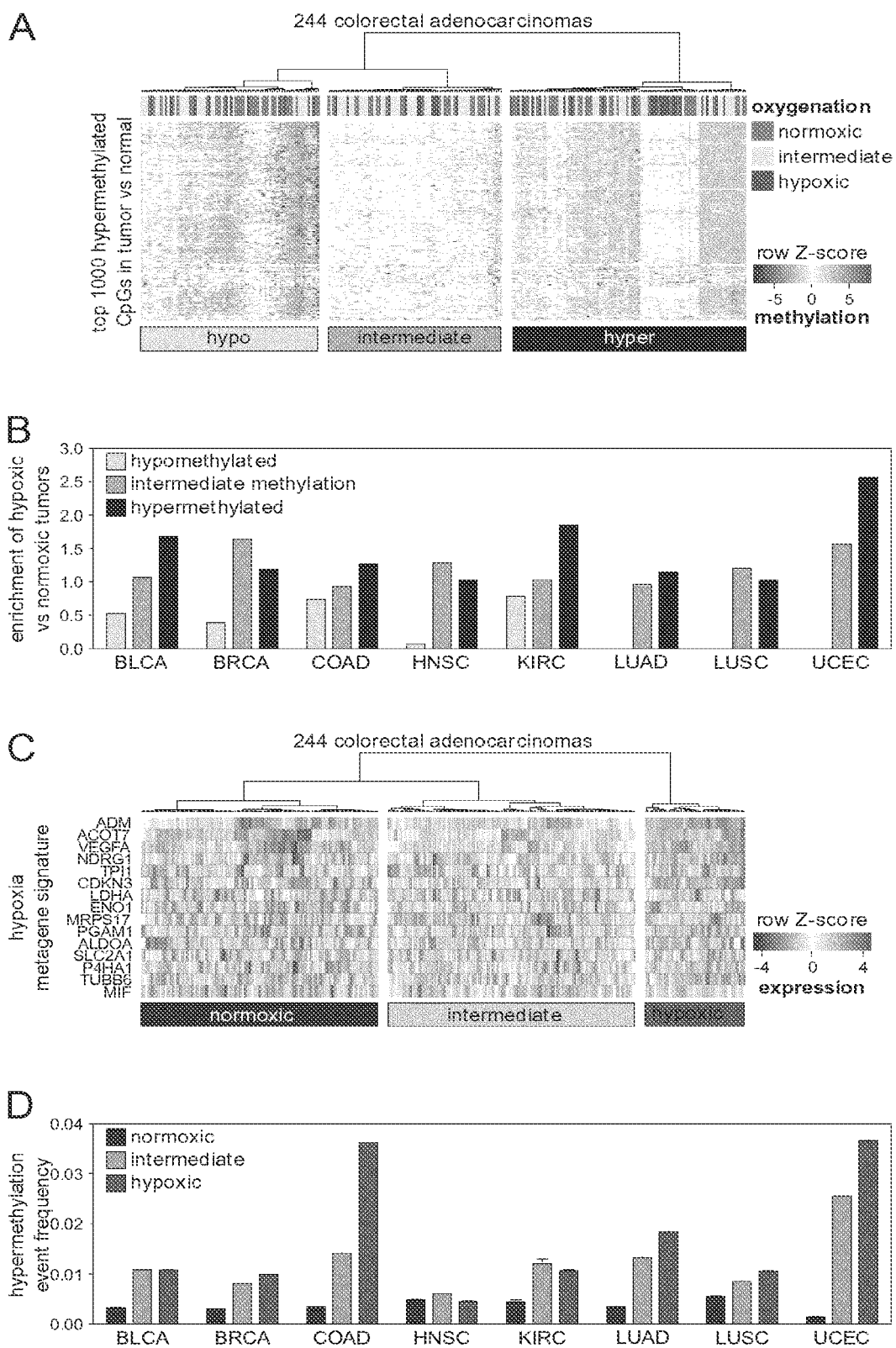
FIG. 6: Hypoxia induces hypermethylation in a large number of tumor types. A Unsupervised clustering of 1000 CpGs showing the highest average methylation increase in 244 colorectal adenocarcinomas versus normal colorectal tissue. The top 3 clusters are highlighted. B Observed/expected number of hypoxic versus normoxic tumors in the 3 first methylation clusters, characterized by relatively low, intermediate and high methylation levels, for 8 tumor types characterized in the TCGA Pan-Cancer effort. C Unsupervised clustering of 14 genes from the hypoxia metagene in 244 colorectal adenocarcinomas. The top 3 Clusters are highlighted. D Percentage of hypermethylated (HM) CpGs in the promoters of frequently HM genes, for 8 tumor types characterized in the TCGA Pan-Cancer effort. Asterisks indicate P-values (*P<0.05, ***P<0.001).
Figure 13:
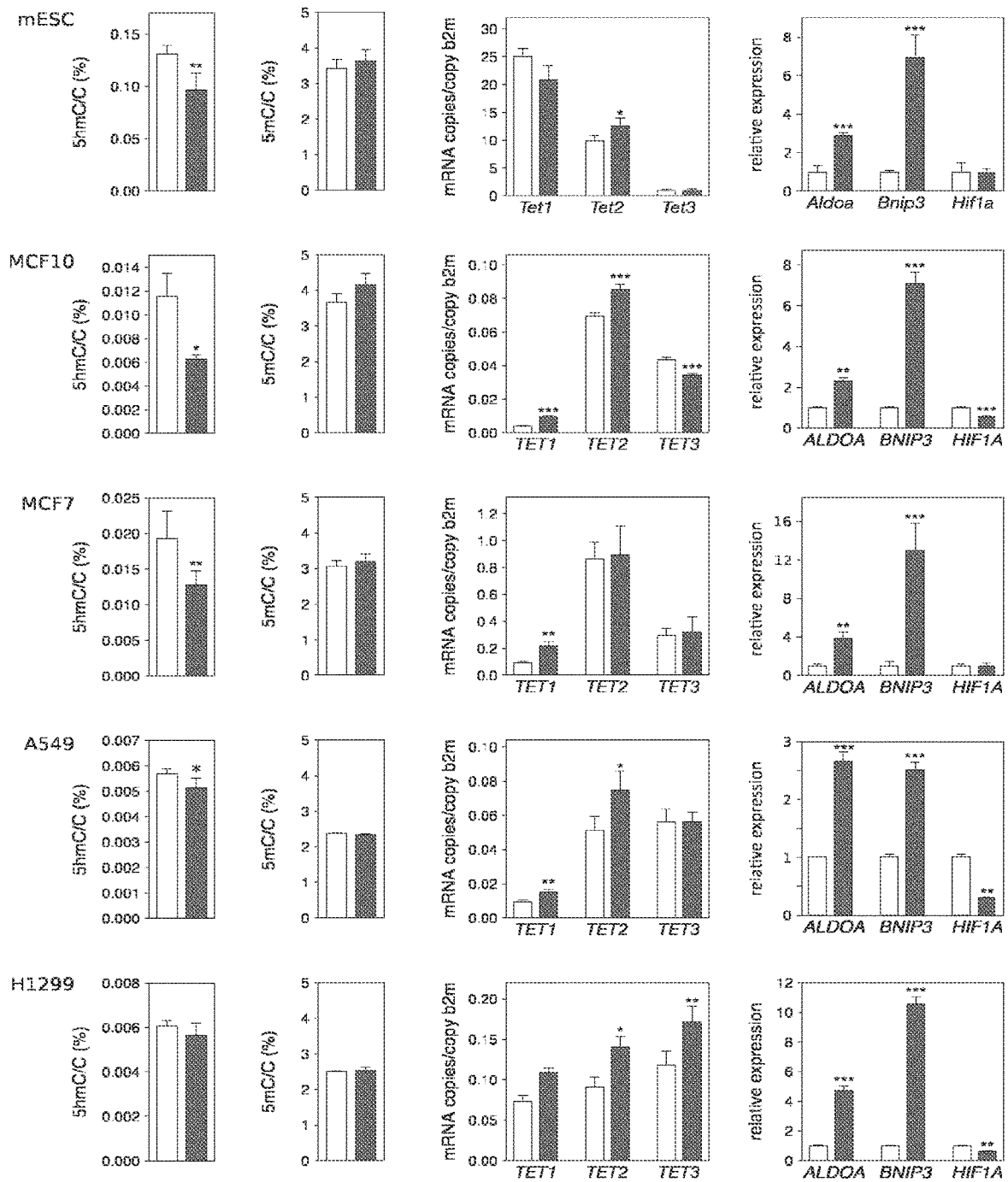
FIG. 13: Hypoxia-induced changes in the global 5hmC and 5mC content of DNA, in TET mRNA expression and in hypoxia marker gene expression of 15 cell lines grown for 24 h under control (white) or hypoxic (0.5% $O_2$, red) conditions. Bars represent the mean±s.e.m. of at least 5 different replicate samples grown on different days, asterisks indicate P-values of paired t-tests (*P<0.05, P<0.01, *P<0.001).
Figure 13:
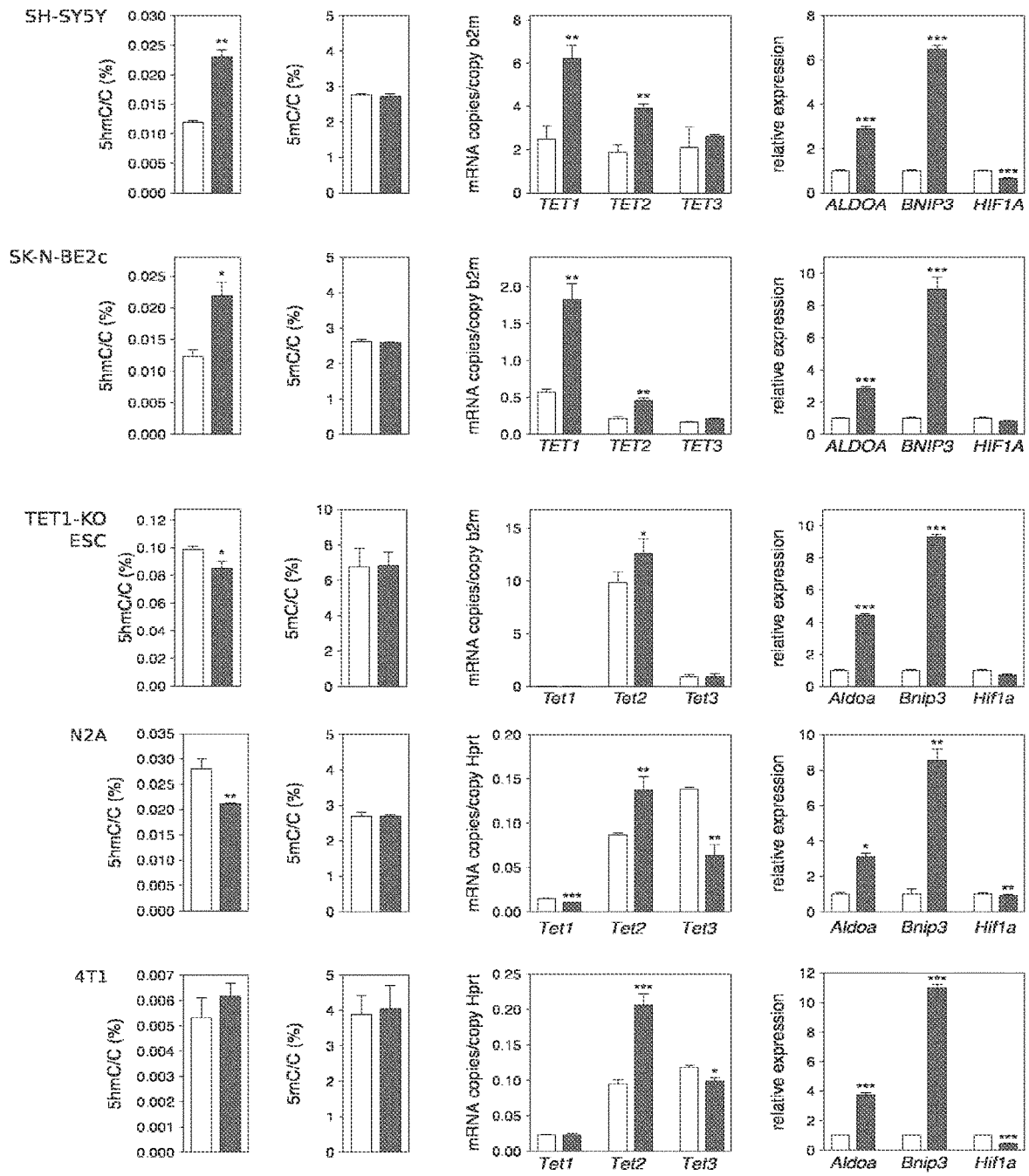
Figure 13:
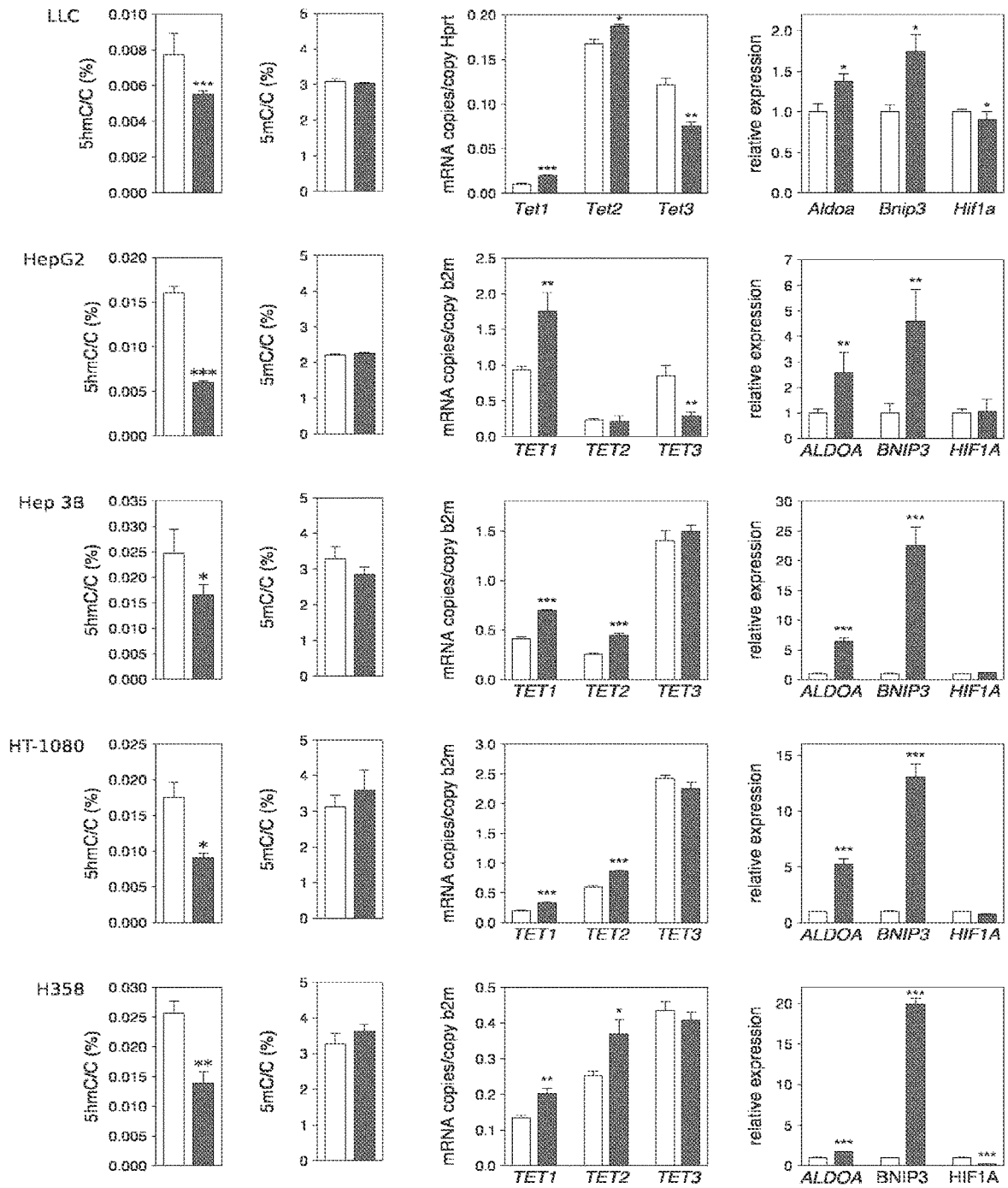
Figure 14:
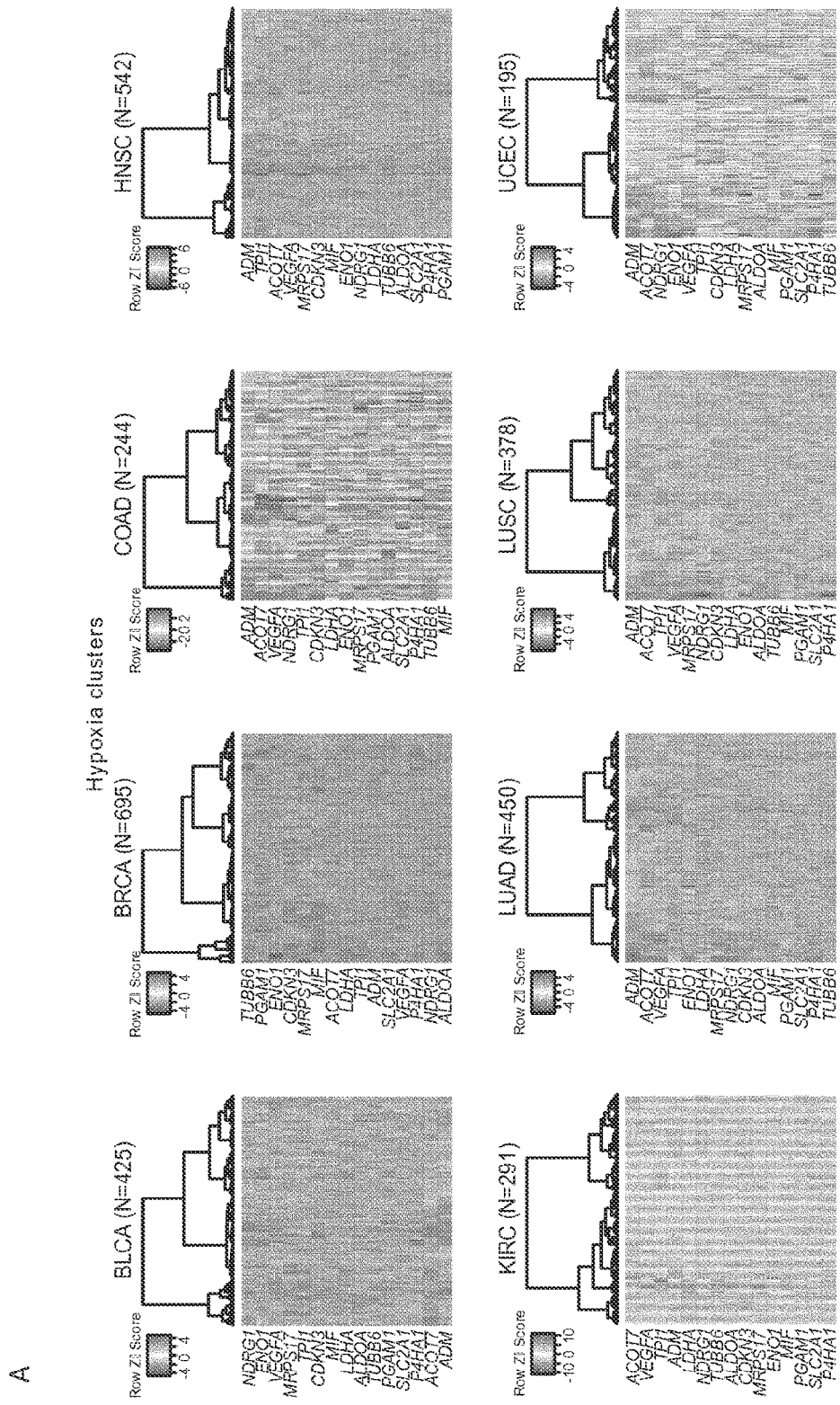
FIG. 14: Impact of hypoxia on hypermethylation frequency in TCGA patient tumors. A Hypoxia marker gene expression clusters, with the first 3 clusters used to define normoxic, intermediate and hypoxic tumors. B Unsupervised clustering of 1,000 CpGs showing the highest average methylation increase in tumor versus corresponding normal tissues. The first 3 clusters were used to define tumors of low, intermediate and high methylation. C Boxplots showing the relative expression (Z-score) of genes in tumors wherein they have either 0 or ≥1 hypermethylation (HM) event in their promoter, stratified into normoxic, intermediate and hypoxic tumors (resp. blue, grey and red). Diamonds indicate means, boxplot wedges indicate 2 times the standard error of the median. Genes having 1 or more hypermethylation events in their promoters have a lower average expression level (P<0.01 for all). D Fraction of genes having a promoter that is rich, intermediate or poor in CpGs, out of all gene promoters that are assessed on the 450K array (450K), and out of all gene promoters that are frequently hypermethylated in the indicated cancer types.
Figure 14:
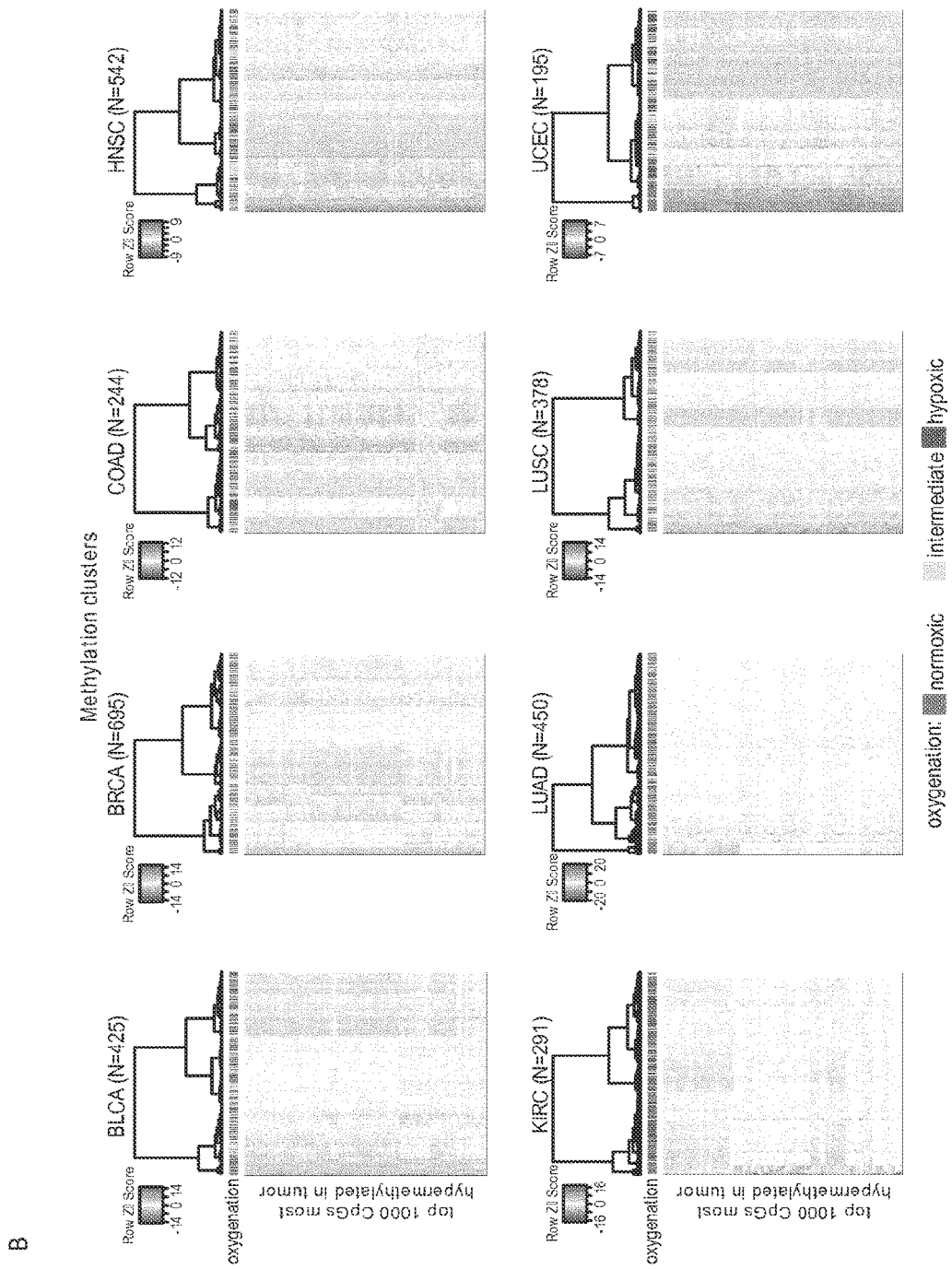
Figure 14:
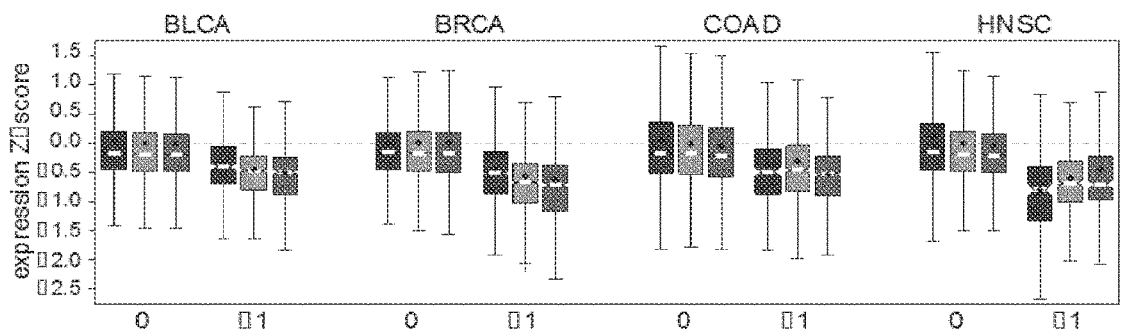
Figure 14:
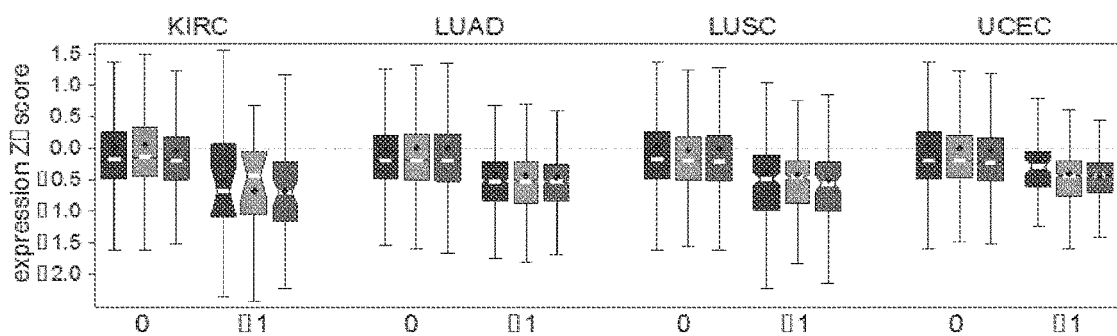
Figure 14:
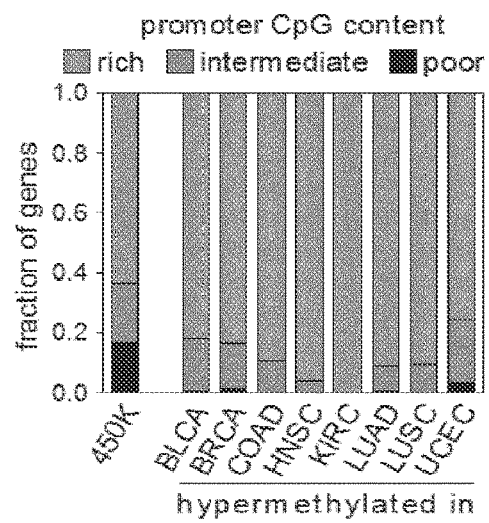

Next to the impact of hypoxia on TET activity tested in mouse embryonic stem cells and in MCF10A and MCF7 cells as explained in Example 1, we also assesses whether TET activity is affected by hypoxia in other tumor types. We additionally exposed 8 human and 4 murine cell lines with detectable 5hmC levels for 24 hours to 0.5% $O_2$, a level commonly observed in tumors (Vaupel et al 2007). In each cell line, hypoxia induction was verified using hypoxia marker genes (FIG. 13) and DNA was extracted and profiled for nucleotide composition using LC/MS. All together (Example 1 and results described here) 11 cell lines, including eight cancer cell lines derived from a range of different tissues (such as liver, lung and breast tissue) displayed a significant loss of 5hmC upon hypoxia (FIG. 6A). As earlier described in Example 1, these reductions in 5hmC did, however, not translate into a global increase in 5mC (FIG. 13), presumably because 5mC at many sites in the genome is not actively turned over. Additionally, to model whether hypoxia-associated hypermethylation contributes to the oncogenic process in other tumor types than breast tumors (Example 4), we analyzed 7 additional tumor types profiled in the pan-cancer study of The Cancer Genome Atlas (TCGA, 2012). Together with the breast tumor data described in Example 4, we now have data on the 8 tumor types for which both DNA methylation (450K array) and gene expression (RNA-seq) data were available for >100 samples: bladder, breast, colorectal, head and neck, kidney, lung adeno-, lung squamous, and uterine carcinoma. We classified each of these tumors as hypoxic, normoxic or intermediate using the hypoxia metagene signature from Buffa et al. (FIG. 6C, FIG. 14A) (Buffa et al 2010). Next, we analyzed tumor-associated DNA hypermethylation in each of these tumor types, by performing unsupervised clustering of 1,000 CpGs that displayed the strongest hypermethylation in tumor versus corresponding normal tissue (FIG. 6A, FIG. 14B). We selected the 3 first clusters, displaying low, intermediate and high methylation, and analysed the enrichment of hypoxic tumor samples in each cluster. Interestingly, for all tumor types, the hypoxic tumors were more prevalent than normoxic tumors in the most hypermethylated cluster, while vice versa, normoxic tumors were more prevalent in the less methylated cluster (FIG. 3B; P=2×10−4 in a Cochran-Armitage test). Overall, the contribution of hypoxic tumors to the hypermethylated clusters was 1.73-fold higher than to the less methylated clusters (252/1155 versus 89/707), indicating that hypoxia leads to increased methylation in human tumors. In the 8 tumor types assessed, the promoters of 187±38 out of 29,649 annotated genes displayed frequent HM events (Bonferroni-corrected P-value<0.05; Extended data table 5). Stratifying all these tumors for their hypoxia status revealed that hypoxic tumors had on average 4.8-fold higher HM frequencies at CpGs in these gene promoters versus normoxic tumors (FIG. 6C; $P<4.1\times10^{-13}$), and that for 63% of these individual genes, HM events were more frequent in hypoxic versus normoxic or intermediate tumors (Extended data tables 5-12). These HM events were functional, as they on average reduced gene expression in tumors carrying these HM (FIG. 14C). They primarily affected promoters with a high or intermediate CpG content, in line with the known TET target preference (FIG. 14D) (Williams et al 2011). Furthermore, they were not restricted to a small subset, but found in 75% of hypoxic tumors. When considering HM frequencies in normoxic tumors as baseline, we estimated that up to 48% of all HM events in tumors were hypoxia-related.

Example 9

Reduced TET Activity Underlies HM in Hypoxic Tumors

Figure 7:
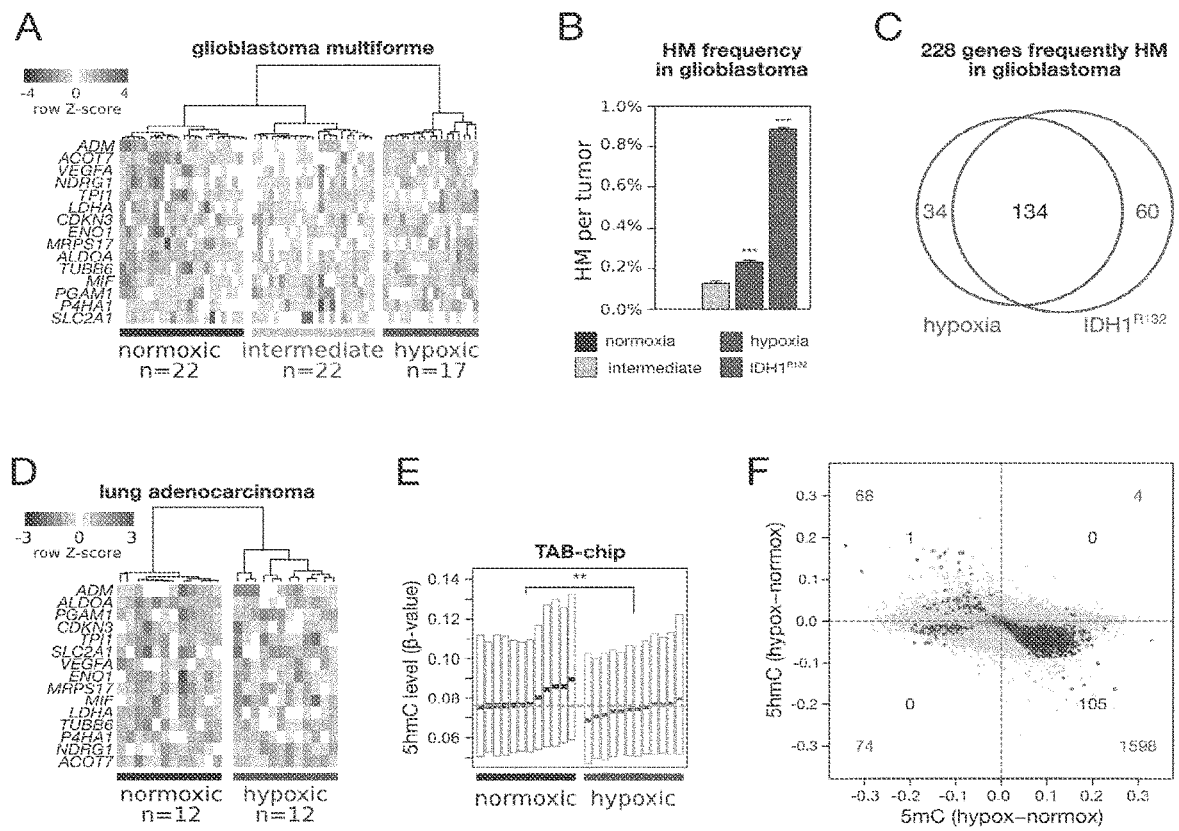
FIG. 7: Impact of hypoxia on TET activity in human cancers. A Hypoxia metagene signature of 61 glioblastoma multiforme tumors. B Frequency of hypermethylation events detected in 19 normoxic (blue), 21 intermediate (grey), 17 hypoxic (red) and 6 $IDH1^{R132}$ mutated (green) glioblastoma tumors. C Overlap between genes hypermethylated in hypoxic glioblastomas and/or hypermethylated in $IDH1^{R132}$-mutated glioblastomas, out of all 228 genes displaying frequent hypermethylation in glioblastoma (FDR<0.05%). D Hypoxia metagene signature of 24 non-small-cell lung tumors profiled for 5hmC and 5mC using 450K arrays. E Medians (bars) and quartiles (empty boxes) of hydroxymethylation level as measured across 485,000 probes of Illumina Infinium Human Methylation450 BeadChips, in 12 normoxic and 12 hypoxic non-small-cell lung tumors. F Scatter plots of changes in 5mC and 5hmC for every CpG, detected when comparing hypoxic and normoxic non-small-cell lung tumors. Grey dots represent all 485,000 probes, blue and red dots indicate probes, significantly altered in both 5mC and 5hmC, respectively at FDR=25% and at P<0.01. Asterisks indicate P-values (P<0.01, *P<0.001).

To assess the role of TET enzyme activity in hypoxia-associated HM events, we first assessed the overlap of HM induced by IDH1$^{R132}$ mutations, which inactivate TET enzyme (Figueroa et al 2012), with those induced by hypoxia. For this, HM events were assessed in glioblastoma multiforme tumors, profiled for both methylation and gene expression in TCGA. Among IDH1-wildtype glioblastomas, the HM frequency was as expected 3.4-fold higher in hypoxic versus normoxic or intermediate tumors (FIG. 7A, B). IDH1$^{R132}$ tumors were hypermethylated; their HM frequency was 3.9-fold higher than in hypoxic tumors, indicating that TET enzymes are, similar to our in vitro observations, only partially inhibited in hypoxic tumors (FIG. 7B). Overall, 228 genes were frequently hypermethylated in glioblastomas, 134 of which were also hypermethylated in hypoxic glioblastomas. Hypermethylated genes in both subgroups displayed a 58% overlap (P<10$^{-16}$; FIG. 7C), indicating that a loss of TET activity affects the same genes, irrespective of whether it is induced by hypoxia or IDH1$^{R132}$. Secondly, to more directly confirm that hypoxia-associated HM events occurred due to a loss in 5hmC, we selected 12 hypoxic and 12 normoxic non-small cell lung cancers, for which we had RNA expression data and DNA available (FIG. 7D). We profiled each tumor for 5mC using 450K arrays, and for 5hmC using the same arrays but a modified protocol (Nazar et al 2014). This analysis revealed a generalized loss of 5hmC in hypoxic tumors, with an average decrease in 5hmC β-values of 7% (P=3.7×10$^{-3}$; FIG. 7E). We thus directly confirmed that TET activity is also compromised in hypoxic tumors. In line with this generalized loss in 5hmC, the vast majority of individual probes altered (P<0.01) in 5hmC upon hypoxia displayed a loss (15,763 out of 16,293; Table S7). We next compared DNA methylation between these hypoxic and normoxic tumors. Although a generalized gain in 5mC was not significant, 5mC was increased at the majority of significantly altered individual probes (P<0.01) (8,087 out of 12,369 altered probes; Extended data table 23). By combining 5mC and 5hmC analyses, we observed that most of these 8087 probes (87%) gaining 5mC, displayed a loss of 5hmC. Moreover, of all 1744 probes significantly altered in both 5hmC and 5mC (P<0.01), 1598 (92%) were decreased in 5hmC and increased in 5mC (FIG. 7F). This thus directly implicates hypoxia-induced loss of 5hmC in the DNA hypermethylation we observed in hypoxic tumors.

Example 10

A Gene Panel for Monitoring HM Enrichment in Tumor Suppressor Genes

Figure 15:
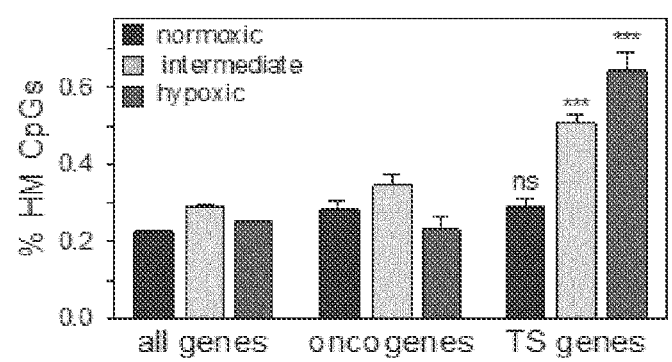
FIG. 15: TSG hypermethylation in murine breast tumors. A Frequency of HM events in the promoters of all genes, all oncogenes and all tumor suppressor genes (TS genes) as annotated (Vogelstein et al 2013), in human breast tumors described in TCGA and stratified into normoxic, intermediate and hypoxic subsets. B-C DNA was extracted from 53 tumors developing in MMTV-PyMT mice of the indicated ages (F) or weights (G) and sequenced to a depth of ~500×. Plotted are Z-scores of hypermethylation (y axis, exponential) for 15 tumor suppressor genes, relative to the tumors from 11-week-old mice. The dotted line represents the threshold for a Bonferroni-adjusted P<0.05, and bold darker dots the tumors displaying significantly increased HM events. D DNA extracted from 20 normal mammary glands from 14-week-old mice, PCR-amplified for the indicated TSGs and sequenced to a depth of ~500×. Plotted are Z-scores of hypermethylation relative to 11-week-old tumors.
Figure 15:
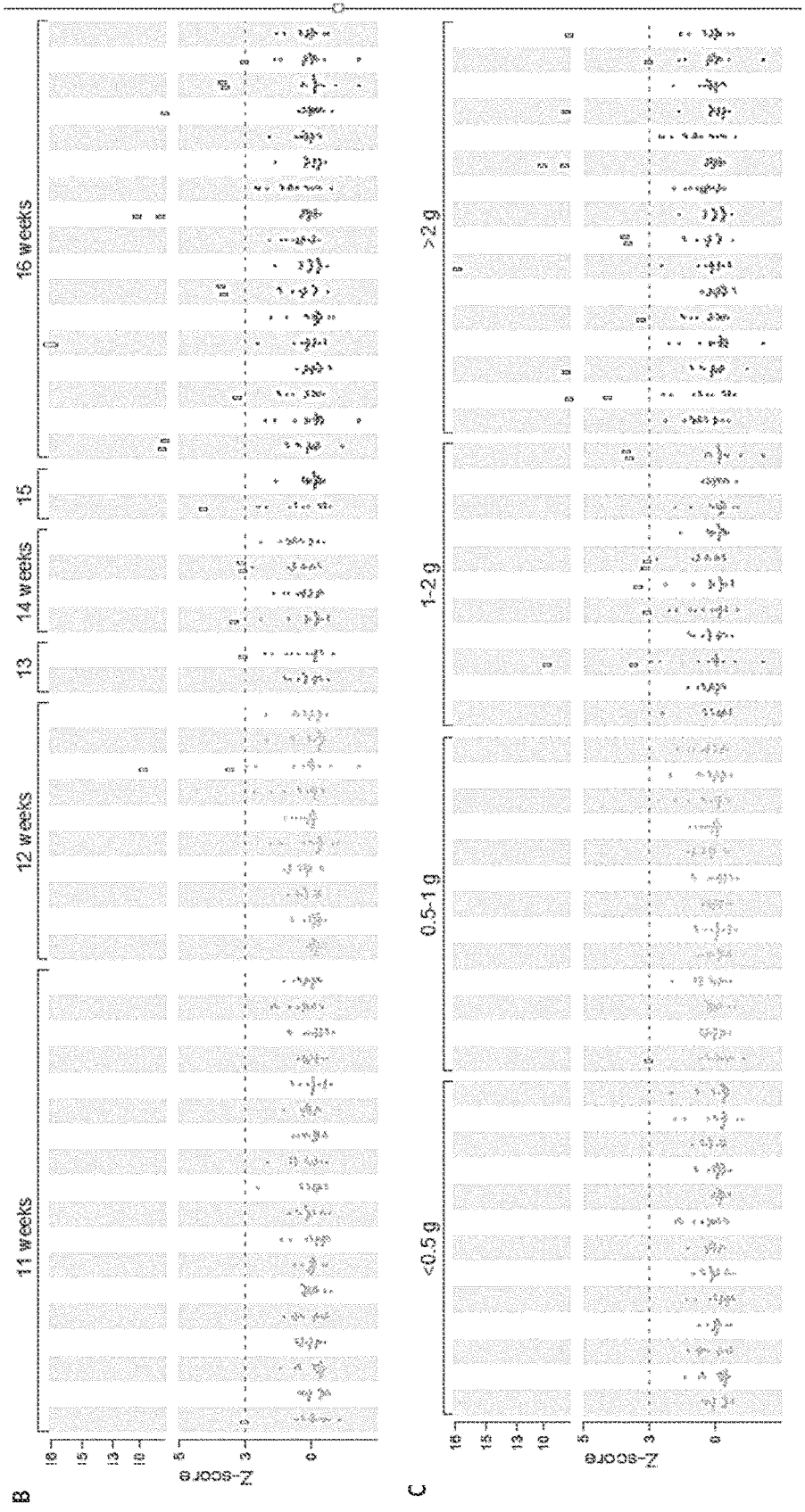
Figure 15:
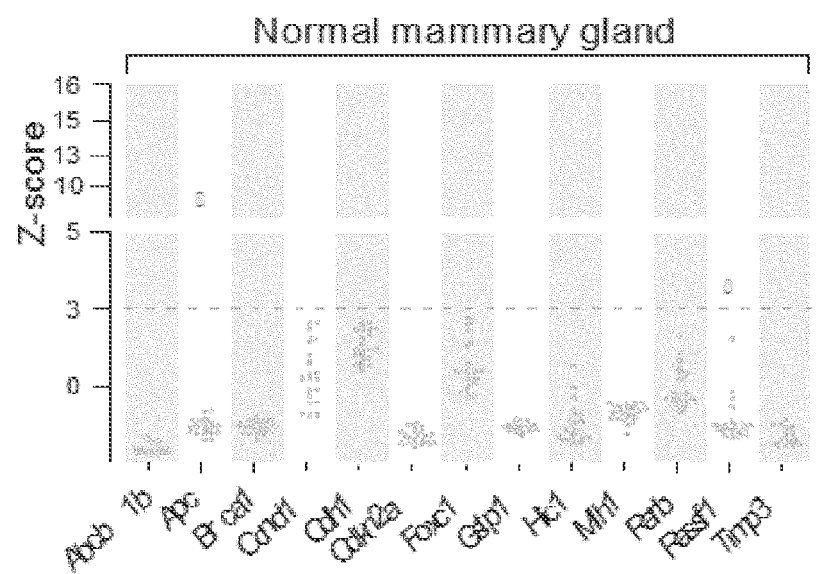

To construct a gene panel suitable for monitoring HM enrichment, we analyzed genes involved in cancer. Hypoxic human breast tumors displayed an increase in HM events at the promoters of tumor suppressor genes (TSGs) (FIG. 15A; P=4.1×10$^{-14}$). The increase was specific for TSGs, as no effect was observed for oncogenes (FIG. 15A). Monitoring HM events in TSGs is thus suitable to measure. HM changes arising due to manipulating tumor oxygenation. We developed deep BS-sequencing (>500-fold coverage) for TSG promoters (Vogelstein et al 2013). In line with our expectations, the frequency of HM events increased dramatically with age or size and the associated hypoxia: as was evident when assessing tumors isolated at ages ranging from 11 to 16 weeks (FIG. 15B-C). TSGs in normal mammary glands likewise did not have an increased HM frequency (FIG. 15D).

Discussion

We here show that hypoxia decreases global 5hmC levels in vitro, independently of changes in TET expression, metabolite concentrations, HIF activity or nuclear reactive oxygen. This decrease is predominantly seen at gene promoters, consistent with these sites being a preferential target of TETs. The reduced oxidation of 5mC translates into an accumulation of 5mC at these sites, which, similar to genetic mutations, become a substrate for selection during the carcinogenic process (Feinberg and Irizarry, 2010). Tumor epimutations have long been suspected to occur through the selection and propagation of random DNA methylation variants. However, this stochastic model has been called into question recently by the identification of genetically encoded TSG hypermethylation phenotypes (Oey and Whitelaw, 2014; Struhl, 2014). Following this instructive model, tumors with mutations in DNA demethylation-associated genes such as TET1, TET2, SDHA and IDH1 display DNA hypermethylation at a wide range of promoters including TSGs. Nevertheless, hypermethylation of TSGs also occurs in tumors without mutations in the genes encoding these enzymes. Our data, which demonstrate that hypoxia drives hypermethylation, indicate that both genetically encoded as well as stochastically induced epimutagenesis models co-exist. Given the pervasive nature of hypoxia across a wide range of solid tumors, the mechanism described here could be relevant for most solid tumors, a notion supported by the fact that up to 49% of all HM events in 8 tumor types investigated were hypoxia-related. Furthermore, these effects replicated in all tumor types investigated, and were independent of mutation- and proliferation-induced HM. Our observations thus reveal a mechanism for the global loss of 5hmC that is pervasive in a wide variety of tumor types (Yang et al., 2013). The fact that loss of 5hmC following hypoxia was observed in vitro using purified TET enzymes, in a pre-malignant and cancerous breast cancer cell line, as well as in vivo, in patient-derived xenografts and spontaneously-occurring tumors of both mouse and human origin, confirms that hypoxia-driven loss of 5hmC represents a common and biologically robust phenomenon. Remarkably, the epimutational load in a spontaneous murine breast cancer model became more pronounced when exacerbating tumor hypoxia. The model proposed here, wherein hypoxia contributes to TSG promoter hypermethylation by suppressing TET activity, provides an elegant mechanism for the association of hypoxia with many well-established (mal)adaptive processes. For instance, tumor hypoxia has been linked to increased tumor aggressiveness and invasion, a more pronounced genomic instability (because of reduced activity of DNA repair genes), metabolic reprogramming of the tumor to glucose addiction, recruitment of macrophages with immunosuppressive properties to the tumor, etc (Aguilera and Gomez-Gonzalez, 2008; Casazza et al., 2013; Loges et al., 2009; Stapor et al., 2014; Vanharanta and Massagué, 2013). Pathway analyses of genes affected by hypermethylation in hypoxic versus normoxic breast tumors revealed that genes involved in cell cycle arrest, DNA repair and apoptosis were frequently inactivated. Additionally, hypermethylation was also observed in genes suppressing glycolysis, metastasis and angiogenesis. The observation that hypoxia drives these processes through the accumulation of epimutations is not only surprising, but also adds another layer of complexity to understanding hypoxia biology. Indeed, until now, hypoxia-triggered processes have traditionally been interpreted in the context of PHD-mediated stability of the HIF transcription factor complex and its subsequent binding to DNA. Interestingly, high doses of anti-angiogenic agents are known to stimulate the metastatic spread of murine cancer models, at least in specific settings (Ebos et al., 2009; Paez-Ribes et al., 2009). Indeed, although VEGF gene inactivation in tumor cells provides a clinical survival benefit, pretreatment of healthy mice with VEGF inhibitors prior to intravenous inoculation of tumor cells "conditions" them to more aggressive metastasis with shortened survival. Also, treatment of various tumor models with VEGF inhibitors can cause a persistent switch to "vasoinvasion", leading to increased metastasis. Tumor hypoxia generally has been considered as a driver of this increased escape behavior. We similarly used a high dose of the VEGF inhibitor sFlk1, thereby boosting tumor hypoxia in PyMT mice. The invention described here by which hypermethylation accumulates under hypoxia could thus also be underlying these escape mechanisms. On the other hand, we also observed that tumor vessel normalization, which significantly reduced tumor hypoxia, led to fewer epimutations. Interestingly, several preclinical studies have shown that pharmacological inhibition of VEGF signaling can transiently repair the abnormal tumor vasculature, thereby improving tumor oxygenation and enhancing the delivery of chemotherapies to the tumor (this process is referred to as vascular normalization) (Carmeliet and Jain, 2011; Maes et al., 2014). A subset of glioblastoma patients that showed benefit from cediranib, a pan-VEGF receptor tyrosine kinase inhibitor, exhibited a high "vascular normalization index", as revealed by an increase in tumor perfusion, a reduced vessel diameter and permeability, and improved tumor oxygenation (Batchelor et al. 2013). Since we observed a clear reversal of HM in normalized compared to hypoxic PyMT tumors, these observations suggest that the therapeutic benefits of vessel normalization might also occur through reversing epimutations that have accumulated in hypoxic tumors. Although it is currently unclear to what extent these epimutations are indeed reversible, our data also suggest that countering epimutations induced by hypoxia-inducing therapies, for instance through co-administration of drugs inhibiting DNA methylation or by normalizing tumor blood supply, may prove therapeutically beneficial (Yang et al., 2014).

Materials and Methods

All materials were molecular biology grade. Unless noted otherwise, all were from Sigma (Diegem, Belgium). Detailed methods are described in Supplemental Experimental Procedures.

Cell lines: MCF7, MCF10A, A549, H1299, SH-SY5Y, Hep G2, Hep 3B2, HT-1080, NCI-H358, LLC, Neuro-2a, 4T1 and SK-N-BE2c cells lines were obtained from the American Type Culture Collection and their identity was not further authenticated. These are not listed in the database of commonly misidentified cell lines maintained by ICLAC. LLC, Neuro-2a, 4T1, Hep G2, HT-1080, Hep 3B2, MCF7 and A549 cells were cultured at 37° C. in Dulbecco's modified Eagle medium (DMEM) with 10% fetal bovine serum (FBS), 5 ml of 100 U/ml Penicillin-Streptomycin (Pen Strep, Life Technologies) and 5 ml of L-Glutamine 200 mM, NCI-H358, H1299 and SK-N-BE2c cell lines were cultured at 37° C. in Roswell Park Memorial Institute (RPMI) 1640 Medium (RPMI) 10% FBS 1% Pen Strep and 1% L-Glutamine. MCF10A cells were cultured at 37° C. in DMEM/F-12 (Dulbecco's Modified Eagle Medium/Nutrient Mixture F-12) supplemented with 5% horse serum (Life Technologies), 20 ng/ml human Epidermal Growth Factor (Prepotec), 0.5 µg/ml hydrocortisone, 100 ng/ml cholera toxin, 10 µg/ml insulin, and 100 U/ml Pen Strep. The SH-SY5Y cell line was cultured at 37° C. in DMEM/F-12 supplemented with 10% FBS, 2% (PenStrep) and 1% Non Essential Amino Acids (MEM). Mouse J1 ES cells were cultured feeder-free in fibroblast-conditioned medium. Cell cultures were confirmed to be mycoplasma-free every month.

Cell culture: Cells were cultured as described in the Supplemental Experimental Procedures. Normoxic cell cultures were at atmospheric oxygen concentrations with 5% CO2. To render cultures hypoxic, they were incubated in an atmosphere of 0.5% oxygen, 5% CO2 and 94.5% N2. Where indicated, IOX2 (50 µM) or dimethyl α-ketoglutarate (2 mM) were added to fresh culture medium, using an equal volume of carrier (DMSO) as control for IOX2. Cells were plated at a density tailored to reach 80-95% confluence at the end of the treatment. Fresh medium was added to the cells just before the hypoxia exposure. For glutamine-free culture experiments, dialysed FBS was added to glutamine-free DMEM, and supplemented with glutamine (4 mM) for control. Extraction of DNA, RNA, proteins or metabolites was done 24 hours after the start of treatment, unless indicated otherwise.

DNA extraction: DNA was extracted as described below with all buffers supplemented with deferoxamin (DFO, 200 µM) and 2,6-di-tert-butyl-4-methyl-hydroxytoluene (BHT, 200 µM). Culture cells were washed on ice with ice-cold phosphate-buffer saline (PBS) with deferoxamin (PBS-DFO, 200 µM), detached using cell scrapers and collected by centrifugation (400×G, 4° C.). Tumor samples were flash-frozen after dissection in liquid nitrogen and stored at −80° C. until further processing. For extraction, tumors were thawed in PBS-DFO, dissociated using a pestle and incubated with proteinase K addition (200 units) for 30 minutes at 56° C. Nucleic acids were subsequently extracted using the Wizard Genomic DNA Purification (Promega, Leiden, The Netherlands) kit according to instructions, with all buffers supplemented with DFO (200 µM) and 2,6-di-tert-butyl-4-methyl-hydroxytoluene (BHT, 200 µM), dissolved in 80 µL PBS-DFO-BHT with RNAse A (200 units, NEB, Ipswich, Mass., USA), incubated for 10 minutes at 37° C. After proteinase K addition (200 units) and incubation for 30 minutes at 56° C., DNA was purified using the QIAQuick blood and tissue kit (all buffers supplemented with DFO and BHT), eluted in 100 µL of 10 mM Tris (pH 8) and stored at −80° C. until further processing.

LC/MS: To measure the 5-methylcytosine, 5-hydroxymethylcytosine and 8-oxo-7,8-dihydroguanine content of DNA, three technical replicates were run for each sample, and each experiment was repeated at least 4 times. DNA was spiked with specific amounts of the corresponding isotopically labeled standards, enzymatically hydrolyzed and analyzed using LC-ESI-MS/MS as specified in Supplemental Experimental Procedures. The nucleosides were analyzed in the positive as well as in the negative ion selected reaction monitoring mode (SRM).

Metabolites: For metabolite extractions, 12-well cell culture dishes were placed on ice and washed twice with ice-cold 0.9% NaCl, after which 500 µL of ice-cold 80% methanol was added to each well. Cells were scraped and 500 µL was transferred to a vial on ice. Wells were washed with 500 µL 80% methanol, which was combined with the initial cell extracts. The insoluble fraction was pelleted at 4° C. by a 10 minute 21,000×G centrifugation. The pellet (containing the proteins) was dried, dissolved in 0.2 N NaOH at 96° C. for 10 minutes and quantified using a bicinchoninic acid protein assay (BCA, Pierce, Erembodegem, Belgium), whereas the supernatant fraction was processed for metabolite profiling. Derivation and measurement of metabolites: The supernatant fraction containing metabolites was transferred to a new vial and dried in a Speedvac. The dried supernatant fraction was dissolved in 45 µL of 2% methoxyamine hydrochloride in pyridine and held for 90 minutes at 37° C. in a horizontal shaker, followed by derivatization through the addition of 60 µL of N-(tert-butyldimethylsilyl)-n-methyl-trifluoroacetamide with 1% tert-butyldimethylchlorosilane and a 60 minute incubation at 60° C. Samples were subsequently centrifuged for 5 minutes at 21,000×G, and 85 µL was transferred to a new vial and analysed using a gas-chromatography based mass spectrometer (triple quadrupole, Agilent) operated in Multiple Reaction Monitoring (MRM) mode. Analysis of metabolite concentrations: For each sample, metabolite measurements were normalized per sample to the corresponding protein concentration estimates, and expressed relative to control-treated samples. Four biological replicates were run for each sample, and the experiment was repeated 4 times using independent samples (n=16). Differences in metabolite concentration were assessed using a Student's t-test.

Western blotting: Protein were extracted, separated and blotted on polyvinylidene fluoride membranes as described in the Supplemental Experimental Procedures. Membranes were washed, and incubated with TET1 (MA5-16312, Thermo), TET2 (61390, Active Motif), TET3 (PA5-31860, Thermo) or β-actin (4967, Cell Signaling) at 1:1000 dilution, and HIF1α (AF1935, R&D) at 1:400 dilution. Secondary antibodies and detection were as described (Zhao et al., 2014).

RT-qPCR: For RNA extractions, cell culture medium was removed, TRIzol (Life Technologies) added and processed according to guidelines. RT-qPCR was performed as described (Zhao et al., 2014), using 2× TaqMan® Fast Universal PCR Master Mix or SYBR® GreenER™ qPCR SuperMix Universal (both from Life Technologies), TaqMan probes and primers (IDT, Leuven, Belgium) whose sequence is available upon simple request. Thermal cycling and fluorescence detection were done on a LightCycler 480 Real-Time PCR System (Roche), and differential expression calculated using the ΔΔCt method (Schmittgen and Livak, 2008). Taqman assay amplification efficiencies were verified using serial cDNA dilutions, and estimated to be >95%.

TET mRNA concentrations and hypoxia marker gene induction: mRNA concentration analysis and statistics: Ct values were determined for each sample and gene of interest in technical duplicates, and normalized according to the corresponding amplification efficiency. Per sample, TET expression was expressed relative to the β-2-microglobulin levels by subtraction of their average Cts. Concentrations were expressed as averages of at least 5 independent biological replicates. Concentrations were compared between hypoxia and normoxia, or between control and treated using a Student's t-test. No statistical methods were used to predetermine sample size. Hypoxia marker gene induction: To further verify intactness of the hypoxia response program, hypoxia marker gene expression was verified. We analyzed mRNA levels of genes encoding the E1B 19K/Bcl-2-binding protein Nip3 (BNIP3) and fructose-bisphosphate aldolase (ALDOA), 2 established hypoxia marker genes (Sermeus et al 2008). RT-qPCR was performed as described for the TET mRNA concentration assays, and differential expression was calculated using the ΔΔCt method (Schmittgen et al 2008). We moreover excluded that the increase in HIF1α protein concentrations was secondary to a transcriptional upregulation, by assessing HIF1A mRNA expression in parallel. mRNA concentrations were expressed relative to normoxic controls. Differences in mRNA concentration were assessed using a Student's t-test on 5 or more independent biological replicates.

Validation of hypoxia induction and Tet protein expression: Western blotting for Hif1α, Tet1, Tet2 and Tet3: To assess HIF1α protein stabilization, proteins were extracted from cultured cells as follows: cells were placed on ice, and washed twice with ice-cold PBS. Proteins were extracted with extraction buffer (50 mM Tris HCl, 150 mM NaCl, 1% Triton X-100, 0.5% Na-deoxycholate and 0.1% SDS) with 1× protease inhibitor cocktail. Protein concentrations were determined using a bicinchoninic acid protein assay (BCA, Thermo Scientific) following the manufacture's protocol, and an estimated 60 μg protein was loaded per well on a NuPAGE Novex 3-8% Tris-Acetate Protein gel (Life Technologies), separated by electrophoresis and blotted on polyvinylidene fluoride membranes. Membranes were activated with methanol and washed, and incubated with rabbit β-actin (4967, Cell Signaling) at 1:1000 dilution and rabbit HIF-1α (C-Term) Polyclonal Antibody (Cayman Chemical Item 10006421) 1:3000. Secondary antibodies and detection were according to routine laboratory practices. Western blotting was done on 3 independent biological replicates.

Hydroxylation assay using nuclear extracts: MCF7 cells were cultured for 24 h under control or hypoxic conditions (resp. 21 and 0.5% $O_2$), chilled on ice and processed for extraction of nuclear proteins using the NE-PER Nuclear and Cytoplasmic Extraction Kit (Thermo Scientific). The activity of control and hypoxic extracts was assessed in parallel using the Colorimetric Epigenase 5mC-Hydroxylase TET Activity/Inhibition Assay Kit (Epigentek, Farmingdale, USA) according to manufacturer's instructions. Reactions were allowed to proceed for one hour, after which washing and detection of 5hmC were done according to manufacturer's instructions. Differences between hypoxia and control were analyzed using ANOVA, for 5 independent experiments.

DNA hydroxymethylation assay using purified TET enzyme: The genomic DNA used was in this assay was extracted from Tet-triple-knockout ES cells (a gift from Prof. Guo-Liang Xu, State Key Laboratory of Molecular Biology, CAS, Shanghai, China), and it therefore was devoid of 5hmC (He et al 2011). To enable efficient denaturation, it was digested using MseI prior to the assay and purified using solid phase reversible immobilisation paramagnetic beads (Agencourt AMPure XP, Beckman Coulter, USA). The assays were performed in Whitley H35 Hypoxystations (don Whitley Scientific, UK) at 37° C., 5% $CO_2$, $N_2$, plus the following oxygen tensions: 0.1%, 0.25%, 0.5%, 1%, 2.5%, 5%, 10% and 21%. Hypoxystations were calibrated less than 1 month prior to all experiments. Optimized assay components were as follows: 1.0 μg/μL bovine serum albumin (New England Biolabs), 50 mM Tris (pH 7.8), 100 μM dithiothreitol (Life Technologies), 2 ng/μL digested gDNA, 250 μM α-ketoglutarate, 830 μM ascorbate, 200 μM $FeSO_4$ and 45 ng/μL Tet1 enzyme (Wisegene, USA). The major assay components ($H_2O$, BSA and Tris) used for all samples were allowed to pre-equilibrate at 0.1% $O_2$ for 1 hour. These and the remaining assay buffer components (<100 μL) were then pre-equilibrated at the desired oxygen tension for 15 min, and mixed prior to addition of Tet1 enzyme in a total reaction volume of 25 μL. Reactions were allowed to proceed for 3 min, longer incubations showed a decrease in activity. Reactions were stopped with 80 mM EDTA and stored at −80° C. To measure the resulting 5hmC content of the DNA, reactions were diluted to 100 μL, denatured for 10 min at 98° C. and analysed in duplicate using the Global 5-hmC Quantification Kit (Active Motif) following manufacturer's instructions. Michaelis-Menten, Lineweaver-Burk plots and the resulting Km values were estimated using R.

Hypoxia-induced changes in genomic distribution of 5(h)mC in MCF7 cells: DIPseq: Methodology: To assess where in the genome the levels of 5mC and 5hmC were altered, we performed DNA immunoprecipitations coupled to high-throughput sequencing (DIPseq). MCF7 cell culture and DNA extractions were as described for LC/MS analyses. Library preparations and DNA immunoprecipitations were as described (Taiwo et al., 2012), using established antibodies targeting 5mC (clone 33D3, Eurogentec Liege, Belgium) and 5hmC (Active Motif cat no 39791, La Hulpe, Belgium). For 5hmC-DIP-seq, paired barcoded libraries prepared from DNA of hypoxic and control samples were mixed prior to capture, to enable a direct comparison of 5hmC-DIP-seq signal to the input. A single end of these libraries was sequenced for 50 bases on a HiSeq 2000, mapped using Bowtie and extended for the average insert size (150 bases). Analysis: MACS peak calling, read depth quantification and annotation with genomic features as annotated in EnsEMBL build 77 was done using using SeqMonk. Differential (hydroxy-) methylation was quantified by EdgeR (McCarthy et al., 2012), using either 3 or 5 independent pairs of control and hypoxic samples (resp. for 5hmC-DIP-seq and 5mC-DIP-seq). Results were reported for 5hmC peak areas that exhibited a change significant at a 5% and 50% FDR. Target enrichment bisulfite sequencing using SeqCapEpi: To confirm enrichment of 5mC at gene promoters using an independent method, DNA libraries were prepared using methylated adapters and the NEBNext DNA library prep master mix set following manufacturer recommendations. Libraries were bisulfite-converted using the Imprint DNA modification kit (Sigma) as recommended, and PCR amplified for 12 cycles using barcoded primers (NEB) and the KAPA HiFi HS Uracil+ ready mix (Sopachem, Eke, Belgium) according to manufacturer's instructions. Fragments were selected from these libraries using the SeqCap Epi CpGiant Enrichment Kit (Roche) following the manufacturer's instructions, sequenced from both ends for 100 bases on a HiSeq 2000. For analyzing these sequences, sequencing reads were trimmed for adapters using TrimGalore and mapped on a bisulfite-converted human genome (GRCh37) using BisMark. The number of methylated and unmethylated cytosines in captured regions were quantified using Seqmonk for each experiment. Differential methylation of regions of interest was assessed by Fisher's exact test, and for 5 independent biological replicates, t-scores were averaged following Fisher's method.

RNAseq: To assess the impact of the increased 5mC occupancy at gene promoters on their expression, RNAseq was performed. Briefly, total RNA was extracted using TRIzol (Invitrogen), and remaining DNA contaminants in 17-20 ug of RNA was removed using Turbo DNase (Ambion) according to the manufacturers instruction. RNA was repurified using RNeasy Mini Kit (Qiagen). Ribosomal RNA present was depleted from 5 ug of total RNA using the RiboMinus Eukaryote System (Life technologies). cDNA synthesis was performed using SuperScript® III Reverse Transcriptase kit (Invitrogen). 3 µg of Random Primers (Invitrogen), 8 µL of 5× First-Strand Buffer and 10 µL of RNA mix was incubated at 94° C. for 3 min and then at 4° C. for 1 min. Then, 2 µL of 10 mM dNTP Mix (Invitrogen), 4 µL of 0.1 M DTT, 2 µL of SUPERase• In™ RNase Inhibitor 20 U/µL (Ambion), 2 µL of SuperScript™ III RT (200 units/µL) and 8 µL of Actinomycin D (1 µg/µL) were added and the mix were incubated 5 min at 25° C., 60 min at 50° C. and 15 min at 70° C. to heat inactivating the reaction. The cDNA was purified by using 80 µL (2× volume) of Agencourt AMPure XP and eluted in 50 µL of the following mix: 5 µL of 10× NEBuffer 2, 1.5 µL of 10 mM dNTP mix (10 mM dATP, dCTP, dGTP, dUTP, Sigma), 0.1 µL of RNaseH (10 U/µL, Ambion), 2.5 µL of DNA Polymerase I Klenov (10 U/µL, NEB) and water until 50 µL. The eluted cDNA was incubated for 30 min at 16° C., purified by Agencourt AMPure XP and eluted in 30 µL dA-Tailing mix (2 µL of Klenow Fragment, 3 µL of 10× NEBNext dA-Tailing Reaction Buffer and 25 µL of water). After 30 min incubation at 37° C., the DNA was purified by Agencourt AMPure XP, eluted in TE buffer and quantified on NanoDrop. Subsequent library preparation was done using the DNA library prep master mix set and sequencing was performed as described for ChIP-seq. Expression levels (reads per million) of genes displaying significant increases in methylation at their gene promoter, as determined using SeqCapEpi, was compared between control and hypoxic samples.

TCGA data analysis: RNAseq read counts, gene mutation data as well as DNA methylation data from Infinium HumanMethylation450 BeadChip arrays were downloaded from the TCGA server. We identified 695 breast tumors and 63 glioblastomas for which each of the 3 datasets were available. From the TCGA pan-cancer analysis, we selected all solid cancer types for which >100 samples were available with both gene expression data (RNAseq) and DNA methylation data (Illumina Infinium HumanMethylation450 BeadChip). These were 425 bladder carcinomas, 695 breast carcinomas, 244 colorectal adenocarcinomas, 542 head and neck squamous cell carcinomas, 291 kidney renal cell carcinomas, 450 lung adenocarcinomas, 378 lung squamous cell carcinomas, and 195 uterine carcinomas. Corresponding RNAseq read counts as well as DNA methylation data from Infinium HumanMethylation450 BeadChip arrays were downloaded from the TCGA server. Breast tumor subtype was annotated for 208 tumors, and for the remaining tumors imputed by unsupervised hierarchical clustering of genes in the PAM50 gene expression signature (Parker et al 2009). Other clinical and histological variables were available for >95% of tumors, and missing values were encoded as not available. Gene mutation data was available 129 bladder carcinomas, 646 breast carcinomas, 200 colorectal adenocarcinomas, 306 head and neck squamous cell carcinomas, 241 kidney renal cell carcinomas, 182 lung adenocarcinomas, 74 lung squamous cell carcinomas, and 3 uterine carcinomas.

Stratification of tumors for hypoxia and proliferation: To identify which of these tumor samples were hypoxic or normoxic, we performed unsupervised hierarchical clustering based a modification (Ward.D of the clusth function in R's stats package) of the Ward error sum of squares hierarchical clustering method (Murtagh and Legendre, 2014), on normalized log-transformed RNAseq read counts for 14 genes that make up the hypoxia metagene signature (ALDOA, MIF, TUBB6, P4HA1, SLC2A1, PGAM1, ENO1, LDHA, CDKN3, TPI1, NDRG1, VEGFA, ACOT7 and ADM) (Buffa et al 2010). In each case the top 3 subclusters identified were annotated as normoxic, intermediate and hypoxic. To identify which of these tumor samples were high- or low-proliferative, we performed unsupervised hierarchical clustering based a modification (Ward.D of the clusth function in R's stats package) of the Ward error sum of squares hierarchical clustering method (Murtagh and Legendre, 2014), and this for all genes annotated to an established tumor proliferation signature (MKI67, NDC80, NUF2, PTTG1, RRM2, BIRC5, CCNB1, CEP55, UBE2C, CDC20 and TYMS) (Nielsen et al 2010). Tumors in the top 2 subclusters identified were labeled as high- or low-proliferative. Analysis of the top 1000 CpGs most hypermethylated versus normal tissue: To identify tumor-associated hypermethylation events, we compared 450K methylation data from tumors and normal tissues. All available DNA methylation data from normal tissue (matched or unmatched to tumor samples, on average 59 per cancer type, representing 472 in total, range=21-160) were downloaded. For each of the 8 tumor types investigated, we selected the top 1,000 CpGs that showed the highest average tumor-associated increases in DNA methylation. Per tumor type, unsupervised hierarchical clustering based a modification of the Ward error sum of squares hierarchical clustering method (Ward.D of the clusth function in R's stats package) (Murtagh and Legendre, 2014), and annotated the first 3 clusters identified as having low, intermediate and high methylation. Cluster co-membership for methylation and hypoxia metagene expression were analysed using the Cochran-Armitage test for trend. Analyses using the top 100, 500, 5,000 or 10,000 CpGs yielded near identical results (not shown). Analysis of hypermethylation events: We next applied a method to identify those CpGs that are hypermethylated only in a subset of all tumors. Such more rare events are typically found in cancer, where hypermethylation inactivates a gene in only a subset of tumors. Hypermethylation of individual CpGs at gene promoters in individual tumors was assessed as follows: To achieve a normal distribution, all β-values were transformed to M-values (Du et al 2010) using $M=\log_2(\beta/(1-\beta))$. For each tumor type, the mean μ and standard deviation σ of the M value across all control (normoxic) tumors was next calculated for each CpG, and used to assign Z-values to each CpG in each tumor using $Z=(M-\mu)/\sigma$. These Z-values describe the deviation in normal methylation variation for that probe. To identify CpGs that display an extreme deviation, we selected those for which the Z-value exceeded 5.6 (i.e. the mean plus 5.6 times the standard deviation, corresponding to a Bonferroni-adjusted P-value of 0.01); they were called as hypermethylated in that tumor. This analysis was preferred over Wilcoxon-based models that assess differences in the average methylation level between subgroups, as the latter does not enable the identification or quantification of the more rare HM events in individual promoters or CpGs. To identify genes with frequently hypermethylated CpGs in their promoter, the number of HM events in that promoter was counted in all tumors, and contrasted to the expected number of HM events in that promoter (i.e. the general HM frequency×the number of CpGs assessed in that promoter×the number of tumors) using Fisher's exact test. Genes with an associated Bonferroni-adjusted P-value below 0.01 were retained and called as frequently hypermethylated in that tumor type. To assess what fraction of these HM events are hypoxia-related, we assumed that the fraction of events detected under normoxia was hypoxia-unrelated, and that all excess events detected in intermediate and hypoxic tumors were hypoxia-related. For example, in 695 breast carcinomas, 0.25% of CpGs were hypermethylated in 253 normoxic tumors, 0.81% in 352 intermediate and 1.40% in 90 hypoxic tumors. So, 0.56% and 1.15% of HM events in resp. intermediate and hypoxic tumors were hypoxia-related. Taking into account the number of tumors, 0.25% of HM events (i.e. (0.25%×253+0.25%×352+0.25%×90)÷695) are not hypoxia-related, and 0.43% are hypoxia related (i.e. (0%×253+0.56%×352+1.15%×90)÷695). Hence, 63% of all HM events (i.e. 0.43÷(143+0.25)). To assess the contribution of hypoxia to HM relative to other covariates, partial $R^2$ values were calculated for the contribution of each covariate in a linear model, and compared to the total $R^2$ achieved by the model. To identify genes with CpGs in their promoter that are more frequently hypermethylated in hypoxic than normoxic tumors, the number of HM events in that promoter was counted in all hypoxic tumors, and contrasted to the number found in normoxic tumors. Differences in frequencies were assessed using Fisher's exact test, and genes with an associated Bonferroni-adjusted P-value below 0.01 were retained and called as hypermethylated upon hypoxia. Enrichment of ontologies associated with these genes that are more frequently hypermethylated in hypoxic than normoxic tumors was assessed Fishers exact test as implemented in R's topGO package. Analysis of mutations: To assess the impact of somatic mutations on hypoxia-associated HM frequencies, we analyzed the top 50 genes described to be most frequently mutated in the pan-cancer analysis (TCGA, 2013) and supplemented this list with genes known to cause hypermethylation upon mutation (i.e. IDH1, IDH2, SDHA, FH, TET1, TET2 and TET3). Mutations in IDH1 and IDH2 were retained if they respectively affected amino acid R132, and amino acids R140 or R172. Mutations in other genes were scored using Polyphen, and only mutations classified as probably damaging were retained. 7 mutations were found in lung tumors, 3 mutations in colorectal tumors, 8 mutations in breast tumors and 6 mutations (all $IDH1^{R132}$) in glioblastomas. None of these mutations were enriched in hypoxic subsets. In multivariate analyses of variance, in each of the tumor types analyzed, mutations in these genes were significantly associated with increased HM frequencies, but also hypoxia was independently and significantly associated with the HM frequency. Correlation between hypermethylation and expression of TET or DNMT enzymes: Gene expression values (reads per million) of DNMT and TET enzymes were determined for each tumor using available RNAseq data. Tumor suppressor gene HM in each tumor was determined as the average methylation level across the promoters of all tumor suppressor genes annotated by Vogelstein and colleagues (Vogelstein et al 2013). Tumor suppressor gene methylation in each tumor was subsequently correlated to TET or DNMT gene expression in that tumor, correcting for hypoxia status, using ANOVA.

TAB and BS using 450K arrays for 24 lung tumors: Tumor samples: Newly diagnosed and untreated non-small-cell lung cancer patients scheduled for curative-intent surgery were prospectively recruited. Included subjects had a smoking history of at least 15 pack-years. The study protocol was approved by the Ethics Committee of the University Hospital Gasthuisberg (Leuven, Belgium). All participants provided written informed consent. In the framework of a different project (Wauters et al 2015), RNAseq was performed on 39 tumors from these patients. Gene expression for these samples was clustered for their hypoxia metagene signature (Buffa et al 2010). This yielded 2 clear clusters, containing respectively 24 and 15 normoxic and hypoxic tumors. Twelve samples were randomly selected from each cluster, in order to perform 5hmC and 5mC profiling. Illumina Infinium Human Methylation450 BeadChips: For TAB-chip, DNA was glycosylated and oxidized as described (Yu et al 2012), using the 5hmC TAB-Seq Kit (WiseGene, Chicago, USA). Subsequently, bisulfite. conversion, DNA amplification and array hybridization were done following manufacturer's instructions. Analysis of TAB-chip and BS-chip: Data processing was largely as described (Nazor et al 2014). In brief, intensity data files were read directly into R. Each sample was normalized using Subset-quantile within array normalization (SWAN) for Illumina Infinium Human-Methylation450 BeadChips (Yu et al 2012). Batch effects between chips and experiments were corrected using the runComBat function from the ChAMP bioconductor package (Morris et al 2014). For obtaining 5mC-specific beta values, TAB-array generated normalized beta values were subtracted from the standard 450K generated normalized beta values, exactly as described (Nazor et al 2014).

Murine cancer models: Animal experiments received local ethical approval (P098/2014). Animals were intercrossed and maintained as described in Supplemental Experimental Procedures. Mammary tumors were harvested at 16 weeks from Tg(MMTV-PyMT) and Tg(MMTV-PyMT); Phd2−/+ mice. For Flk1-overexpression studies, tumors allowed to develop for 11 weeks. Subsequently, 2.5 μg of plasmid (sFlk1-overexpressing or empty p156RRL2 vector) per gram of mouse body weight was introduced in the blood stream using hydrodynamic injections (Liu et al., 1999). sFlk1 overexpression was monitored at 4 days after injection and at sacrifice (18 days after the injection), by eye bleeds followed by an enzyme-linked immunosorbent assay for sFlk1 (R&D Systems, Abingdon, UK) in blood plasma. At 12 weeks of age, mice were sacrificed and mammary tumors harvested blinded for treatment. For the Phd2$^{+/-}$ experiments, male Tg(MMTV-PyMT) FVB mice were intercrossed with female Phd2$^{-/+}$ mice, yielding litters of which half have either a Tg(MMTV-PyMT) genotype or a Tg(MMTV-PyMT); Phd2$^{-/+}$ genotype. For the Phd2$^{wt/fl}$ experiments, male Tg(MMTV-PyMT) FVB mice were intercrossed with female Tie2-cre; Phd2$^{wt/fl}$ mice as described (Kuchnio et al 2015), yielding litters of which half have either a Tie2-cre; Tg(MMTV-PyMT); Phd2$^{wt/wt}$ genotype or a Tie2-cre; Tg(MMTV-PyMT); Phd2$^{-/+}$ genotype. At 16 weeks of age, female mice were sacrificed and mammary tumors harvested.

Targeted deep BS-seq: As no murine capture kit was available for targeted BSseq, a specific ampliconBS was developed for a set of 15 tumor suppressor gene promoters and 5 oncogene promoters. More specifically, DNA was bisulfite-converted using the Imprint DNA modification kit and amplified using the MegaMix Gold 2× mastermix and validated primer pairs. Per sample, PCR products were mixed to equimolar concentrations, converted into sequencing libraries using the NEBNext DNA library prep master mix set and sequenced to a depth of ~500×. Mapping and quantification were done as described for SeqCapEpi. The average and variance of methylation level M values in normal mammary glands were used as baseline, and amplicons displaying over 3 standard deviations more methylation (FDR-adjusted $P<0.05$) than this baseline were called as hypermethylated. At least 9 different tumors, each from different animals, were profiled per genotype or treatment, and differences in HM frequencies between sets of tumors were assessed using Mann-Whitney's U-test.

Verification of hypoxia induction: Hypermethylation of individual CpGs at gene promoters in individual tumors was assessed as follows: To achieve a normal distribution, all β-values were transformed to M-values using $M=\log 2(\beta/(1-\beta))$. For each tumor type, the mean μ and standard deviation σ of the M value across all control (normoxic) tumors was next calculated for each CpG, and used to assign Z-values to each CpG in each tumor using $Z=(M-\mu)/\sigma$. These Z-values describe the deviation in normal methylation variation for that probe. To identify CpGs that display an extreme deviation, we selected those for which the Z-value exceeded 5.6 (i.e. the mean plus 5.6 times the standard deviation, corresponding to a Bonferroni-adjusted P-value of 0.01); they were called as hypermethylated in that tumor. This analysis was preferred over Wilcoxon-based models that assess differences in the average methylation level between subgroups, as the latter does not enable the identification or quantification of the more rare HM events in individual promoters or CpGs.

Supplemental Experimental Procedures.

Cell culture: MCF7 cells were cultured at 37° C. in Dulbecco's modified Eagle medium (DMEM) with 10% fetal bovine serum (FBS). MCF10A cells were cultured at 37° C. in DMEM/F-12 (Dulbecco's Modified Eagle Medium/Nutrient Mixture F-12) supplemented with 5% horse serum (Life Technologies), 20 ng/ml human Epidermal Growth Factor (Prepotec), 0.5 μg/ml hydrocortisone, 100 ng/ml cholera toxin, 10 μg/ml insulin, and 100 U/ml Penicillin-Streptomycin (Life Technologies). Mouse J1 ES cells were cultured freeder-free in fibroblast-conditioned medium.

LC/MS: 0.5 to 2 μg DNA in 25 μL H2O were digested as follows: an aqueous solution (7.5 μL) of 480 μM ZnSO4, containing 42 units Nuclease S1, 5 units antarctic phosphatase, and specific amounts of labeled internal standards were added and the mixture was incubated at 37° C. for 3 h in a Thermomixer comfort (Eppendorf). After addition of 7.5 μL of a 520 μM [Na]2-EDTA solution containing 0.2 units snake venom phosphodiesterase I, the sample was incubated for another 3 h at 37° C. The total volume was 40 μL. The sample was then kept at −20° C. until the day of analysis. Samples were then filtered by using an AcroPrep Advance 96 filter plate 0.2 μm Supor (Pall Life Sciences) and then analyzed by LC-ESI-MS/MS. LC-ESI-MS/MS analysis was performed using an Agilent 1290 UHPLC system and an Agilent 6490 triple quadrupole mass spectrometer coupled with the stable isotope dilution technique. DNA samples were digested to give a nucleoside mixture and spiked with specific amounts of the corresponding isotopically labeled standards before LC-MS/MS analysis. The nucleosides were analyzed in the positive as well as in the negative ion selected reaction monitoring mode (SRM). In the positive ion mode [M+H]+ species and in the negative ion mode [M−H]− species were measured. The resulting cytosine, 5-methylcytosine 5-hydroxymethylcytosine and 8-oxo-7,8-dihydroguanine peak areas were normalized using the isotopically labeled standards, and expressed relative to the total cytosine content (i.e. C+5mC+5hmC). Concentrations were depicted as averages of independent biological replicates, and compared between hypoxia and normoxia, or between control and treated conditions, using a paired Student's t-test. No statistical methods were used to predetermine sample size.

Western blotting: For protein extractions, cultured cell were washed with ice-cold PBS and proteins were extracted with extraction buffer (50 mM Tris HCl, 150 mM NaCl, 1% Triton X-100, 0.5% Na-deoxycholate and 0.1% SDS) with 1× protease inhibitor cocktail. Protein concentrations were determined using a bicinchoninic acid protein assay (Thermo Scientific) following the manufacture's protocol, and an estimated 60 μg protein was loaded per well on a NuPAGE Novex 3-8% Tris-Acetate Protein gel (Life Technologies), separated by electrophoresis and blotted on polyvinylidene fluoride membranes. Membranes were washed, and incubated with TET1 (MA5-16312, Thermo), TET2 (61390, Active Motif), TET3 (PA5-31860, Thermo) or β-actin (4967, Cell Signaling) at 1:1000 dilution, and HIF1α (AF1935, R&D) at 1:400 dilution. Secondary antibodies and detection were as described (Zhao et al., 2014).

Murine cancer models: All animal experiments were approved by the local ethical committee (P098/2014). For the patient-derived xenograft model, redundant material from an endometrial tumor and a breast tumor, removed during surgery, was grafted in the interscapular region of nude mice. Informed consent was obtained from the patient, following the ethical approval of the local ethical committee. The tumor was allowed to grow until 1 cm$^3$, after which it was harvested. 10% of this tumor was reimplanted for in a nude mouse, and the tumor was thus propagated for 3 generations until use in experiment.

Immunofluorescence staining: To mark hypoxic areas, mice were injected with pimonidazole (60 mg/kg, Hypoxyprobe, Massachusetts, USA) i.p. 1 hour before sacrifice. Tumors were harvested, fixed in formaldehyde and embedded in paraffin using standard procedures. Slides were deparafinated and rehydrated 2 xylene baths (5 minutes), followed by 5 times 3 minutes in EtOH baths at decreasing concentrations (100%, 96%, 70%, 50% and water) and a 3 minute Tris-buffered saline (TBS; 50 mM Tris, 150 mM NaCl, pH 7.6) bath. The following antibodies were used for immunofluorescence staining: primary antibodies were FITC-conjugated mouse anti-pimonidazole (HP2-100, Hydroxyprobe), rabbit anti-5hmC (39791, Active Motif), rat anti-polyoma middle T (AB15085, Abcam), rat anti-CD31 (557355, BD Biosciences), rat anti-CD45 (553076, BD Biosciences), rabbit anti-Ki67 (AB15580, Abcam) and mouse anti-pan cytokeratin (C2562, Sigma). Secondary antibodies were Alexa fluor 405-conjugated goat anti-rabbit (A31556, Thermo Fisher), Alexa Fluor 647 conjugated goat anti-rat (A-21247, Life technologies), peroxidase-conjugated goat anti-FITC (PA1-26804, Pierce), biotinylated goat anti-rat (A10517, Thermo Fisher) and biotinylated goat anti-rabbit (E043201, Dako). Signal amplification was done using the TSA Fluorescein System (NEL701A001KT, Perkin Elmer) or the TSA Cyanine 5 System (NEL705A001KT, Perkin Elmer). Different protocols were implemented depending on the epitopes of interest. Staining for the following epitopes was combined: CD45, 5hmC, pimo and DNA; PyMT, 5hmC, pimo and DNA; Ki67, pimo and DNA; CD31 and pimo; and pan-cytokeratin, 5hmC, pimo and DNA. Antigen retrieval for CD31, CD45 and pan-cytokeratin was done by a 7 min trypsin digestion, for pimonidazole and Ki67 using AgR at 100° C. for 20 min, followed by cooling for 20 min. Slides were washes in TBS for 5 min, permeabilized in 0.5% Triton-X100 in PBS for 20 min. For 5hmC antigen retrieval, slides were next denatured in 2 N HCl for 10 min, with the HCl being neutralized for 2 min in borax, 1% in PBS pH 8.5, and washed twice for 5 min in PBS. For all slides, endogenous peroxidase activity was quenched using $H_2O_2$ (0.3% in MeOH), followed by three 5 min washes in TBS. Slides were blocked using pre-immune goat serum (X0907, Dako; 20% in TNB; TSA Biotin System kit, Perkin Elmer, Waltham, Mass.). Binding of primary antibodies (anti-5hmC, anti-CD45, anti-CD31 and anti-pan cytokeratin or FITC-conjugated anti-pimonidazole; all 1/100 in TNB) was allowed to proceed overnight. Slides were washed 3× in TNT (0.5% Triton-X100 in TBS) for 5 min, after which secondary antibodies (all 1/100 in TNB with 10% pre-immune sheep serum) were allowed to bind for 45 min: sheep-anti-FITC-PO (for pimo), goat anti-rabbit-Alexa Fluor 405 (for 5hmC), goat anti-rat-Alexa Fluor 647 (for CD45), and biotinylated goat anti-mouse (for pan-cytokeratin). Slides were washed 3×5 min in TNT, after which signal amplification was done for 8 min using Fluorescein Tyramide (1/50 in amplification diluent). Slides stained for pimonidazole that required co-staining slides for Ki67 or PyMT, or slides stained for pan-cytokeratin that required co-staining for pimonidazole were subjected to a second indirect staining for the latter epitopes: after 5 min of TNT and 5 min of TBS, slides were quenched again for peroxidase activity using $H_2O_2$ and blocked using pre-immune goat serum, prior a second overnight round of primary antibody binding (anti-Ki67, FITC-anti-pimo or anti-PyMT, all 1/100). The next day, 3×5 min washes with TNT were followed by a 1 h incubation with a biotinylated goat anti-rabbit antibody (for Ki67) or goat anti-rat (for PyMT), again 3×5 min washes with TNT, a 30 min incubation with peroxidase conjugated to streptavidine (for Ki67 and PyMT) or to anti-FITC (for pimo), again 3×5 min washes with TNT and signal amplification for 8 min using, for pimo, Fluorescein Tyramide and for others Cyanine 5 Tyramide (1/50 in amplification diluent). Finally, slides were stained with propidium iodide+RNAse (550825; BD biosciences) for 15 min, washed for 5 min in PBS and mounted with Prolong Gold (Life Technologies). Immunofluorescence analysis: Slides were imaged on an Nikon A1R Eclipse Ti confocal microscope. 3-5 sections per slide were imaged, and processed using Image J. More specifically, nuclei were identified using the propidium iodide signal, and nuclear signal intensities for Fluorescein and Cy3 (Pimonidazole and 5hmC) measured. Analyses were exclusively performed on slide regions showing a regular density and shape of nuclei, in order to avoid inclusion of acellular or necrotic areas. The pimonidazole signal was used to stratify nuclei into normoxic (pimonidazole negative) and hypoxic (pimonidazole positive) regions, and the 5hmC signal in both populations was compared using ANOVA. PyMT-negative and CD45-positive cells were counted directly; The fraction of pimonidazole and CD31-positive areas was directly quantified using ImageJ across 10 images per slide.

Statistics: Data entry and analysis was performed in a blinded fashion. Statistical significance was calculated by two-tailed unpaired t-test (Excel) or analysis of variance (R) when repeated measures were compared, unless specified otherwise. Data were tested for normality using the D'Agostino-Pearson omnibus test (for n>8) or the Kolmogorov-Smirnov test (for n≤8) and variation within each experimental group was assessed. As mentioned, DNA methylation and RNAseq gene expression data distributions were rendered normal by conversion to M values and $log_2$ transformation respectively. Sample sizes were chosen based on prior experience for in vitro and murine experiments, or on sample and data availability for human tumor analyses.

REFERENCES

Aguilera, A., and Gomez-Gonzalez, B. (2008). Genome instability: a mechanistic view of its causes and consequences. Nature reviews Genetics 9, 204-217.

Arand, J., Spieler, D., Karius, T., Branco, M. R., Meilinger, D., Meissner, A., Jenuwein, T., Xu, G., Leonhardt, H., Wolf, V., and Walter, J. (2012). In vivo control of CpG and non-CpG DNA methylation by DNA methyltransferases. PLoS genetics 8, e1002750.

Batchelor, T. T., Gerstner, E. R., Emblem, K. E., Duda, D. G., Kalpathy-Cramer, J., Snuderl, M., Ancukiewicz, M., Polaskova, P., Pinho, M. C., Jennings, D., et al. (2013). Improved tumor oxygenation and survival in glioblastoma patients who show increased blood perfusion after cediranib and chemoradia lion. Proc Natl Acad Sci USA 110, 19059-19064.

Branco, M. R., Ficz, G., and Reik, W. (2012). Uncovering the role of 5-hydroxymethylcytosine in the epigenome. Nature reviews Genetics 13, 7-13.

Buffa, F. M., Harris, A. L., West, C. M., and Miller, C. J. (2010). Large meta-analysis of multiple cancers reveals a common, compact and highly prognostic hypoxia metagene. Br J Cancer 102, 428-435. Cancer Genome Atlas, N. (2012). Comprehensive molecular portraits of human breast tumours. Nature 490, 61-70.

Carmeliet, P., and Jain, R. K. (2011). Principles and mechanisms of vessel normalization for cancer and other angiogenic diseases. Nat Rev Drug Discov 10, 417-427.

Casazza, A., Laoui, D., Wenes, M., Rizzolio, S., Bassani, N., Mambretti, M., Deschoemaeker, S., Van Ginderachter, J. A., Tamagnone, L., and Mazzone, M. (2013). Impeding macrophage entry into hypoxic tumor areas by Sema3A/

Nrp1 signaling blockade inhibits angiogenesis and restores antitumor immunity. Cancer Cell 24, 695-709.

Chang, J. and Erler, J. (2013). Hypoxia-mediated metastasis. In: Tumor microenvironment and cellular stress, Volume 772 of the series Advances in Experimental Medicine and Biology.

Chowdhury, R., Candela-Lena, J. I., Chan, M. C., Greenald, D. J., Yeoh, K. K., Tian, Y.-M., McDonough, M. A., Tumber, A., Rose, N. R., and Conejo-Garcia, A. (2013). Selective small molecule probes for the Hypoxia Inducible Factor (HIF) prolyl hydroxylases. ACS chemical biology 8, 1488-1496.

Du, P. et al. (2010). Comparison of Beta-value and M-value methods for quantifying methylation levels by microarray analysis. BMC Bioinformatics 11, 587.

Ebos, J. M., Lee, C. R., Cruz-Munoz, W., Bjarnason, G. A., Christensen, J. G., and Kerbel, R. S. (2009). Accelerated metastasis after short-term treatment with a potent inhibitor of tumor angiogenesis. Cancer Cell 15, 232-239.

Esteller, M. (2008). Epigenetics in cancer. The New England journal of medicine 358, 1148-1159. Feinberg, A. P., and Irizarry, R. A. (2010). Stochastic epigenetic variation as a driving force of development, evolutionary adaptation, and disease: Proceedings of the National Academy of Sciences 107, 1757-1764.

Figueroa, M. E., Abdel-Wahab, O., Lu, C., Ward, P. S., Patel, J., Shih, A., Li, V., Bhagwat, N., Vasanthakumar, A., Fernandez, H. F., et al. (2010). Leukemic IDH1 and IDH2 mutations result in a hypermethylation phenotype, disrupt TET2 function, and impair hematopoietic differentiation. Cancer Cell 18, 553-567.

Hanahan, D., and Folkman, A. (1996). Patterns and emerging mechanisms of the angiogenic switch during tumorigenesis. Cell 86, 353-364. Harris, A. L. (2002). Hypoxia, a key regulatory factor in tumour growth. Nature Reviews Cancer 2, 38-47.

He, Y. F. et al. Tet-mediated formation of 5-carboxylcytosine and its excision by TDG in mammalian DNA. Science 333, 1303-7 (2011).

Jain, R. K. (2005). Normalization of tumor vasculature: an emerging concept in antiangiogenic therapy. Science 307, 58-62.

Koh, K. P., Yabuuchi A., Rao, S., Huang, Y., Cunniff, K., Nardone, J., Laiho, A., Tahiliani, M., Sommer, C. A., Mostoslaysky, G., et al. (2011). Tet1 and Tet2 regulate 5-hydroxymethylcytosine production and cell lineage specification in mouse embryonic stem cells. Cell stem cell 8, 200-213.

Koivunen, P., Lee, S., Duncan, C. G., Lopez, G., Lu, G., Ramkissoon, S., Losman, J. A., Joensuu, P., Bergmann, U., and Gross, S. (2012). Transformation by the (R)-enantiomer of 2-hydroxyglutarate linked to EGLN activation. Nature 483, 484-488.

Kuchnio, A. et al. The Cancer Cell Oxygen Sensor PHD2 Promotes Metastasis via Activation of Cancer-Associated Fibroblasts. *Cell Rep* 12, 992-1005 (2015).

Leite de Oliveira, R., Deschoemaeker, S., Henze, A. T., Debackere, K., Finisguerra, V., Takeda, V., Roncal, C., Dettori D., Tack, E., Jonsson, V., et al. (2012). Gene-targeting of Phd2 improves tumor response to chemotherapy and prevents side-toxicity. Cancer Cell 22, 263-277.

Liu, F., Song, V., and Liu, D. (1999). Hydrodynamics-based transfection in animals by systemic administration of plasmid DNA. Gene therapy 6, 1258-1266.

Loges, S., Mazzone, M., Hohensinner, P., and Carmeliet, P. (2009). Silencing or fueling metastasis with VEGF inhibitors: antiangiogenesis revisited. Cancer Cell 15, 167-170.

Mack, S. C., Witt, H., Piro, R. M., Gu, L., Zuyderduyn, S., Stutz, A. M., Wang, X., Gallo, M., Garzia, L., Zayne, K., et al. (2014). Epigenomic alterations define lethal CIMP-positive ependymomas of infancy. Nature 506, 445-450.

Maes, H., Kuchnio, A., Peric, A., Moens, S., Nys, K., De Bock, K., Quaegebeur, A., Schoors, S., Georgiadou, M., and Wouters, J. (2014). Tumor vessel normalization by chloroquine independent of autophagy. Cancer Cell.

Majmundar, A. J., Wong, W. J., and Simon, M. C. (2010). Hypoxia-inducible factors and the response to hypoxic stress. Molecular cell 40, 294-309.

Mazzone, M., Dettori, D., Leite de Oliveira, R., Loges, S., Schmidt, T., Jonckx, B., Tian, Y. M., Lanahan, A. A., Pollard, P., Ruiz de Almodovar, C., et al. (2009). Heterozygous deficiency of PHD2 restores tumor oxygenation and inhibits metastasis via endothelial normalization. Cell 136, 839-851.

McCarthy, D. J., Chen, Y., and Smyth, G. K. (2012). Differential expression analysis of multifactor RNA-Seq experiments with respect to biological variation. Nucleic Acids Res, gks042.

Morris, T. J. et al. ChAMP: 450k Chip Analysis Methylation Pipeline. Bioinformatics 30, 428-30 (2014).

Murtagh, F. & Legendre, P. Ward's hierarchical agglomerative clustering method: which algorithms implement Ward's criterion? Journal of Classification 31, 274-295 (2014).

Nazor, K. L. et al. (2014). Application of a low cost array-based technique—TAB-Array—for quantifying and mapping both 5mC and 5hmC at single base resolution in human pluripotent stem cells. Genomics 104, 358-67.

Nielsen, T. O. et al. A comparison of PAM50 intrinsic subtyping with immunohistochemistry and clinical prognostic factors in tamoxifen-treated estrogen receptor-positive breast cancer. Clin Cancer Res 16, 5222-32 (2010).

Oey, H., and Whitelaw, E. (2014). On the meaning of the word 'epimutation'. Trends in genetics.

Paez-Ribes, M., Allen, E., Hudock, J., Takeda, T., Okuyama, H., Vinals F., Inoue, M., Burgers, G., Hanahan, D., and Casanovas, O. (2009). Antiangiogenic therapy elicits malignant progression of turners to increased local invasion and distant metastasis, Cancer Cell 15, 220-231.

Parker, J. S., Mullins, M., Cheang, M. C. U., Leung, S., Voduc, D., Vickery, T., Davies, S., Fauron, C., He, X., and Hu, Z. (2009). Supervised risk predictor of breast cancer based on intrinsic subtypes. Journal of clinical oncology 27, 1160-1167.

Pelicano, H., Carney, D., and Huang, P. (2004). ROS stress in cancer cells and therapeutic implications. Drug Resistance Updates 7, 97-110.

Pfaffeneder, T., Spada, F., Wagner, M., Brandmayr, C., Laube, S. K., Eisen, D., Truss, M., Steinbacher, J., Hackner, B., Kotljarova, O., et al. (2014). Tet oxidizes thymine to 5-hydroxymethyluracil in mouse embryonic stem cell DNA. Nat Chem Biol 10, 574-581.

Pugh, C. W., and Ratcliffe, P. J. (2003). Regulation of angiogenesis by hypoxia: role of the HIF system. Nat Med 9, 677-684.

Quivoron, C., Couronne, L., Della Valle, V., Lopez, C. K., Plo, I., Wagner-Ballon, O., Do Cruzeiro, M., Delhommreau, F., Arnulf, B., and Stern, M.-H. (2011). TET2 inactivation results in pleiotropic hematopoietic abnormalities in mouse and is a recurrent event during human lymphomagenesis. Cancer cell 20, 25-38.

Schmittgen, T. D., and Livak, K. J. (2008). Analyzing real-time PCR data by the comparative CT method. Nature protocols 3, 1101-1108.

Schofield, C. J., and Ratcliffe, P. J. (2004). Oxygen sensing by HIF hydroxylases. Nature Reviews Molecular Cell Biology 5, 343-354.

Sermeus, A. et al. Hypoxia induces protection against etoposide-induced apoptosis: molecular profiling of changes in gene expression and transcription factor activity. Mol Cancer 7, 27 (2008).

Serra, R. W., Fang, M., Park, S. M., Hutchinson, L., and Green, M. R. (2014). A KRAS-directed transcriptional silencing pathway that mediates the CpG island methylator phenotype. eLife 3, e02313.

Shen, L., Wu, H., Diep, D., Yamaguchi, S., D'Alessio, A. C., Fung, H. L., Zhang, K., and Zhang, Y. (2013). Genome-wide analysis reveals TET- and TDG-dependent 5-methylcytosine oxidation dynamics. Cell 153, 692-706.

Stapor, P., Wang, X., Goveia, J., Moens, S., and Carmeliet, P. (2014). Angiogenesis revisited—role and therapeutic potential of targeting endothelial metabolism. J Cell Sci 127, 4331-4341.

Struhl, K. (2014). Is DNA methylation of tumour suppressor genes epigenetic? eLife 3, e02475.

Tahiliani, M., Koh, K. P., Shen, Y., Pastor, W. A., Bandukwala, H., Brudno, Y., Agarwal, S., Iyer, L. M., Liu, D. R., Aravind, L., and Rao, A. (2009). Conversion of 5-methylcytosine to 5-hydroxymethylcytosine in mammalian DNA by MLL partner TET1. Science 324, 930-935.

Taiwo, O., Wilson, G. A., Morris, T., Seisenberger, S., Reik, W., Pearce, D., Beck, S., and Butcher, L. M. (2012). Methylome analysis using MeDIP-seq with low DNA concentrations. Nat Protoc 7, 617-636.

Vanharanta, S., and Massague, J. (2013). Origins of metastatic traits. Cancer cell 24, 410-421.

Vanharanta, S., Shu, W., Brenet, F., Hakimi, A. A., Heguy, A., Viale, A., Reuter, V. E., Hsieh, J. J., Scandura, J. M., and Massague, J. (2013). Epigenetic expansion of VHL-HIF signal output drives multiorgan metastasis in renal cancer. Nat Med 19, 50-56.

Swanton, C. and Beck, S. (2014). Epigentic noise fuels cancer evolution. Cancer Cell, 26, 775-776.

Vaupel, P., Hockel, M. & Mayer, A. (2007) Detection and characterization of tumor hypoxia using pO2 histography, Antioxid Redox Signal 9, 1221-1235.

Vogelstein, B., Papadopoulos, N., Velculescu, V. E., Thou, S., Diaz, L. A., and Kinzler K. W. (2013). Cancer Genome Landscapes. Science 339, 1546-1558.

Weisenberger, D. J., Siegmund, K. D., Campan, M., Young, J., Long, T. I., Faasse, M. A., Kang, G. H., Widschwendter, M., Weener, D., Buchanan, D., et al. (2006). CpG island methylator phenotype underlies sporadic microsatellite instability and is tightly associated with BRAF mutation in colorectal cancer. Nature genetics 38, 787-793.

Williams, K. et al (2011). TET1 and hydroxymethylcytosine in transcription and DNA methylation fidelity. Nature 473, 343-348.

Wauters, E. et al. (2015). DNA methylation profiling of non-small cell lung cancer reveals a COPD-driven immune-related signature. Thorax 70, 1113-1122.

Xiao, M., Yang, H., Xu, W., Ma, S., Lin, H., Zhu, H., Liu, L., Liu, Y., Yang, C., Xu, Y., et al. (2012). Inhibition of alpha-KG-dependent histone and DNA demethylases by fumarate and succinate that are accumulated in mutations of FH and SDH tumor suppressors. Genes & development 26, 1326-1338.

Xu, W., Yang, H., Liu, Y., Yang, Y., Wang, P., Kim, S.-H., Ito, S., Yang, C., Wang, P., and Xiao, M.-T. (2011). Oncometabolite 2-hydroxyglutarate is a competitive inhibitor of α-ketoglutarate-dependent dioxygenases. Cancer cell 19, 17-30.

Yamaguchi, S., Hong, K., Liu, R., Shen, L., Inoue, A., Diep, D., Zhang, K., and Zhang, Y. (2012). Tet1 controls meiosis by regulating meiotic gene expression. Nature 492, 443-447.

Yang, H., Liu, Y., Bei, F., Zhang, J. Y., Ma, S. H., Liu, J., Xu, Z. D., Zhu, H. G., Ling, Z. Q., Ye, D., et al. (2013). Tumor development is associated with decrease of TET gene expression and 5-methylcytosine hydroxylation. Oncogene 32, 663-669.

Yang, X., Han, H., De Carvalho, D. D., Lay, F. D., Jones, P. A., and Liang, G. (2014). Gene body methylation can alter gene expression and is a therapeutic target in cancer. Cancer Cell 26, 577-590.

You, J. S., and Jones, P. A. (2012). Cancer genetics and epigenetics: two sides of the same coin? Cancer cell 22, 9-20.

Yu, M. et al. Tet-assisted bisulfite sequencing of 5-hydroxymethylcytosine. Nat Protoc 7, 2159-70 (2012).

Zhao, B., Yang, Y., Wang, X., Chong, Z., Yin, R., Song, S.-H., Zhao, C., Li, C., Huang, H., and Sun, B.-F. (2013). Redox-active quinones induces genome-wide DNA methylation changes by an iron-mediated and Tet-dependent mechanism. Nucleic Acids Res, gkt1090.

Zhao, H., Thienpont, B., Yesilyurt, B. T., Moisse, M., Reumers, J., Coenegrachts, L., Sagaert, X., Schrauwen, S., Smeets D., and Matthijs, G. (2014). Mismatch repair deficiency endows tumors with a unique mutation signature and sensitivity to DNA double-strand breaks. eLife 3, e02725.

The invention claimed is:

1. A method of treating a human cancer patient with an anti-angiogenic drug, comprising:
   administering a dose of anti-angiogenic drug to the patient;
   obtaining a sample comprising tumor DNA from the human cancer patient, wherein the tumor DNA comprises one or more promoters of tumor suppressor genes;
   assaying the sample to determine the methylation status of the promoter of a tumor suppressor gene selected from the group consisting of the genes KDM6A, NF2, KDM5C, IGFBP2, ARNT2, PTEN, ATM, MLH1, BRCA1, SEMA3B, THBD, and CLDN3;
   detecting hypoxia in the tumor of the human cancer patient when the promoter of the tumor suppressor gene is hypermethylated in the sample in comparison to the methylation level of the promoter of the same tumor suppressor gene in a normoxic control sample matched or unmatched to the sample comprising tumor DNA from the human cancer patient; and
   administering a decreased dose of the anti-angiogenic drug to the human cancer patient when the tumor is hypoxic.

2. The method of claim 1, wherein the tumor DNA is circulating tumor DNA.

3. A method of treating a human cancer patient with a drug normalizing tumor blood vessels, comprising:
   obtaining a sample comprising tumor DNA from the human cancer patient, wherein the tumor DNA comprises one or more promoters of tumor suppressor genes;

assaying the sample to determine the methylation status of the promoter of a tumor suppressor gene selected from the group consisting of the genes KDM6A, NF2, KDM5C, IGFBP2, ARNT2, PTEN, ATM, MLH1, BRCA1, SEMA3B, THBD, and CLDN3;

detecting hypoxia in the tumor of the human cancer patient when the promoter of the tumor suppressor gene is hypermethylated in the sample in comparison to the methylation level of the promoter of the same tumor suppressor gene in a normoxic control sample matched or unmatched to the sample comprising tumor DNA from the human cancer patient; and administering the drug normalizing tumor blood vessels to the human cancer patient when the tumor is hypoxic.

4. The method of claim 3, wherein the tumor DNA is circulating tumor DNA.

\* \* \* \* \*